US 8,652,187 B2

(12) United States Patent
Wells et al.

(10) Patent No.: US 8,652,187 B2
(45) Date of Patent: Feb. 18, 2014

(54) CUFF APPARATUS AND METHOD FOR OPTICAL AND/OR ELECTRICAL NERVE STIMULATION OF PERIPHERAL NERVES

(75) Inventors: Jonathon D. Wells, Seattle, WA (US); Andrew Xing, Bothell, WA (US); Mark P. Bendett, Kirkland, WA (US); Matthew D. Keller, Seattle, WA (US); Charles A. Lemaire, Apple Valley, MN (US)

(73) Assignee: Lockheed Martin Corporation, Bethesda, MD (US)

( * ) Notice: Subject to any disclaimer, the term of this patent is extended or adjusted under 35 U.S.C. 154(b) by 181 days.

(21) Appl. No.: 13/117,122

(22) Filed: May 26, 2011

(65) Prior Publication Data

US 2011/0295346 A1    Dec. 1, 2011

Related U.S. Application Data

(60) Provisional application No. 61/349,810, filed on May 28, 2010, provisional application No. 61/349,813, filed on May 28, 2010, provisional application No. 61/381,933, filed on Sep. 10, 2010, provisional application No. 61/386,461, filed on Sep. 24, 2010.

(51) Int. Cl.
*A61N 1/05* (2006.01)

(52) U.S. Cl.
USPC .................................. 607/89; 607/3; 607/88

(58) Field of Classification Search
None
See application file for complete search history.

(56) References Cited

U.S. PATENT DOCUMENTS 4,064,872 A    12/1977    Caplan

| | | |
|---|---|---|
| 4,215,694 A | 8/1980 | Isakov et al. |
| 4,232,678 A | 11/1980 | Skovajsa |
| 4,296,995 A | 10/1981 | Bickel |
| 4,390,756 A | 6/1983 | Hoffmann et al. |

(Continued)

FOREIGN PATENT DOCUMENTS

| WO | WO 0025112 | 5/2000 | |
|---|---|---|---|
| WO | WO 2010006049 A1 * | 1/2010 | ............... A61N 5/06 |
| WO | WO 2011120540 A1 * | 10/2011 | ............... A61N 1/36 |

OTHER PUBLICATIONS

Huang, Ying-Ying, et al., "Biphasic Dose Response in Low Level Light Therapy", "Dose-Response", 2009, pp. 358-383, vol. 7.

(Continued)

*Primary Examiner* — Sam Yao
*Assistant Examiner* — Boniface N Nganga
(74) *Attorney, Agent, or Firm* — Charles A. Lemaire; Jonathan M. Rixen; Lemaire Patent Law Firm, P.L.L.C.

(57) ABSTRACT

Apparatus and method for making and using devices that generate optical signals, and optionally also electrical signals in combination with one or more such optical signals, to stimulate (i.e., trigger) and/or simulate a sensory-nerve signal in nerve and/or brain tissue of a living animal (e.g., a human), for example to treat nerve damage in the peripheral nervous system (PNS) or the central nervous system (CNS) and provide sensations to stimulate and/or simulate "sensory" signals in nerves and/or brain tissue of a living animal (e.g., a human) to treat other sensory deficiencies (e.g., touch, feel, balance, visual, taste, or olfactory) and provide sensations related to those sensory deficiencies, and/or to stimulate (i.e., trigger) and/or simulate a motor-nerve signal in nerve and/or brain tissue of a living animal (e.g., a human), for example to control a muscle or a robotic prosthesis.

20 Claims, 11 Drawing Sheets

(56) References Cited

U.S. PATENT DOCUMENTS

| | | |
|---|---|---|
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 5,957,960 A | 9/1999 | Chen et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,240,308 B1 | 5/2001 | Hardy et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,746,473 B2 | 6/2004 | Shanks et al. |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,953,341 B2 | 10/2005 | Black |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,010,356 B2 | 3/2006 | Jog et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,131,968 B2 | 11/2006 | Bendett et al. |
| 7,139,603 B2 | 11/2006 | Chance |
| 7,156,866 B1 | 1/2007 | Riggs et al. |
| 7,160,289 B2 | 1/2007 | Cohen |
| 7,177,081 B2 | 2/2007 | Tomita et al. |
| 7,190,993 B2 | 3/2007 | Sharma et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,311,723 B2 | 12/2007 | Seibel et al. |
| 7,324,852 B2 | 1/2008 | Barolat et al. |
| 7,329,251 B2 | 2/2008 | Yamada et al. |
| 7,337,004 B2 | 2/2008 | Classen et al. |
| 7,351,241 B2 | 4/2008 | Bendett et al. |
| 7,391,561 B2 | 6/2008 | Di Teodoro et al. |
| 7,402,167 B2 | 7/2008 | Nemenov |
| 7,488,341 B2 | 2/2009 | Merfeld |

(56) References Cited

U.S. PATENT DOCUMENTS

| | | | |
|---|---|---|---|
| 7,554,578 B2 | 6/2009 | Jayaraman |
| 7,647,112 B2 | 1/2010 | Tracey et al. |
| 7,654,750 B2 | 2/2010 | Brenner et al. |
| 7,736,382 B2 | 6/2010 | Webb et al. |
| 7,747,318 B2 | 6/2010 | John et al. |
| 7,756,588 B2 | 7/2010 | Jog et al. |
| 7,776,631 B2 | 8/2010 | Miles |
| 7,787,170 B2 | 8/2010 | Patel et al. |
| 7,792,588 B2 | 9/2010 | Harding |
| 7,797,029 B2 | 9/2010 | Gibson et al. |
| 7,801,601 B2 | 9/2010 | Maschino et al. |
| 7,803,454 B2 | 9/2010 | Toepel |
| 7,833,257 B2 | 11/2010 | Walsh, Jr. et al. |
| 7,873,085 B2 | 1/2011 | Babushkin et al. |
| 7,883,535 B2 | 2/2011 | Cantin et al. |
| 7,883,536 B1 | 2/2011 | Bendett et al. |
| 7,894,905 B2 | 2/2011 | Pless et al. |
| 7,899,512 B2 | 3/2011 | Labadie et al. |
| 7,914,842 B1 | 3/2011 | Greenberg et al. |
| 7,951,181 B2 | 5/2011 | Mahadevan-Jansen et al. |
| 7,988,688 B2 | 8/2011 | Webb et al. |
| 8,012,189 B1 | 9/2011 | Webb et al. |
| 8,160,696 B2 | 4/2012 | Bendett et al. |
| 8,355,793 B2 | 1/2013 | Dadd et al. |
| 8,396,570 B2 | 3/2013 | Dadd et al. |
| 2001/0021287 A1 | 9/2001 | Jewell et al. |
| 2002/0002391 A1 | 1/2002 | Gerdes |
| 2002/0123781 A1 | 9/2002 | Shanks et al. |
| 2002/0147400 A1 | 10/2002 | Chance |
| 2003/0083724 A1 | 5/2003 | Jog et al. |
| 2003/0165171 A1 | 9/2003 | Jewell |
| 2003/0236458 A1 | 12/2003 | Hochman |
| 2004/0073101 A1 | 4/2004 | Chance |
| 2004/0116985 A1 | 6/2004 | Black |
| 2004/0225339 A1 | 11/2004 | Yaroslavsky et al. |
| 2004/0243111 A1 | 12/2004 | Bendett et al. |
| 2004/0243112 A1 | 12/2004 | Bendett et al. |
| 2005/0065531 A1 | 3/2005 | Cohen |
| 2005/0096720 A1 | 5/2005 | Sharma et al. |
| 2005/0099824 A1 | 5/2005 | Dowling et al. |
| 2005/0142344 A1 | 6/2005 | Toepel |
| 2005/0143789 A1 | 6/2005 | Whitehurst et al. |
| 2005/0169597 A1 | 8/2005 | Colgan et al. |
| 2005/0216072 A1 | 9/2005 | Mahadevan-Jansen et al. |
| 2005/0228256 A1 | 10/2005 | Labadie et al. |
| 2006/0095105 A1 | 5/2006 | Jog et al. |
| 2006/0129210 A1 | 6/2006 | Cantin et al. |
| 2006/0149337 A1 | 7/2006 | John |
| 2006/0161218 A1 | 7/2006 | Danilov |
| 2006/0161227 A1 | 7/2006 | Walsh et al. |
| 2006/0167564 A1 | 7/2006 | Flaherty et al. |
| 2006/0276861 A1 | 12/2006 | Lin |
| 2007/0036493 A1 | 2/2007 | Brenner et al. |
| 2007/0053996 A1 | 3/2007 | Boyden et al. |
| 2007/0054319 A1 | 3/2007 | Boyden et al. |
| 2007/0060983 A1 | 3/2007 | Merfeld |
| 2007/0060984 A1 | 3/2007 | Webb et al. |
| 2007/0142874 A1 | 6/2007 | John |
| 2007/0179557 A1 | 8/2007 | Maschino et al. |
| 2007/0191906 A1 | 8/2007 | Iyer et al. |
| 2007/0260297 A1 | 11/2007 | Chariff |
| 2007/0261127 A1 | 11/2007 | Boyden et al. |
| 2008/0009748 A1 | 1/2008 | Gratton et al. |
| 2008/0077198 A1 | 3/2008 | Webb et al. |
| 2008/0077200 A1 | 3/2008 | Bendett et al. |
| 2008/0086206 A1 | 4/2008 | Nasiatka et al. |
| 2008/0140149 A1 | 6/2008 | John et al. |
| 2008/0161697 A1 | 7/2008 | Chance |
| 2008/0183247 A1 | 7/2008 | Harding |
| 2008/0221640 A1 | 9/2008 | Overstreet et al. |
| 2008/0299201 A1 | 12/2008 | Kozloski et al. |
| 2008/0306576 A1 | 12/2008 | Boyden et al. |
| 2009/0030327 A1 | 1/2009 | Chance |
| 2009/0054954 A1 | 2/2009 | Foley |
| 2009/0062685 A1* | 3/2009 | Bergethon et al. ............ 600/554 |
| 2009/0076115 A1 | 3/2009 | Wharton et al. |
| 2009/0099441 A1 | 4/2009 | Giszter et al. |
| 2009/0163982 A1 | 6/2009 | DeCharms |
| 2009/0177247 A1 | 7/2009 | Neal et al. |
| 2009/0177255 A1 | 7/2009 | Merfeld |
| 2009/0210039 A1 | 8/2009 | Boyden et al. |
| 2010/0016732 A1 | 1/2010 | Wells et al. |
| 2010/0049180 A1 | 2/2010 | Wells et al. |
| 2010/0114190 A1 | 5/2010 | Bendett et al. |
| 2010/0145418 A1 | 6/2010 | Zhang et al. |
| 2010/0162109 A1 | 6/2010 | Chatterjee et al. |
| 2010/0174329 A1* | 7/2010 | Dadd et al. ............ 607/3 |
| 2010/0174330 A1 | 7/2010 | Dadd et al. |
| 2010/0184818 A1 | 7/2010 | Wharton et al. |
| 2010/0191079 A1 | 7/2010 | Shoureshi et al. |
| 2010/0191308 A1 | 7/2010 | Meister |
| 2010/0197995 A1 | 8/2010 | Wenzel et al. |
| 2010/0198317 A1 | 8/2010 | Lenarz et al. |
| 2010/0262212 A1 | 10/2010 | Shoham et al. |
| 2010/0292758 A1 | 11/2010 | Lee et al. |
| 2011/0172680 A1 | 7/2011 | Younge et al. |
| 2011/0172725 A1 | 7/2011 | Wells et al. |
| 2011/0295331 A1 | 12/2011 | Wells et al. |
| 2012/0197374 A1 | 8/2012 | Vogt et al. |

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

Arridge, et al., "The theoretical basis for the determination of optical pathlengths in tissue: temporal and frequency analysis", "Phys. Med. Biol.", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science", Oct. 1, 1999, pp. 110-113, vol. 286.

Eder, Matthias, et al., "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

(56) References Cited

OTHER PUBLICATIONS

Haggard, "The Sources of Human Volition", "SCIENCE", May 8, 2009, pp. 731-733, vol. 324.

Han, Xue, et al., "Multiple-Color Optical Activation, Silencing, and Desynchronization of Neural Activity, with Single-Spike Temporal Resol", "PLoS One 2(3): e299. doi:10.1371/journal.pone.0000299", Mar. 2007, p. e299, No. 3, Publisher: www.plosone.org.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, p. 021008, vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004, pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005, p. 064036, vol. 10, No. 6.

Princeton Lightwave (Company), "High Power Multimode Laser Arrays", "www.princetonlightwave.com/content/pli_high_power_multimode_laser_arrays.pdf", 2005.

Princeton Lightwave (Company), "High Power Water Cooled Laser Stack", "www.princetonlightwave.com", 2005.

Princeton Lightwave (Company), "High Power Water Cooled Laser Stack", "http://www.princetonlightwave.com/content/pli_high_power_multimode_laser_stacks.pdf", 2005 (downloaded 12-.

Princeton Lightwave (Company), "High Power Single Element Laser", "www.princetonlightwave.com/content/HP%20Single%20Element%20Laser%20version%202.pdf", 2005.

Rolfe, "In Vivo Near-Infrared Spectroscopy", "Annu. Rev. Biomed. Eng.", 2000, pp. 715-754, vol. 2.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine", 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al., "Channelrhodopsin-2 and optical control of excitable cells", "Nature Methods", Sep. 21, 2006, pp. 785-792, vol. 3, No. 10.

Hibbs-Brenner, et al., "Hibbs-Brenner, et al.—VCSEL Technology for Medical Diagnostics and Therapeutics", "Proc. of SPIE", 2009, pp. 1-10, vol. 7180.

Izzo, et al., "Laser stimulation of auditory neurons: effect of shorter pulse duration and penetration depth", "Biophysical Journal", Apr. 2008, pp. 3159-3166, vol. 94.

Littlefield, Philip D., et al., "Laser Stimulation of Single Auditory Nerve Fibers", "Laryngoscope", Oct. 2010, pp. 2071-2082, vol. 120.

\* cited by examiner

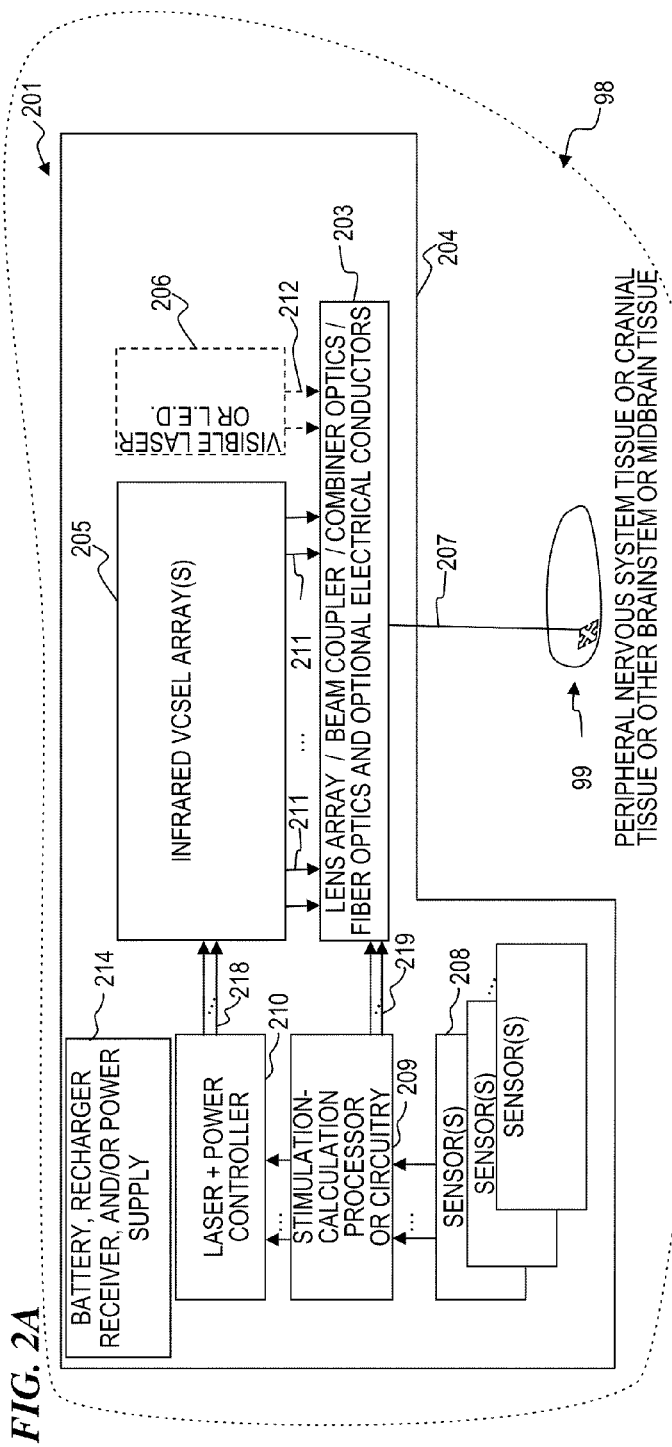
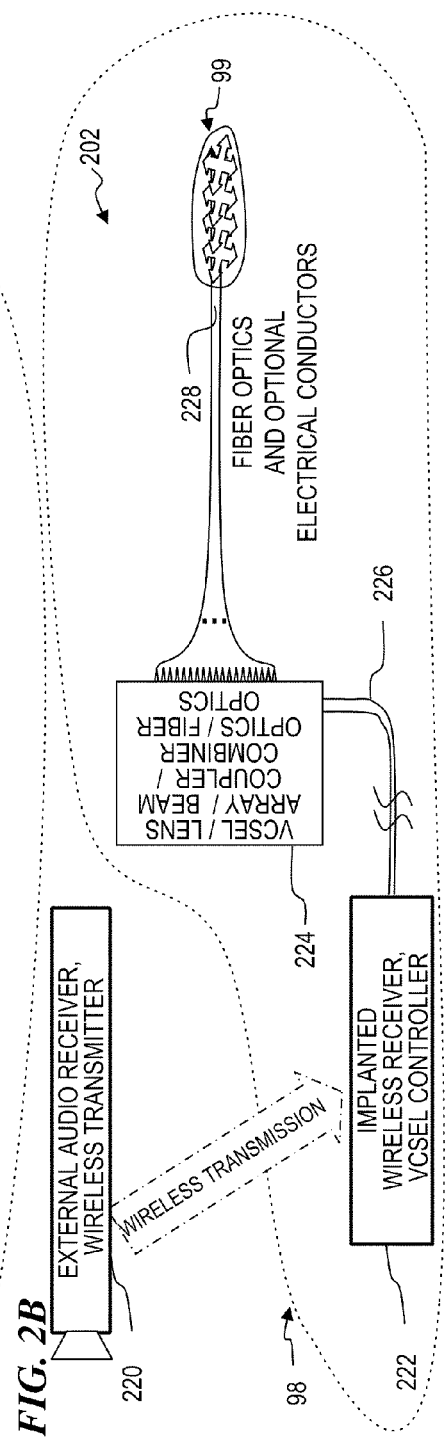
FIG. 2A
FIG. 2B

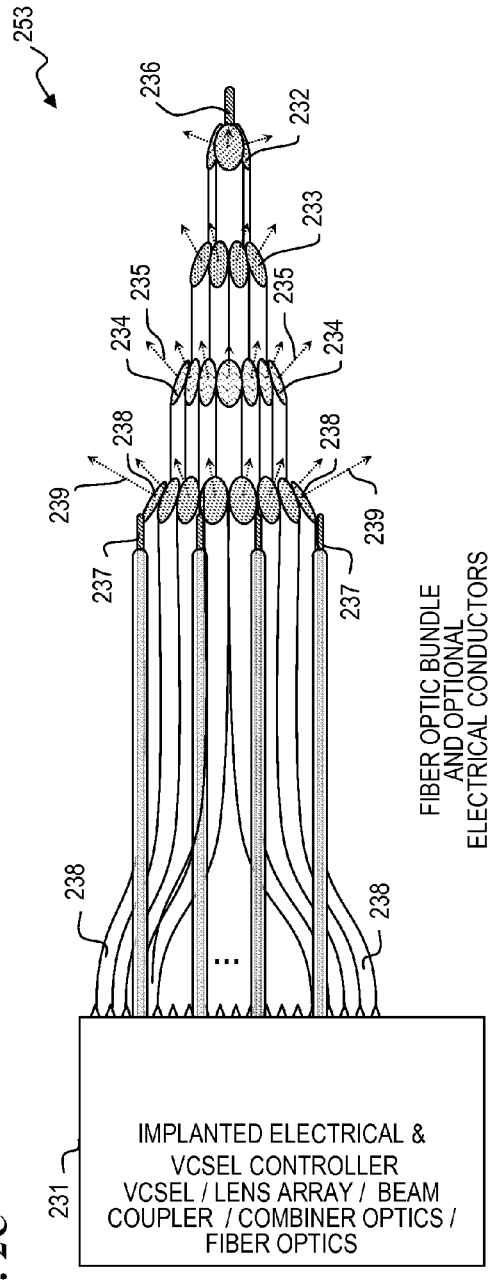

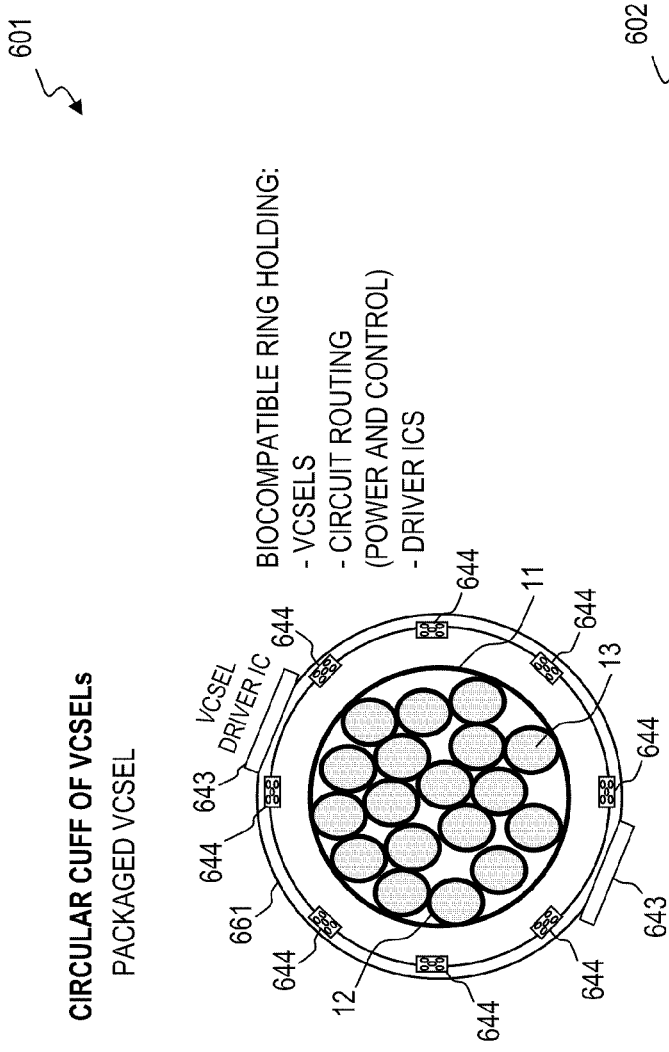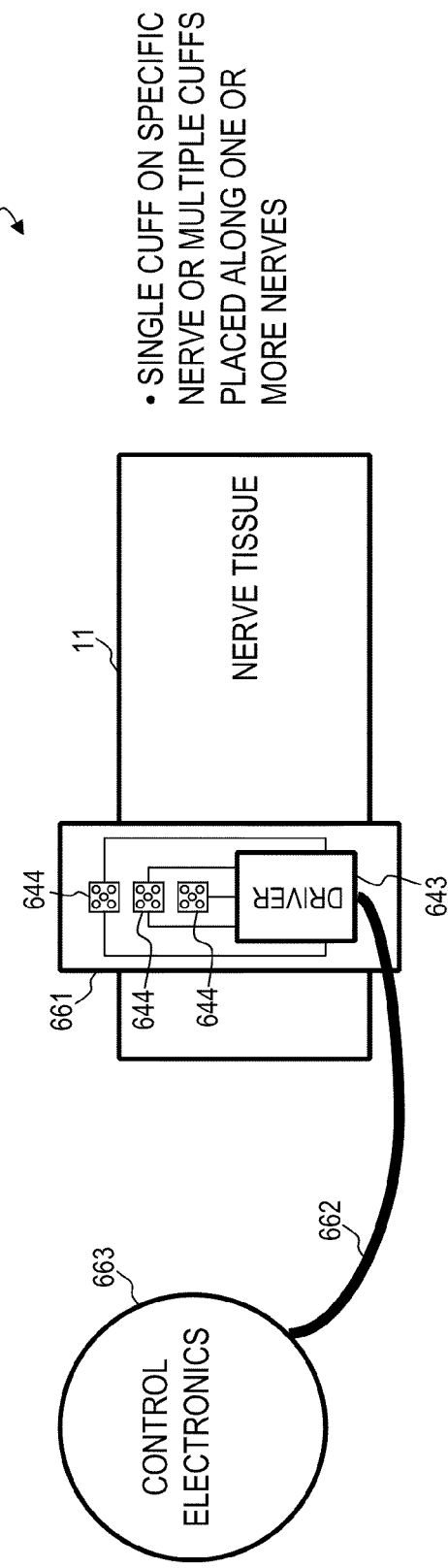
FIG. 6A
FIG. 6B

Multiple wavelengths with gratings (WDM)

GRATINGS PLACED IN EITHER CIRCULAR OR SPIRAL CUFF FORMATION
GRATINGS PLACED SUCH THAT DIFFERENT WAVELENGTHS EMITTED FROM WAVEGUIDE AT EITHER DIFFERENT AXIAL OR TRANSVERSE LOCATIONS AS FUNCTION OF WAVELENGTH (DEMONSTRATED BY THE 2 DIFF. FIGURES)

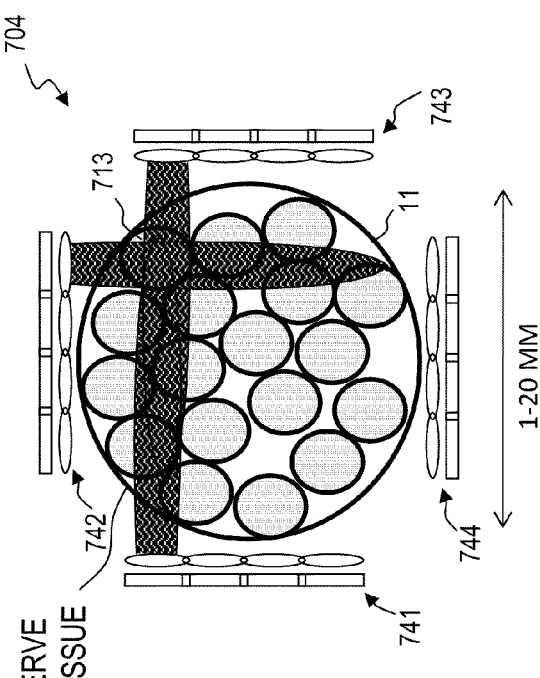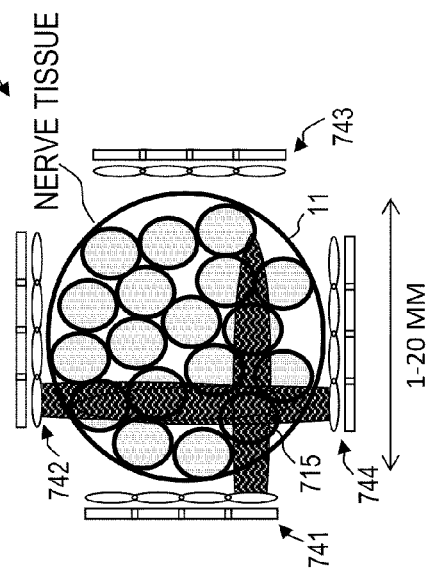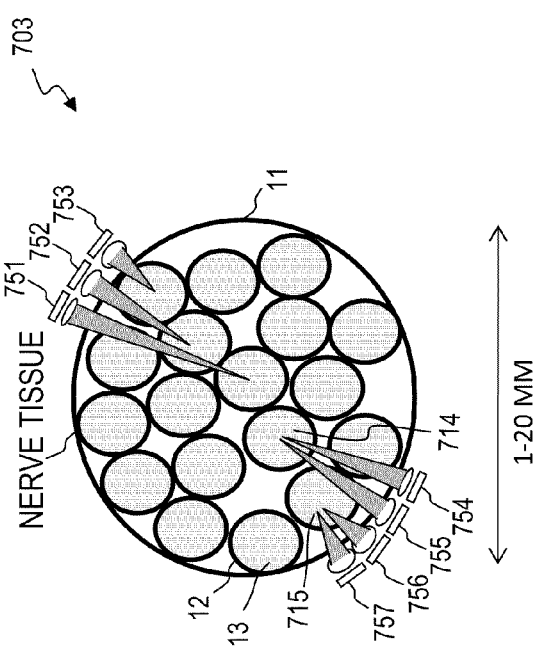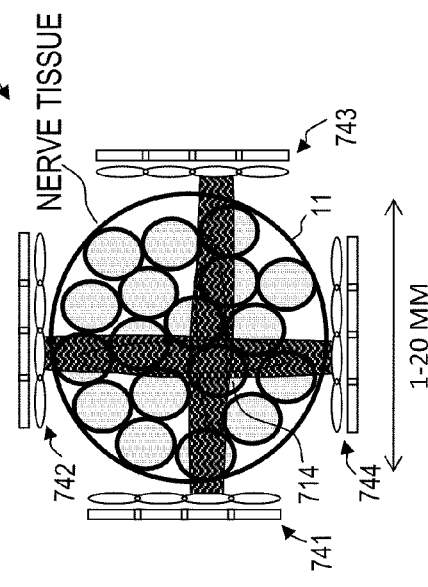

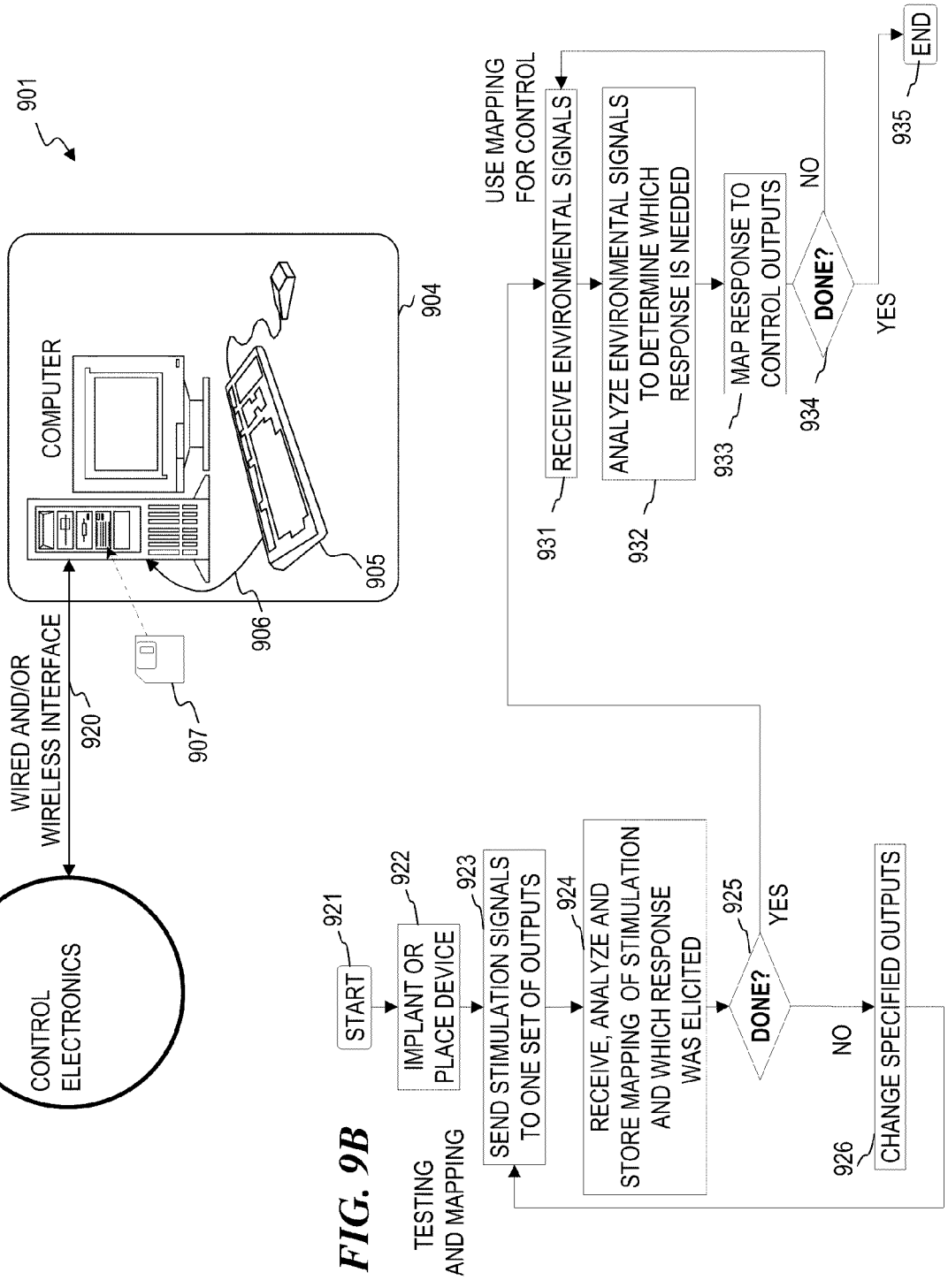

CUFF APPARATUS AND METHOD FOR OPTICAL AND/OR ELECTRICAL NERVE STIMULATION OF PERIPHERAL NERVES

CROSS-REFERENCE TO RELATED APPLICATIONS

This invention claims benefit under 35 U.S.C. §119(e) of U.S. Provisional Patent Application No. 61/349,810 filed May 28, 2010, by Jonathon D. Wells et al., titled "Implantable Infrared Nerve Stimulation Devices for Peripheral and Cranial Nerve Interfaces";
U.S. Provisional Patent Application No. 61/349,813 filed May 28, 2010, by Jonathon D. Wells et al., titled "Laser-Based Nerve Stimulators for, e.g., Hearing Restoration in Cochlear Prostheses";
U.S. Provisional Patent Application No. 61/381,933 filed Sep. 10, 2010, by Jonathon D. Wells et al., titled "Laser-Based Nerve Stimulators for, e.g., Hearing Restoration in Cochlear Prostheses"; and
U.S. Provisional Patent Application No. 61/386,461 filed Sep. 24, 2010, by Jonathon D. Wells et al., titled "Implantable Infrared Nerve Stimulation Devices for Peripheral and Cranial Nerve Interfaces";
each of which is incorporated herein by reference in its entirety.

RELATED APPLICATIONS

The present invention is related to the following prior applications and patents:
U.S. Provisional Patent Application No. 60/715,884 filed Sep. 9, 2005, titled "Apparatus and Method for Optical Stimulation of Nerves";
U.S. Provisional Patent Application No. 60/826,538 filed Sep. 21, 2006, titled "Miniature Apparatus and Method for Optical Stimulation of Nerves and Other Animal Tissue";
U.S. Provisional Patent Application No. 60/872,930 filed Dec. 4, 2006, titled "Apparatus and Method for Characterizing Optical Sources used with Human and Animal Tissues";
U.S. Provisional Patent Application No. 60/884,619 filed Jan. 11, 2007, titled "Vestibular Implant Using Infrared Nerve Stimulation";
U.S. Provisional Patent Application No. 60/885,879 filed Jan. 19, 2007, titled "Hybrid Optical-Electrical Probes";
U.S. Provisional Patent Application No. 60/964,634 filed Aug. 13, 2007, titled "VCSEL Array Stimulator Apparatus and Method for Light Stimulation of Bodily Tissues";
U.S. Provisional Patent Application No. 61/015,665 filed Dec. 20, 2007, titled "Laser Stimulation of the Auditory System at 1.94 µm and Microsecond Pulse Durations"
U.S. Provisional Patent Application No. 61/081,732 filed Jul. 17, 2008, titled "Method and Apparatus for Neural Signal Capture to Drive Neuroprostheses or Bodily Function";
U.S. Provisional Patent Application No. 61/102,811 filed Oct. 3, 2008, titled "Nerve Stimulator and Method using Simultaneous Electrical and Optical Signals";
U.S. Provisional Patent Application No. 61/147,073 filed Jan. 23, 2009, titled "Optical Stimulation Using Infrared Lasers (or In Combination with Electrical Stimulation) of the Auditory Brainstem and/or Midbrain";
U.S. patent application Ser. No. 11/257,793 filed Oct. 24, 2005, titled "Apparatus for Optical Stimulation of Nerves and Other Animal Tissue" (now U.S. Pat. No. 7,736,382 issued Jun. 15, 2010);
U.S. patent application Ser. No. 11/536,639 filed Sep. 28, 2006, titled "Miniature Apparatus and Method for Optical Stimulation of Nerves and Other Animal Tissue";
U.S. patent application Ser. No. 11/948,912 filed Nov. 30, 2007, titled "Apparatus and Method for Characterizing Optical Sources Used with Human and Animal Tissues";
U.S. patent application Ser. No. 11/536,642 filed Sep. 28, 2006, titled "Apparatus and Method for Stimulation of Nerves and Automated Control of Surgical Instruments";
U.S. patent application Ser. No. 11/971,874 filed Jan. 9, 2008, titled "Method and Vestibular Implant using Optical Stimulation of Nerves";
U.S. patent application Ser. No. 12/018,185 filed Jan. 22, 2008, titled "Hybrid Optical-Electrical Probes" (now U.S. Pat. 7,883,536 issued Feb. 8, 2011);
U.S. patent application Ser. No. 12/191,301 filed Aug. 13, 2008, titled "VCSEL Array Stimulator Apparatus and Method for Light Stimulation of Bodily Tissues";
U.S. patent application Ser. No. 12/505,462 filed Jul. 17, 2009, titled "Apparatus and Method for Neural-Signal Capture to Drive Neuroprostheses or Control Bodily Function";
U.S. patent application Ser. No. 12/573,848 filed Oct. 5, 2009, titled "Nerve Stimulator and Method using Simultaneous Electrical and Optical Signals";
U.S. patent application Ser. No. 12/693,427 filed Jan. 25, 2010, titled "Optical Stimulation of the Brainstem and/or Midbrain, including Auditory Areas";
U.S. patent application Ser. No. 12/890,602 filed Sep. 24, 2010 by Jonathon D. Wells et al., titled "Laser-Based Nerve Stimulators for, e.g., Hearing Restoration in Cochlear Prostheses";
U.S. patent application Ser. No. 13/117,121 filed May 26, 2011 by Jonathon D. Wells et al., titled "IMPLANTABLE INFRARED NERVE STIMULATION DEVICES FOR PERIPHERAL AND CRANIAL NERVE INTERFACES";
U.S. patent application Ser. No. 13/117,118 filed May 26, 2011 by Jonathon D. Wells et al., titled "Optical Bundle Apparatus and Method for Optical and/or Electrical Nerve Stimulation of Peripheral Nerves"; and
U.S. patent application Ser. No. 13/117,125 filed May 26, 2011 by Jonathon D. Wells et al., titled "Nerve-Penetrating Apparatus and Method for Optical and/or Electrical Nerve Stimulation of Peripheral Nerves";
each of which is incorporated herein by reference in its entirety.

FIELD OF THE INVENTION

The present invention relates to laser stimulation of animal tissues and more particularly to lasers and methods for making and using devices that generate optical signals, and optionally also electrical signals in combination with one or more such optical signals, to stimulate (i.e., trigger) and/or simulate a sensory-nerve signal in nerve and/or brain tissue of a living animal (e.g., a human), for example to treat nerve damage in the peripheral nervous system (PNS) or the central nervous system (CNS) and provide sensations to stimulate and/or simulate "sensory" signals in nerves and/or brain tissue of a living animal (e.g., a human) to treat other sensory deficiencies (e.g., touch, feel, balance, visual, taste, or olfactory) and provide sensations related to those sensory deficiencies, and/or to stimulate (i.e., trigger) and/or simulate a motor-nerve signal in nerve and/or brain tissue of a living animal (e.g., a human), for example to control a muscle or a robotic prosthesis.

BACKGROUND OF THE INVENTION

FIG. 1A is a schematic diagram 101 of a nerve (adapted from www.mayoclinic.org/peripheral-nerve-tumors-benign/diagnosis.html). A nerve 11 contains fascicles (bundles) 12 of individual nerve fibers 13 of neurons. FIG. 1B is a schematic diagram 102 of the structure of a spinal nerve 11 that includes its surrounding epineurium 14, which includes connective tissue and blood vessels 15, one or more fascicles (fasciculus) 12, each of which is surrounded by perineurium 17. Within a fascicle 12 is a plurality of axons 13 each having a myelin sheath surrounded by endoneurium tissue 18 (credit to internet sources-data obtained from: en.wikipedia.org/wiki/Nerve_fascicle and trc.ucdavis.edu/mjguinan/apc100/modules/nervous/pns/nerve1/nerve1.html (URL no longer active)).

Typically a nerve action potential (NAP) or compound nerve action potential (CNAP), which is a summated potential of the action potentials in all the axons in a nerve, as a signal travels down a nerve, is sensed using an electrical sensor probe that detects the waveform of a voltage associated with the NAP. Accordingly, traditional methods used electrical stimulation to trigger a NAP signal in a nerve. One disadvantage of using electrical stimulation is that the electrical signal applied to stimulate one nerve fiber will generally stimulate a plurality of surrounding nerve fibers (even nerve fibers in other fascicles than the fascicle containing the nerve of interest) to also trigger NAP signals in those other nerve fibers: Present conventional neuromodulation technology is based on the generation of electric fields around the neuron. The spatial differential voltage along the axons, commonly referred to as the driving function, results in a depolarization of the neural membrane. This depolarization results in action-potential generation, which is then transmitted to target organ where it produces a characteristic effect. The electric field is significantly influenced by the electrical impedance of the tissues.

Extraneural electrodes, such as the Flat Interface Nerve Electrode (FINE), have demonstrated fascicular selectivity (to within about 400 µm). The perineurium, which surrounds a plurality of nerve axons and defines the individual fascicle, typically has a high impedance. This causes the voltage distribution to be fairly uniform within at least a portion of a fascicle (while also being electrically isolated from neighboring fascicles), hence limiting the possibility of sub-fascicular selectivity when using electrical stimulation. While the spatial selectivity of these extraneural electrodes (such as the FINE) has been successfully shown to produce functional neural stimulation in clinical applications, neuromodulation applications such as hand-grasp, sensory-stimulation applications for artificial prostheses, and control of autonomic functions such as cardiac rate via Vagus-nerve stimulation, require, in some cases, selection of at most one fascicle and even greater sub-fascicular spatial selectivity (i.e., selection of a single axon or just a few axons but not all the axons in the single fascicle) than is typically possible using electrical stimulation alone, such that separate signals are delivered to different axons within one fascicle.

As a convention used herein, a nerve will be defined as a collection of individual nerve fibers (i.e., axons) of individual nerve cells (neurons) that together form a set of nerve pathways (an integrated set of pathways for signal propagation within the nervous system). Subsets of the individual nerve fibers are each bundled into one of a plurality of fascicles that together form the nerve. Action potentials can occur in the axon portion of individual nerve cells. A series of individual nerve fibers that together form an integrated signal pathway starting at a sensory-receptor nerve ending and extending to the brain will be referred to as a sensory-nerve pathway, while a series of individual nerve fibers that together form an integrated signal pathway starting at the brain and extending to a muscle cell will be referred to as a motor-nerve pathway. A sensory-nerve pathway that carries auditory signals will be referred to as an auditory-nerve pathway, and a sensory-nerve pathway that carries signals from the sense-of-balance organs (e.g., the vestibular organs of the inner ear, or perhaps the eyes) will be referred to as a sense-of-balance nerve pathway. A sensory-nerve pathway that carries olfactory signals will be referred to as an olfactory-nerve pathway, a sensory-nerve pathway that carries taste signals will be referred to as a taste-nerve pathway, and a sensory-nerve pathway that carries tactician signals will be referred to as a tactile-nerve pathway.

Within each fascicle of a nerve, there will typically be a plurality of sensory-nerve pathways and a plurality of motor-nerve pathways, wherein the number of sensory-nerve pathways will typically be about fifteen times as many as the number of motor-nerve pathways. As well, a series of individual nerve fibers may together form an integrated pathway starting at one of various internal organs and ending in the brain, with then other series of individual nerve fibers together forming an integrated pathway starting at the brain and extending to some internal end organ (such as the digestive tract, the heart, or blood vessels) as part of the autonomic nervous system; and a series of individual nerve fibers may together form an integrated pathway within the brain referred to as a tract. As used herein, a nerve bundle or fascicle refers to a collection of nerve fibers that subserve a common or similar function (e.g., a fascicle may support a plurality of different motor-nerve pathways and thus motor-control signals needed for the muscles for a hand grasp, for example; similarly the same and/or a nearby fascicle may support a plurality of corresponding sensory-nerve pathways and thus sensory signals that provide the brain with feedback for the hand grasp).

U.S. patent application Ser. No. 12/018,185 filed Jan. 22, 2008 by Mark P. Bendett and James S. Webb, titled "Hybrid Optical-Electrical Probes" (now U.S. Pat. No. 7,883,536 issued Feb. 8, 2011), which is incorporated herein by reference in its entirety, describes an optical-signal vestibular-nerve stimulation device and method that provides different nerve stimulation signals to a plurality of different vestibular nerves, including at least some of the three semicircular canal nerves and the two otolith organ nerves. In some embodiments described in that patent application, balance conditions of the person are sensed by the implanted device, and based on the sensed balance conditions, varying infrared (IR) nerve-stimulation signals are sent to a plurality of the different vestibular nerves. Also described is a method that includes obtaining light from an optical source; transmitting the light through an optical fiber between a tissue of an animal and an optical transducer, and detecting electrical signals using conductors attached to the optical fiber. The application also describes an apparatus that includes an optical source, an optical transmission medium operatively coupled to the optical source and configured to transmit light from the optical source to respective nerves of each of one or more organs of an animal, an electrical amplifier, and an electrical transmission medium integral with the optical transmission medium and operatively coupled to the electrical amplifier, wherein the electrical transmission medium is configured to transmit an electrical signal from the respective nerves to the electrical amplifier.

U.S. Pat. No. 6,921,413 issued Jul. 26, 2005 to Mahadevan-Jansen et al., titled "Methods and devices for optical stimulation of neural tissues," and U.S. patent application Ser. No. 11/257,793 filed Oct. 24, 2005 by Webb et al. (now U.S. Pat. No. 7,736,382, which issued Jun. 15, 2010), titled "Apparatus for Optical Stimulation of Nerves and Other Animal Tissue," are each incorporated herein by reference in their entirety. Both of these describe optical stimulation of nerves in general.

U.S. Patent Application Publication No. US 2006/0161227, of Walsh et al., titled "Apparatus and Methods for Optical Stimulation of the Auditory Nerve," is incorporated herein by reference in its entirety. This application describes a cochlear implant placed in a cochlea of a living subject for stimulating the auditory system of the living subject, where the auditory system comprises auditory neurons. In one embodiment, the cochlear implant includes a plurality of light sources $\{L_i\}$, placeable distal to the cochlea, each light source being operable independently and adapted for generating an optical energy, $E_i$, wherein i=1, . . . , N, and N is the number of the light sources, and delivering means placeable in the cochlea and optically coupled to the plurality of light sources, $\{L_i\}$, such that in operation, the optical energies $\{E_i\}$ generated by the plurality of light sources $\{L_i\}$ are delivered to target sites, $\{G_i\}$, of auditory neurons, respectively, wherein the target sites $G_1$ and $G_N$ of auditory neurons are substantially proximate to the apical end and the basal end of the cochlea, respectively.

U.S. Patent Application Publication No. US 2005/0004627 titled "Auditory midbrain implant" filed by Peter Gibson et al. on Aug. 26, 2004, is incorporated herein by reference (this application issued as U.S. Pat. No. 7,797,029 on Sep. 14, 2010). This application describes an electrode array that is implantable within the inferior colliculus of the midbrain and/or other appropriate regions of the brain of an implantee and adapted to provide electrical stimulation thereto. The electrode array includes an elongate member having a plurality of electrodes mounted thereon in a longitudinal array. A delivery cannula for delivering the electrode array comprised of two half-pipes is also described.

U.S. Patent Application No. US 2007/0261127 A1 filed Jul. 24, 2006, by Edward S. Boyden and Karl Deisseroth, titled "Light-Activated Cation Channel and Uses Thereof"; U.S. Patent Application No. US 2007/0054319 A1 filed Jul. 24, 2006, by Edward S. Boyden and Karl Deisseroth, titled "Light-Activated Cation Channel and Uses Thereof"; and U.S. Patent Application No. US 2007/0053996 A1 (now abandoned) filed Jul. 24, 2006, by Edward S. Boyden and Karl Deisseroth, titled "Light-Activated Cation Channel and Uses Thereof" are all incorporated herein by reference. These describe compositions and methods for light-activated cation channel proteins and their uses within cell membranes and subcellular regions. They describe proteins, nucleic acids, vectors and methods for genetically targeted expression of light-activated cation channels to specific cells or defined cell populations. In particular the descriptions describe millisecond-timescale temporal control of cation channels using moderate light intensities in cells, cell lines, transgenic animals, and humans. The descriptions provide for optically generating electrical spikes in nerve cells and other excitable cells useful for driving neuronal networks, drug screening, and therapy.

An article authored by Han, Xue, et al. titled "*Multiple-Color Optical Activation, Silencing, and Desynchronization of Neural Activity, with Single-Spike Temporal Resolution*" (PLoS ONE 2(3): e299. doi:10.1371/journal.pone.0000299, March 2007) is incorporated herein by reference. This article describes targeting the codon-optimized form of the light-driven chloride pump halorhodopsin from the archaebacterium *Natronomas pharaonis* (hereafter abbreviated Halo) to genetically-specified neurons enables them to be silenced reliably, and reversibly, by millisecond-timescale pulses of yellow light. The article describes that trains of yellow and blue light pulses can drive high-fidelity sequences of hyperpolarizations and depolarizations in neurons simultaneously expressing yellow light-driven Halo and blue light-driven ChR2, allowing for the first time manipulations of neural synchrony without perturbation of other parameters such as spiking rates. The article further describes the Halo/ChR2 system thus constitutes a powerful toolbox for multichannel photoinhibition and photostimulation of virally or transgenically targeted neural circuits without need for exogenous chemicals, thus enabling systematic analysis and engineering of the brain, and quantitative bioengineering of excitable cells.

An article authored by Bernstein, Jacob G., et al. titled "*Prosthetic systems for therapeutic optical activation and silencing of genetically-targeted neurons*" (Proc Soc Photo Opt Instrum Eng.; 6854: 68540H., May 5, 2008) is incorporated herein by reference. This article describes that the naturally-occurring light-activated proteins channelrhodopsin-2 (ChR2) and halorhodopsin (Halo/NpHR) can, when genetically expressed in neurons, enable them to be safely, precisely, and reversibly activated and silenced by pulses of blue and yellow light, respectively. The article describes the ability to make specific neurons in the brain light-sensitive, using a viral approach. The article also describes the design and construction of a scalable, fully implantable optical prosthetic capable of delivering light of appropriate intensity and wavelength to targeted neurons at arbitrary 3-D locations within the brain, enabling activation and silencing of specific neuron types at multiple locations. The article further describes control of neural activity in the cortex of the non-human primate, a key step in the translation of such technology for human clinical use. The article asserts systems for optical targeting of specific neural circuit elements may enable a new generation of high-precision therapies for brain disorders.

U.S. Patent Application No. US 2009/0210039 A1 filed Jan. 16, 2009, by Edward S. Boyden et al., titled "Prosthetic Systems for Therapeutic Optical Activation and Silencing of Genetically-Targeted Neurons," is incorporated herein by reference. The application describes an optical prosthesis that permits control of neural circuits that comprises a probe having a set of light sources, drive circuit connections connected to each light source, a housing surrounding the light sources and drive circuit connections, and drive circuitry for driving and controlling the probe. The application also describes drive circuit connections and drive circuitry may optionally provide for wireless communication. The application describes light sources may be light-emitting diodes, lasers, or other suitable sources. The application describes the device may optionally include sensors for monitoring the target cells. The application also describes a multi-dimensional array of probes, each probe having a set of light sources, drive circuit connections connected to each light source, a housing surrounding the light sources and the drive circuit connections, drive circuitry for driving and controlling the probes, and supporting hardware that holds the probes in position with respect to each other and the target cells.

There are patients suffering from incomplete spinal cord injuries that do not result in complete loss of movement and sensation below the injury site. Injuries resulting from an anterior spinal cord injury that include damage to the front of the spinal cord affect pain, temperature, and touch sensation, but leave some pressure and joint sensation, and wherein often motor function is unaffected.

Injuries to the central portion of the spinal cord can result in Central Cord Syndrome and form an incomplete spinal cord injury in which some of the signals from the brain to the body are not received, characterized by impairment in the arms and hands and, to a lesser extent, in the legs. In some injuries, sensory loss below the site of the spinal injury and loss of bladder control may occur. Central Cord Syndrome, which is usually the result of trauma, is associated with damage to the large nerve fibers that carry information directly from the cerebral cortex of the brain to the spinal cord and these large nerves are particularly important for hand and arm function. Symptoms of large nerve fiber damage may include paralysis and/or loss of fine control of movements in the arms and hands, with relatively less impairment of leg movements. Often, the brain's ability to send and receive signals to and from parts of the body below the site of trauma is affected but not entirely blocked.

Spinal injuries caused by a lesion affecting the lateral half of the spinal cord is known as Brown-Séquard syndrome, and is characterized by contralateral hemisensory anesthesia to pain and temperature, ipsilateral loss of propioception, and ipsilateral motor paralysis below the level of the lesion. Tactile sensation is generally spared.

The most common type of spinal cord injury is a spinal contusion wherein the spinal cord is bruised but not severed. The spinal contusion results in inflammation and bleeding in the spinal column near the site of the injury which can kill spinal cord neurons. Finally, injuries to individual nerve cells manifest as a loss of sensory and motor functions in the area of the body to which the injured nerve root corresponds.

Besides such spinal-cord injuries, there are numerous other nerve injuries and pathologies that need treatment. Thus, there is a need to provide therapy (e.g., through stimulation of physiological signals in the patient such as nerve action potentials (NAPs)) that restores such sensations (signals towards the brain) to persons having such injuries, as well as nerve stimulation and/or inhibition for treatment of pain, obesity, epilepsy, depression, and the like. There is also a need to provide therapy that restores motor-nerve (muscle-control) signals from the brain towards muscles or prostheses (through NAP stimulation, inhibition, or both), for motor control as well as treatment of incontinence, irregular heart rhythms, tremors or twitches, and the like.

There is also a need for efficacious apparatus and methods for optically stimulating, and/or optically and electrically stimulating, nerves of the central nervous system (CNS) and/or the peripheral nervous system (PNS) in a living animal in order to generate a nerve action potential (NAP) in one neuron (nerve cell), or in multiple neurons within a nerve bundle or nerve (where the combined individual NAPs form a compound nerve action potential, or CNAP), or similar physiological response in the animal. Optical and/or electrical-and-optical stimulation of neurons can provide more precision in terms of stimulating a particular nerve pathway than is possible using only electrical stimulation.

BRIEF SUMMARY OF THE INVENTION

The present invention provides an apparatus and a method for optically, or optically and electrically, stimulating neurons (e.g., sensory and/or motor neurons) in the peripheral nervous system (PNS), and or the central nervous system (CNS) (including the spinal cord and/or brainstem and/or midbrain and/or brain tissue of a living animal) to obtain a physiological response in the animal (e.g., a sense of touch, taste, smell, sight or sound). In some embodiments, the simultaneous application of both an optical stimulation signal and an electrical stimulation signal provides more efficacious generation of NAP responses in the animal than either optical or electrical stimulation alone. In addition, the much higher precision possible when using optical stimulation permits many more channels of auditory nerve pathways to be individually and distinctly stimulated than is possible using electrical stimulation alone. In some embodiments, the application of an electrical field before or during the application of the optical stimulation pulse permits more reliable generation of nerve-action-potential signals than is possible using the optical signal pulse alone, and permits reliable generation of NAP signals.

One purpose of the present peripheral nervous system (PNS) and/or the central nervous system (CNS) optical stimulator or hybrid stimulator (wherein the hybrid stimulator uses both optical and electrical stimulation) is to provide sensory sensations and/or motor responses for patients who have sensory neuron or motor neuron impairment. Another use of some embodiments of the present invention is to provide an apparatus and method for conducting basic and clinical research on how to improve the performance of PNS and CNS neural implants using infrared laser technology, optionally also using simultaneous electrical stimulation. The optical PNS and CNS neural stimulator can also be used as a powerful research tool to stimulate discrete regions and neuronal populations without the concerns of shock artifact, a phenomenon that is inherent to electrical-stimulation paradigms.

In some embodiments, the present invention provides apparatus and methods for optical stimulation or optical-and-electrical stimulation of PNS and CNS neural pathways and/or brain tissue. In some embodiments of the present invention, radiant energy exposure of the PNS and CNS neural pathways using a mid-wavelength infrared laser generates optically-evoked sensory and/or motor neuron responses.

In other embodiments, the present invention provides apparatus and methods for optical stimulation or optical-and-electrical stimulation of nerve pathways and/or brain tissue of sensory modalities. In some such embodiments, apparatus and methods are provided for optical stimulation or optical-and-electrical stimulation of nerve pathways and/or brain tissue involved in vision. In other such embodiments, apparatus and methods are provided for optical- or optical-and-electrical stimulation of nerve pathways and/or brain tissue involved in olfaction. In other such embodiments, apparatus and methods are provided for optical- or optical-and-electrical stimulation of nerve pathways and/or brain tissue involved in balance. In other such embodiments, apparatus and methods are provided for optical- or optical-and-electrical stimulation of nerve pathways and/or brain tissue involved in tactile sense. In other such embodiments, apparatus and methods are provided for optical- or optical-and-electrical stimulation of nerve pathways and/or brain tissue involved in taste. In other such embodiments, apparatus and methods are provided for optical- or optical-and-electrical stimulation of nerve pathways and/or brain tissue involved in hearing. In other such embodiments, apparatus and methods are provided for optical- or optical-and-electrical stimulation of nerve pathways and/or brain tissue involved in proprioception. In other such embodiments, apparatus and methods are provided for optical- or optical-and-electrical stimulation of nerve pathways and/or brain tissue involved in temperature. In other such embodiments, apparatus and methods are provided for optical- or optical-and-electrical stimulation of nerve pathways and/or brain tissue involved in pain management. In some embodiments, apparatus and methods are provided for optical- or optical-and-electrical stimulation of combinations of two or more of the above-mentioned sensations.

In some embodiments, one or more of the apparatus as described in the related provisional patent applications, patent applications and/or patents incorporated by reference above (e.g., 60/715,884, 60/826,538, 60/872,930, 60/884, 619, 60/885,879, 60/964,634, 61/015,665, 61/102,811, 61/147,073, Ser. Nos. 11/257,793, 11/536,639, 11/948,912, 11/536,642, 11/971,874, 12/018,185, 12/191,301, 12/573, 848, and 12/693,427) are used to generate and/or deliver the optical-stimulation signals and optionally the electrical-stimulation signals that are delivered to the PNS and/or the CNS of the patient using methods and apparatus of the present invention. In some embodiments, the method of the present invention includes emitting a trigger amount of pulsed light and further includes applying a precharge current of electrical energy that is followed by the trigger amount of pulsed light intensity of the plurality of light signals.

BRIEF DESCRIPTION OF THE DRAWINGS

FIG. 2A is a block diagram of an implantable/partially implantable system 201.
FIG. 2B is a block diagram of a wireless-transmission partially implantable system 202.
FIG. 2C is a schematic side view of implantable fiber-optic bundle 253 with optional electrical conductors.
FIG. 2D is a schematic end view of implantable fiber-optic bundle 253 with optional electrical conductors.
FIG. 2E is a schematic side view of an embodiment of optical fiber 238 from the implantable fiber-optic bundle device 253 of FIG. 2C in an implanted configuration 250.
FIG. 2F is a schematic side view of an embodiment of optical fiber 238 from the implantable fiber-optic bundle device 253 of FIG. 2C in an implanted configuration 251.
FIG. 2G is a schematic side view of an embodiment of optical fiber 248 in an implanted configuration 252.
FIG. 2H is a schematic side view of an embodiment of an implantable fiber-optic bundle 258.
FIG. 6A is a cross-section end-view schematic representation of a circular cuff nerve stimulator 601, according to some embodiments of the present invention.
FIG. 6B is a side-view schematic representation of a circular cuff nerve stimulator 602, including control electronics, according to some embodiments of the present invention.

FIG. 7C is a cross-section end-view schematic representation of a multiple-focal-length nerve stimulator 703, according to some embodiments of the present invention.
FIGS. 7D1, 7D2, and 7D3 are cross-section end-view schematic representations of a multiple-intersection nerve stimulator 704, according to some embodiments of the present invention.
FIG. 9A is a block diagram of a computerized system 901 for determining a reaction of the nerve tissue through empirical testing of the light-emitting structure, power levels and/or electrical preconditioning.
FIG. 9B is a block diagram of a computerized method 902 for determining a reaction of the nerve tissue through empirical testing of the light-emitting structure, power levels and/or electrical preconditioning, and then using the mapping obtained from the testing to control a nerve stimulator.

DETAILED DESCRIPTION OF THE INVENTION

Figure 1B:
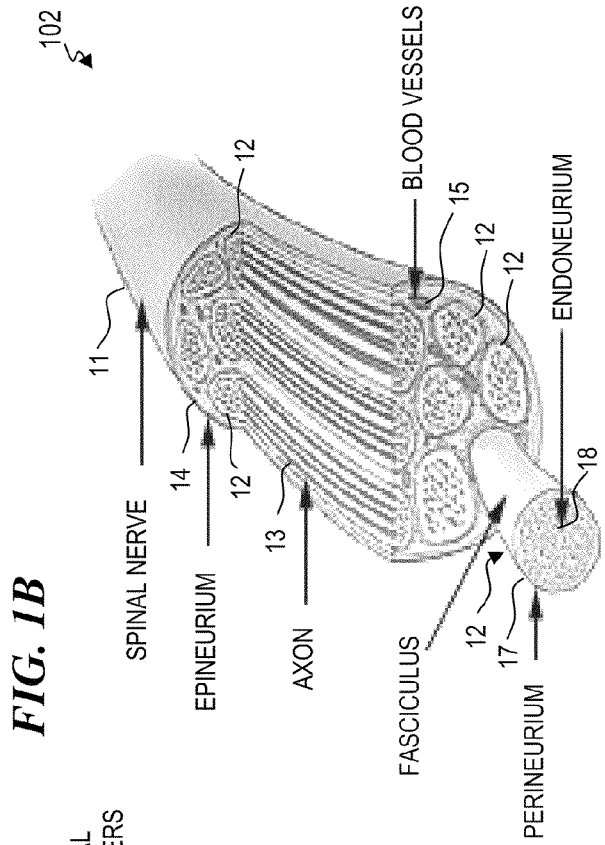
FIG. 1B is a schematic diagram 102 of a nerve 11.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon, the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Applying an electrical signal across or into a neuron (nerve cell), or a nerve bundle or nerve, is one way to stimulate a nerve action potential (NAP), either in a single neuron (nerve cell), or in a plurality of neurons within a nerve bundle, or within a nerve (the combined signals of NAPs in a nerve bundle or nerve are referred to as a compound nerve action potential (CNAP)). Applying an optical signal (e.g., a short relatively high-power pulse of infrared (IR) laser light, in some embodiments, for example at a signal wavelength about 1.9 microns, a signal wavelength of including the range of about 1.8 microns and about 2 microns, or a signal wavelength of including the range of about 1.6 microns and about 1.8 microns or a signal wavelength of including the range of about 1.4 microns and about 1.6 microns, while in other embodiments, between about 0.2 microns and about 3 microns, inclusive) is another way to stimulate a NAP.

In some embodiments, the present invention provides methods and apparatus for stimulating nerves, fascicles, and individual nerve fibers in the PNS and CNS, including cranial nerves. In some embodiments, the methods and apparatus described herein are capable of being configured to stimulate a single nerve, a single fascicle, a single nerve fiber, multiple nerves, multiple fascicles, multiple nerve fibers or a combination of one or more nerves, and/or one or more fascicles, and/or one or more nerve fibers. As used herein, a method or apparatus that is described as being capable of stimulating a nerve is also capable of providing stimulation of fascicles and nerve fibers or a combination of nerve(s), and/or fascicle(s), and/or nerve fiber(s).

In some embodiments, the present invention provides permutations for practical implementation of implantable light-neural interfaces in peripheral and cranial nerves for stimulating sensory or motor function as needed for a given application. In some embodiments, neural prosthetic devices are artificial extensions of the body that restore or supplement nervous system function that were lost due to disease or injury. The current worldwide market for neural prostheses and similar neuromodulation devices is estimated to be over $3 billion, and roughly ⅓ to ½ of which involves interaction with peripheral and cranial nerves. Previous and current conventional devices use electrical stimulation (ES) to interface with the nervous system, which leads to numerous issues. Because electrical current spreads in the body, most if not all ES-based neural prostheses wind up stimulating other nerves in the area besides the intended target (e.g. fine movements cannot be made with a motor prosthesis, and multiple sensations, such as touch and temperature, may be felt incorrectly from a sensory feedback device). Furthermore, the presence of a stimulation artifact can obfuscate signals elsewhere along the nerve, and it also precludes stimulating and recording electrical nerve activity in the same location, as needed for a closed-loop sensorimotor limb prosthesis. Thus, all of the numerous ES-based neural interfaces have fundamental shortcomings that limit their ability to seamlessly integrate with the human body.

Infrared Neural Stimulation (INS) has the potential to significantly improve neural prostheses and neuromodulation devices and INS has improved selectivity over ES because light is directed in a single direction; and thus INS has no stimulation artifact, which allows for stimulation and recording of nerve activity in the same location. Importantly, the various materials available for these INS implantable designs can be safer and more biocompatible than current ES devices. Thus, these INS implantable interface designs are key to the development of more precise, biofidelic neural devices to meet a very large, growing worldwide demand.

In some embodiments, the disclosed designs for interfacing light (infrared for INS or other wavelengths, typically visible, for "photostimulation") with peripheral, cranial, or central nerves can be broken down into two major subgroups. A first group of designs use direct light output of vertical-cavity surface-emitting lasers (VCSELs) to stimulate nerves, with VCSELs being placed either outside the nerve ("non-invasive"), just inside the epineurium, which is the outermost covering of the nerve ("minimally invasive"), or placed amongst the individual fascicles inside the nerve ("invasive"). Another group of designs uses light being delivered from either a VCSEL or other laser via a number of very different waveguide designs in non-invasive, minimally invasive, or invasive approaches as defined above.

In some embodiments, these INS implantable devices have control electronics to drive them to elicit the appropriate physiological response (e.g. motor function, sensory inputs, and the like) by stimulating a peripheral, central, or cranial nerve. In some embodiments, the present invention provides practical interface designs for the implantable devices to effectively utilize the present invention.

The present invention uses a light-propagating transmission medium to carry optical signals between a light source and the tissue (e.g., neurons) of the patient, in order to stimulate a nerve action potential. In some embodiments, the transmission medium includes one or more optical fibers (e.g., a bundle of optical fibers, each of which includes a waveguide (e.g., the core of the fiber, which has a higher index of refraction than the cladding). In some embodiments, the light-propagating medium includes a plurality of side-by-side longitudinal (parallel-like) waveguides formed in an optical fiber or optical "ribbon." In some embodiments, a planar substrate is used, wherein the planar substrate includes a plurality of waveguides, and optionally includes other optical components such as filters, evanescent couplers, optical-fiber interfaces, selective gates that control the amplitude of light output, focusing elements, light-output ports (e.g., gratings that allow light to exit the waveguides toward the tissues of interest) and the like. In some embodiments, a tapered silicon substrate (or other light-transmitting material such as: ZnSe, InP, fused silica, quartz, and the like) is used, the substrate having a plurality of waveguides formed by three-dimensional (3D) etching at the light-output tip (and optionally also at an input interface that receives light (e.g., from a plurality of optical fibers). In some embodiments, the output end of such an optical element is called a "probe" and allows a large number of light-output ports, such that after implantation adjacent to the brainstem or midbrain of the patient, individual ones of the output ports are individually activatable to determine which ports stimulate which nerve pathways. A mapping of which port is coupling light to which nerve pathway is then programmed into the controller that drives a particular optical signal to the desired nerve pathway to be stimulated. Because there are many more light-output ports than nerve destinations, the implanted device can be programmed to send the appropriate signals to each of a plurality of nerve pathways, greatly simplifying placement of the output probe (as compared to having to individually place each of a plurality of separate fibers). Further, at a later time, the implanted device can be recalibrated, remapped and reprogrammed to compensate for movement of the probe relative to the tissue to be stimulated. In addition, refinements based on later-discovered principles can be reprogrammed into the implanted device to provide a better sense of hearing for audio implants. Of course, other embodiments include implanted devices that provide other sensations, such as vision, olfaction, touch (some embodiments including sexual sensations), temperature, pressure, and the like.

In some embodiments, the light signal used to stimulate a nerve action potential includes wavelengths in the range of 1800 nm to 2100 nm. In other embodiments, the stimulation light signal includes wavelengths in the range of 1400 nm to 1500 nm, the range of 1500 nm to 1600 nm, or other suitable light wavelength in the range of 300 nm to 10,000 nm.

FIG. 2A is a block diagram of an implantable or partially implantable system 201 (according to some embodiments of the present invention) that uses a VCSEL (vertical-cavity surface-emitting laser) array for light stimulation of neuronal tissue 99 in the brainstem and/or midbrain nerves such as the auditory brainstem to obtain an auditory brainstem response (ABR) (e.g., some embodiments use a VCSEL array such as described by U.S. Provisional Patent Application No. 60/964, 634 filed Aug. 13, 2007, titled "VCSEL Array Stimulator Apparatus and Method for Light Stimulation of Bodily Tissues," which is incorporated herein by reference in its entirety). System 201 represents one embodiment of the present invention, wherein a low-power, low-threshold VCSEL array 205 emits laser light from each of a plurality of VCSELs, for example VCSELs implemented as an array of separately activatable lasers formed in a monolithic semiconductor chip. Each laser beam is separately controlled by controller signals 218 from laser-and-power controller 210 under control of a stimulation-calculation processor or circuitry 209. Controller signals 218 drive the laser-diode VCSELs that generate light signals 211 that are configured to stimulate the tissue as desired. For example, in some embodiments, the light signals 211 are collimated, focused and/or guided by optics 203 within device enclosure 204 into delivery medium 207 (e.g., a bundle of optical fibers), which extends from the enclosure 204 to a remote location such as in the brainstem or midbrain 99 of patient 98. In some embodiments, the system also uses a visible laser and/or LED (light-emitting diode) array 206 that produce visible light signals 212 to help align the VCSEL laser array signals 211 with the lens array/beam coupler/combiner optics 203, and/or to indicate where the IR signals are being emitted from the far end of delivery medium 207 to help the surgeon align the distal tip of the delivery medium 207 to the appropriate neuronal tissue during the implantation procedure. In some embodiments, one or more sensors 208 are used to obtain audio information, balance or orientation information, temperature information, or other information that is to be converted to nerve-stimulation signals (e.g., optical signals and optionally also electrical signals) to deliver to patient 98 through the patient's brainstem or midbrain neurons 99. In some embodiments, the sensors 208 are implanted inside the patient 98. In other embodiments (such as described below for FIG. 2B), one or more sensors are part of an external unit 220 that is wirelessly coupled to the implanted device 202.

In some such embodiments, implantable/partially implantable system 201 includes rechargeable batteries to provide power to the stimulator. In some such embodiments, power is provided to the system 201 from outside of the body using wireless charging (e.g., in some embodiments, inductive battery charging) such that the batteries can be recharged without the need to perform surgery to gain access to the stimulator.

In some embodiments, electrical nerve-stimulation signals 219 are generated by stimulation-calculation processor or circuitry 209, and are delivered to the stimulation site using delivery medium 207 (e.g., a bundle having one or more electrical conductors and one or more optical fibers), such as described in U.S. patent application Ser. No. 12/018,185 filed Jan. 22, 2008, titled "Hybrid Optical-Electrical Probes" (now U.S. Pat. No. 7,883,536 issued Feb. 8, 2011); U.S. patent application Ser. No. 12/191,301 filed Aug. 13, 2008, titled "VCSEL Array Stimulator Apparatus and Method for Light Stimulation of Bodily Tissues", and U.S. patent application Ser. No. 12/573,848 filed Oct. 5, 2009, titled "Nerve Stimulator and Method using Simultaneous Electrical and Optical Signals"; each of which is incorporated herein by reference in its entirety. In other embodiments, optical-only stimulation is used, and thus no electrical stimulation is used in such embodiments.

In some embodiments, the electrical signals 219 are used to sensitize the neuronal tissue (as opposed to being sufficient to trigger a nerve action potential using only the electrical signal) in order that a lower-power optical stimulation signal is sufficient to trigger the desired nerve action potential (NAP) in one or more neurons in the brainstem or midbrain of the patient, the spinal cord or other nerves.

In some embodiments, the optical (and optional electrical) signals are delivered and directed upon the auditory brainstem nerves, i.e., Cranial Nerve VIII (the cranial nerve for hearing and balance), or other brainstem or midbrain tissue 99 of a patient 98. In some embodiments, some or all of system 201 is implanted within patient 98. In some embodiments, the end of delivery medium 207 that is distal to beam combiner 203 includes a plurality of optical fibers that are configured to output light in a plurality of different locations and/or different directions from a single location. In some embodiments, delivery medium 207 also includes a plurality of electrical conductors that are configured to output electrical signals in a plurality of different locations (e.g., to one or more of those locations at any one time) and/or different directions (e.g., to one or more of those directions at any one time) from a single location. In some embodiments, the electrical signals are used to precondition the neurons to be stimulated such that a lower-intensity optical signal can be used to trigger the desired nerve-action-potential pulse.

In some embodiments, the optical (and optional electrical) signals are delivered and directed upon other brainstem nerves, for instance, Cranial Nerve II (the cranial nerve for vision), Cranial Nerve I (the cranial nerve for olfaction), or the like. In some such embodiments, suitable external sensors 208 for the necessary input data (environmental parameters) from the environment (such as, for example, microphones, pressure sensors, vibration sensors, gyroscopes, accelerometers, gravity-direction sensors, electromagnetic-radiation sensors such as imaging devices, light sensors and color sensors, chemical sensors (i.e., for odors and/or taste), and the like; collectively called environmental sensors, which generate environmental signals and/or environmental data, based on the environmental parameter(s), which are to be analyzed and used to control nerve stimulators).

In some embodiments, one or more pressure, texture, vibration, weight and/or similar sensors are used to obtain touch-and-feel data from the environment, this touch-and-feel data is processed to detect mechanical-touch aspects of an object, and the processed mechanical-touch data is used to generate stimulation signals used to drive optical and/or electrical probes that therapeutically stimulate the midbrain or brainstem portion of other nerve pathways in order to provide a simulated touch-and-feel sensation for the patient.

In some embodiments, one or more balance, acceleration, rotation and/or similar environmental sensors as used to sense the position and movement of the patient's body within its environment, and the resulting signals are used to therapeutically stimulate nerves to correct balance or movement problems.

Further, in some embodiments, one or more nerve-action-potential (NAP) sensors are used to obtain nerve-and-movement-disorder data, this nerve-and-movement-disorder data is processed to detect nerve-signal patterns that are indicative of Parkinson's Disease or other movement disorders, and the processed nerve-signal data is used to generate stimulation signals used to drive optical and/or electrical probes that stimulate the midbrain or brainstem portions (such as the red nucleus and substantia nigra) of affected nerve pathways in order to treat or inhibit the movement disorder of the patient. In some embodiments, such NAP sensors and/or other patient-physiology sensors (such as muscle-contraction sensors, EKG (electrocardiogram) sensors, EEG (electroencephalogram) sensors, temperature sensors, stomach-acid sensors and the like) are used to generate patient-physiology signals and/or patient-physiology data to be analyzed and used to control nerve stimulators.

Still further, in some embodiments, an imaging device is used as a sensor 208 (or as part of an external sensor-transmitter 220 as described below for FIG. 2B) to obtain image data, this image data is processed to detect vision aspects of the image data such as patterns (e.g., vertical objects, horizontal objects, diagonal objects, curved objects and the like), color (e.g., hue, saturation, brightness, contrast and the like with regard to various objects and patterns), motion (direction, speed, enlargement, and the like) and the processed image data is used to generate stimulation signals used to drive optical and/or electrical probes that stimulate the midbrain or brainstem portion of Cranial Nerve II (the cranial nerve for vision) in order to provide a simulated vision sensation for the patient. In some embodiments, electromagnetic-radiation sensors that do not generate image data as such, for example light sensors and color sensors, are used to obtain more generic electromagnetic-radiation data from the environment (such as the color of an object), and this generic electromagnetic-radiation data is processed to provide and control optical- and/or electrical-stimulation signals that stimulate the midbrain or brainstem portion of Cranial Nerve II to provide more fundamental sensations (such as the color of whatever the color sensor is aimed at).

Even further still, in some embodiments, one or more chemical sensors are used to obtain chemical data from the environment (e.g., data relating to gases or particulates from the atmosphere, or materials such as salts, sugars and the like dissolved in a liquid), this chemical data is processed to detect odor aspects of the chemical data, and the processed odor data is used to generate stimulation signals used to drive optical and/or electrical probes that stimulate the midbrain or brainstem portion of Cranial Nerve I (the cranial nerve for olfaction) in order to provide a simulated smell and/or taste sensation for the patient.

In some embodiments, and as used herein and as used in the attached Figures and graphs, 100% power is 5 watts, and this delivers a pulse energy of 5 mJ in a 1-ms pulse. Thus, in FIG. 2A, a 100% power level (5 watts) delivered in 3-ms pulses is delivering 15 mJ per pulse, an 80% power level (4 watts) delivered in 3-ms pulses is delivering 12 mJ per pulse, a 60% power level (3 watts) delivered in 3-ms pulses is delivering 9 mJ per pulse, a 40% power level (2 watts) delivered in 3-ms pulses is delivering 6 mJ per pulse, and a 20% power level (1 watt) delivered in 3-ms pulses is delivering 3 mJ per pulse. Thus, 100% of 5 watts in a 3-millisecond pulse delivers 15 mJ per pulse energy. Similarly, in FIG. 2B, 80% of the 5-W power (i.e., 4 watts) in a 0.75-ms pulse delivers 3.0 mJ per pulse. In some embodiments, less than one watt of optical power is used, (e.g., in some embodiments, in a range of 100 mW to 999 mW) and pulse durations in the range of about 10 microseconds to 10,000 microseconds (10 ms) are used, resulting in pulse energies in a range of about one micro joule to about 9.99 milli joules. In other embodiments, other amounts of optical power and/or energy are used.

In some embodiments, long-wavelength VCSEL devices and/or VCSEL arrays, such as described in U.S. Pat. Nos. 7,031,363 and 7,004,645 (which are each incorporated herein by reference), are used for the VCSEL array 205.

With VCSEL emitters as small as about ten (10) microns (or smaller) in diameter per channel, in some embodiments, a single VCSEL chip or assembly is used to output multiple independent stimulation channels (VCSEL laser signals) in any array permutation or shape, and in some embodiments, these channels are fiber coupled, and/or direct light directly, to a plurality of areas of tissue. In some embodiments, a combination of both fiber-coupled and direct-propagation laser output is used to stimulate tissue.

FIG. 2B is a block diagram of a wireless-transmission partially implantable system 202 that uses a VCSEL array for light stimulation of PNS, CNS, and/or brainstem and/or midbrain neurons and/or organs 99. In some embodiments, system 202 is substantially similar to system 201 described above, except that one or more external sensors, computer processing devices and wireless-transmitter circuitry 220 replace or supplement one or more of the sensors 208. For example, in some embodiments, the external sensors include a pressure sensor, a processor that converts the measured pressure into information that is wirelessly transmitted (for example using radio waves or other suitable means) to an implanted receiver, wherein the transmitted information is useful for generating optical (and optionally electrical) pulses that are used to stimulate neurons 99 of patient 98. In some embodiments, system 202 represents one embodiment of the present invention wherein a low-power, low-threshold VCSEL array 224 emits laser light from each of a plurality of VCSELs, for example VCSELs implemented as an array of separately activatable lasers formed in a monolithic semiconductor chip. Each laser beam is separately controlled by laser-and-power controller 222 that drives controller signals 226 to the set of laser-diode VCSELs 224, which together are configured to stimulate the tissue as desired. For example, in some embodiments, the light signals are collimated, focused and/or guided by optics into delivery medium 228 (e.g., a bundle of optical fibers). In some embodiments, the system also uses a visible laser and/or LED array (such as array 206 described above) that produce visible light signals to help align the VCSEL laser array signals with the lens array/beam coupler/combiner optics. In some embodiments, electrical-stimulation or -preconditioning signals are also applied to the tissue 99 in combination with the optical stimulation signals in order to reduce the optical power needed to obtain a NAP.

In some embodiments, cable 226 carries both electrical power and control signals. In some embodiments, the electrical control signals in cable 226 are multiplexed to reduce the number of wires and/or size of the cable connecting the control electronics 222 to the VCSEL-driver circuit(s) 224 (which, in some embodiments, also include electrical-stimulation signal drivers to drive electrical-stimulation or -preconditioning signals that are optionally also applied to the tissue 99 in combination with the optical stimulation signals). In some embodiments, the electrical control signals in cable 226 are time-division multiplexed or serially multiplexed. In some embodiments, the electrical signals in cable 226 are multiplexed through encoding. In some other embodiments, other commonly known methods of multiplexing are use to reduce the number of wires and/or size of the cable connecting the control electronics to the VCSEL driver circuit 224. In some such embodiments, VCSEL-driver circuit 224 includes a de-multiplexor and/or decoder that uses the information in signals from cable 226 to activate selected ones of the VCSELs at the appropriate times to trigger the desired response, and optionally to activate associated preconditioning electrical signals to sensitization electrodes in the vicinity of tissue 99. This provides an implantable MUX-DMUX (multiplexer/demultiplexer) capability, that implements a level of 'smarts' and/or programmability in the implanted device 202 to simplify the interface 226 between the VCSEL/driver package 224 to the rest of the neurostimulator system 222 (which includes a battery, software processing, telemetry, etc).

FIG. 2C is a schematic side view and FIG. 2D is a schematic end view, respectively, of an implantable fiber-optic bundle device 253 with optional electrical conductors 236 and 237. In some embodiments, implantable fiber-optic bundle 253 includes a plurality of radially positioned fiber-optic cables (e.g., a bundle of optical fibers around a central axis) 232, 233, 234 and 238. In some embodiments, a first set or tier (i.e., an innermost bundle) of optical fibers 232 are arranged radially around a central axis and terminates using angled facets (i.e., angled to direct light in a plurality of different outward angles from the central axis of the bundle of fibers) at the distal end of fiber-optic device 253. The angled facets are configured to each direct light from one or more core regions within each fiber 232 at a different radial (or radial-and-longitudinal) direction than the light coming from other fibers 232. In some embodiments, each fiber is configured to emit light outward from one end of the central axis of fiber-optic device 253 such that a different unique or limited set of one or more nerve fibers is stimulated by optical pulses emitted from each one of the angled end facets of the respective fibers. In some embodiments, device 253 is oriented such that the central axis of device 253 is substantially parallel to the length direction of the nerve bundle that is to be stimulated.

In some embodiments, common electrode 236 of FIG. 2C uses the bundle of optical fibers 238 to provide electrical insulation such that longitudinal electric fields are generated between the exposed end of wire 236 and the ends of one or more individual wires that have their exposed end electrodes 237 activated one or more at a time such that a voltage is applied between the end of wire 236 and the end of electrode(s) 237.

In some embodiments, the device 253 is implanted into a patient 98, and optical pulses are sent out one fiber at a time in order to identify which fiber evokes which sensation or response (such as the perception of a particular frequency caused by nerve pulses of a particular nerve, nerve axon, or the like). Once it has been determined which optical fiber evokes which response or sensation, the electronics portion 231 is configured or its software is programmed to send pulses at a calculated rate to cause the patient to sense the desired sensation (e.g., in some embodiments, to "hear" a voice having a complex mix of frequencies and intensities, the patient must receive nerve pulses (compound nerve action potentials, or CNAPs) at certain rates from certain nerve pathways, and device 253 would transmit optical signals (or a combination of optical and electrical signals) to cause the particular set of nerves to experience the CNAPs necessary for that "hearing" (or other sensation), which, for example, could be based on processing a microphone-received audio signal and generating a corresponding set of optical pulses at given repetition rates that are delivered through a selected set of optical fibers).

In some embodiments, a second set or tier of optical fibers 233 are arranged around the central axis radially further out and around the outer circumference of fiber-optical fibers 232, and each optical fiber 233 terminates using an outward-angled facet spaced at a short distance (leftward in FIG. 2C), e.g., at 500 microns (0.5 mm), 1 mm, 1.5 mm, 2 mm or other suitable distance from the distal end (the right-hand end in FIG. 2C) of fiber-optic bundle 253. In some embodiments, a third set or tier of optical fibers 234 are arranged around the central axis and radially further out and around the outer circumference of optical fibers 232 and optical fibers 233, and each optical fiber 234 terminates using an outward-angled facet spaced at a short distance (further leftward in FIG. 2C), e.g., at 1000 microns (1 mm), 1.5 mm, 2 mm, 2.5 mm, 3 mm or other suitable distance from the distal end (the right-hand end in FIG. 2C) of the fiber-optic bundle of device 253. In some embodiments, yet another set of optical fibers 238 are arranged around the central axis and optical fibers 232, optical fibers 233 and optical fibers 234 (i.e., optical fibers 238 surround optical fibers 234, optical fibers 234 surround optical fibers 233, optical fibers 233 surround optical fibers 232 and optical fibers 232 are arranged radially around the central axis). In some embodiments, each optical fiber 238 terminates using an outward-angled facet spaced at a short distance (still further leftward in FIG. 2C), e.g., at 1500 microns (1.5 mm), 2 mm, 2.5 mm, 3 mm, 3.5 mm, 4 mm or other suitable distance from the distal end (the right-hand end in FIG. 2C) of the fiber-optic bundle of device 253. Thus, in some embodiments, the ends of the fiber-optic cables 234 extend a distance beyond the ends of fiber-optic cables 238, the ends of the fiber-optic cables 233 extend a distance beyond the ends of fiber-optic cables 234 and the ends of the fiber-optic cables 232 extend a distance beyond the ends of fiber-optic cables 233 such that light emitted by each faceted end is not obstructed by surrounding fiber-optic cables and reaches a different portion of nerve tissue.

In some embodiments, the plurality of optical fibers 232, 233, 234 and 238 include faceted ends (e.g., cleaved or polished ends), wherein the face or facet of each faceted end of the plurality of optical fibers 232, 233, 234 and 238 points in a different radially-outward and longitudinally angled direction with respect to the central axis such that light emitted from each faceted end (e.g., 235 and 239) travels in a direction that is at least partially radially outward from the central axis and intersects a different nerve or set of nerve pathways.

In some embodiments, fiber-optic bundle 253 includes a plurality of electrical conductors 236 and 237. In some embodiments, one or more of the electrical conductors include a central conducting core (e.g., a bio-compatible metal or alloy) surrounded by an insulating material (e.g., a bio-compatible polymer, glass, enamel or other suitable insulator. In some embodiments, electrical conductor 236 is a single insulated wire with an exposed end electrode (e.g., bare wire coated or plated with a bio-compatible electrically conductive surface) that is used as a common conductor for a plurality of other individually selectable electrodes 237 (i.e., a voltage is applied to the common electrode 236 and one of the selectable electrodes 327), and that is, in some embodiments, arranged at the central axis of the plurality of fiber-optic cables 232, 233, 234 and 238 and the end of electrical conductor 236 is flush with or extends a short distance (e.g., in some embodiments, 500, 1000, or 1500 microns) beyond the end of fiber-optic cables 232. In some embodiments, electrical conductors 237 include a plurality of insulated wires (or metallic-coated optical fibers or the like) arranged radially around or within the outer plurality of fiber-optic cables 238 and the exposed end electrodes (e.g., in some embodiments, also bare wire coated or plated with a bio-compatible electrically conductive surface)of the electrical conductors 237 are arranged such that fiber-optic cables 238 are co-terminus or extend past the ends of the electrical conductors 237. In other embodiments, rather than using a single common electrode 236, selected pairs of electrodes 237 have voltages applied, such that either a longitudinal voltage, a circumferential voltage or both a longitudinal and circumferential voltage is applied through the surrounding tissues of the patient. In some embodiments, controller 231 generates signals or electrical current flows from one electrical conductor of the plurality of electrical conductors 237 to a second and different electrical conductor of the plurality of electrical conductors 237 (i.e., in a direction tangent to the optical-fiber bundle). In some embodiments, electrical current flows from one or more electrical conductors of the plurality of electrical conductors to the single electrical conductor 236 (i.e., in a longitudinal direction relative to the optical-fiber bundle or relative to one side of the optical-fiber bundle of device 203). In some embodiments, the electrical conductors are formed as a conducting layer (e.g., a metallization layer) that is deposited directly on each of one or more of the optical fibers 238, 234, and/or 233, and then covered (except at an exposed conductive probe (e.g., near the tip of the optical fiber) with one or more insulating layers (e.g., hybrid electro-optic fibers such as described in U.S. patent application Ser. No. 12/018, 185 filed Jan. 22, 2008, titled "Hybrid Optical-Electrical Probes" (now U.S. Pat. No. 7,883,536 issued Feb. 8, 2011), which is incorporated herein by reference).

FIG. 2E is a schematic side view of an optical fiber 238 from the implantable fiber-optic bundle device 253 of FIG. 2C in an implanted configuration 250. In some embodiments, the index of refraction of fiber 238 (labeled in the figures as $N_F$) is greater than the index of refraction of the tissue (labeled in the figures as $N_T$) in which device 253 is implanted and thus the light 235 emitted from the faceted end of fiber 238 travels in a first radial direction away from the central axis of fiber 238.

FIG. 2F is a schematic side view of an optical fiber 238 from the implantable fiber-optic bundle device 253 of FIG. 2C in an implanted configuration 251. In some embodiments, the index of refraction of fiber 238 ($N_F$) is less than the index of refraction of the tissue ($N_T$) in which device 253 is implanted and thus the light 235 emitted from the faceted end of fiber 238 travels in a second radial direction away from the central axis of fiber 238.

FIG. 2G is a schematic side view of an optical fiber 248 in an implanted configuration 252. In some embodiments, fiber 248 is substantially similar to fiber 238 except that the faceted end 256 of fiber 248 reflects or diffracts light 235 out of fiber 248 through a window 255 in a radial or side ("side firing") direction of the fiber 248 (see, for example, waveguide 411 of FIG. 4).

FIG. 2H is a schematic side view of an implantable fiber-optic bundle 258. In some embodiments, a single common electrode 236 has a series of insulated segments 236F, 236D, and 236B alternating with exposed electrically conductive electrodes 236E, 236C, and 236A along a single wire. The common electrode 236 of FIG. 2H (as well as the common electrode 236 of FIG. 2C, which uses the bundle of optical fibers to provide electrical insulation such that longitudinal electric fields are generated between the exposed end of wire 236 of that implementation and the ends of one or more individual wires that have their exposed end electrodes activated one or more at a time such that a voltage is applied between the end of wire 236 and the end of electrodes 237) is implemented in a central portion of the bundle in some embodiments, while in other embodiments, the common electrode 236 is not in the center. In some embodiments, one of the electrodes 237 and the common electrode 236 have voltages applied, such that a longitudinal voltage, a circumferential voltage or both a longitudinal and circumferential voltage is applied through the surrounding tissues of the patient. For example, applying a voltage pulse that is positive on wire 237A relative to the common electrode 236 will apply longitudinal voltages through the tissue between electrode 237A and the exposed electrodes 236E and 236C (depending on the pulse polarity applied to the wires involved, this produces left-to-right voltage polarity (−V1+) relative to the figure in one case and right-to-left (+V1−) in the other case). In some such embodiments, an optical pulse at location A is emitted from the appropriate optical fiber to trigger an action potential in the tissue that is pre- or simultaneously conditioned with the (−V1+) electrical pulse between exposed electrodes 236E and 237A, while no action potential is triggered in the tissue that is pre- or simultaneously conditioned with the (+V1−) electrical pulse between exposed electrodes 237A and 236C. In some embodiments, if the response in the tissue is affected by the longitudinal direction of the voltage, the polarity of the pulse is adjusted to achieve the desired action potential response in the tissue when the associated optical pulse is applied. In some such embodiments, an optical pulse at location B is emitted from the appropriate optical fiber to trigger an action potential in the tissue that is pre- or simultaneously conditioned with the (+V1−) electrical pulse between exposed electrodes 237A and 236C, while no action potential is triggered in the tissue that is pre- or simultaneously conditioned with the (+V1−) electrical pulse between exposed electrodes 237A and 236E.

Likewise, an optical pulse at location C is emitted from the appropriate optical fiber to trigger an action potential in the tissue that is pre- or simultaneously conditioned with the (−V2+) electrical pulse between exposed electrodes 236C and 237B, while no action potential is triggered in the tissue that is pre- or simultaneously conditioned with the (+V2−) electrical pulse between exposed electrodes 237B and 236A. Likewise, an optical pulse at location D is emitted from the appropriate optical fiber to trigger an action potential in the tissue that is pre- or simultaneously conditioned with the (+V2−) electrical pulse between exposed electrodes 237A and 236C, while no action potential is triggered in the tissue that is pre- or simultaneously conditioned with the (−V2+) electrical pulse between exposed electrodes 237B and 236C.

In some embodiments, a plurality of common electrodes 236 are used, each with alternating insulated segments 236F, 236D, and 236B alternating with exposed electrically conductive electrodes 236E, 236C, and 236A. In other embodiments, selected pairs of electrodes 237 have voltages applied (e.g., electrodes 237A and 237B), such that either a longitudinal voltage, a circumferential voltage or both a longitudinal and circumferential voltage is applied through the surrounding tissues of the patient.

In some embodiments, a combination of electrical signal(s) and optical signal(s) is used to generate the desired response (e.g., a CNAP in each of one or more nerve pathways at a repetition rate or time sequence chosen or calculated to generate a given sensation for the patient). In some embodiments, an external sensor is used to gather information about the environment (e.g., a pressure sensor, an audio sensor, a video images sensor, or information from a gyroscope sensor, tilt sensor, temperature sensor, chemical or odor sensors or the like), which information is optionally processed external to the patient, and the resulting data is wirelessly transmitted (e.g., using radio waves) to an implanted device 203 internal to the patient. Thus, in some embodiments, a sensation of touch or feeling is obtained using device 203. In other embodiments, other sensations such as balance, vertigo or the avoidance of vertigo, tilt, vision, touch, smell, or other sensation is obtained using device 203, wherein the given sensor(s) are collecting sensory data and device 203 is generating the corresponding sensation, depending on the location where the ends of the optical fibers (or bundle of optical fibers) and optionally electrical conductors are delivering the optical signals and optionally the electrical signal(s) or pre-conditioning stimulus. In other embodiments, a motor response (rather than a sensation) of the patient is obtained, such as a limb, hand, eye, or tongue movement and/or the like. By implanting the light-emitting end of the optic-fiber bundle of device 203 in or along motor nerves of the spinal cord or peripheral nerve system, other motor responses (muscle contractions) may be obtained.

In some embodiments, the optical-fiber bundle end of device 203 is situated in or along a spinal nerve and or multiple spinal nerves of the peripheral nervous system (PNS), or in or along a nerve or nerve bundle of the spinal cord of the central nervous system (CNS), or even in or along the brainstem or the side of the higher brain centers such as the cerebral cortex. In some embodiments, the optical-fiber bundle end of device 203 is situated in or along the limbic system (e.g., thalamus, hypothalamus, amygdala, and/or hippocampus), or the pituitary gland, cerebellum, or corpus callosum.

Spinal nerves in the human body are formed from nerve fibers from both the dorsal and ventral roots of the spinal cord, with the dorsal roots carrying sensory information from the distal end of the PNS to the spinal cord and brain of the CNS and the ventral roots carrying motor function information from the brain and spinal cord to the distal ends of the PNS. The spinal nerves split off from the spinal cord and exit from the spinal column through the intervertebral foramen opening between adjacent vertebrae. After leaving the spinal column and splitting into the dorsal and ventral roots, the spinal nerves divide into branches and extend to various locations and in the body to detect and communicate sensory and motor information between the PNS and the CNS.

The human brain has twelve pairs of special nerves called the cranial nerves. These are specific bundles of neurons and axons which transmit special information to and from the brain, without going through the spinal cord. The cranial nerves each provide highly specific functions (sensory or motor). The cranial nerves all exit from the bottom of the brain and brainstem and exit the skull through various foramina to reach their sources or targets. In some embodiments, the optical-fiber-bundle light-delivery (and optionally electrical-stimulation) end of device 203 is situated in or along one or more of the cranial nerves to obtain one or more of the following responses of Table 1:

TABLE 1

| CRANIAL NERVE | NAME | MAIN FUNCTION |
| --- | --- | --- |
| Cranial Nerve I | Olfactory Nerve | Smell |
| Cranial Nerve II | Optic Nerve | Vision |
| Cranial Nerve III | Oculomotor Nerve | Eye movement |
| Cranial Nerve IV | Trochlear Nerve | Eye movement |
| Cranial Nerve V | Trigeminal Nerve | Facial sensation |
| Cranial Nerve VI | Abducens Nerve | Eye movement |
| Cranial Nerve VII | Facial Nerve | Facial movement |
| Cranial Nerve VIII | Auditory Nerve | Hearing and balance |
| Cranial Nerve IX | Glossopharyngeal Nerve | Organs and Taste |
| Cranial Nerve X | Vagus Nerve | Organs and Taste |
| Cranial Nerve XI | Accessory Nerve | Shoulder shrug & head turn |
| Cranial Nerve XII | Hypoglossal Nerve | Tongue movement |

In some such embodiments, wherein the optical-fiber bundle end of device 203 is situated in or along the brainstem (the medulla, pons and/or midbrain), or along the cranial nerves, or even in or along side of the higher brain centers such as the cerebral cortex or wherein the optical-fiber bundle end of device 203 is situated in or along the limbic system (e.g., thalamus, hypothalamus, amygdala, and/or hippocampus), or the pituitary gland, cerebellum, or corpus callosum, optical pulses and/or a combination of electrical pulses and optical pulses are used to generate a desired response in a particular nerve or nerves to sense an external stimuli (e.g., a smell, a visual stimuli, or a taste, and/or the like) or to provide a motor control signal to a portion of the body (e.g., to move the tongue or eyes, to turn the head, or to smile, and/or the like). In some embodiments, the nerve that is being stimulated or activated has been damaged or severed in a location that is between the distal end of the nerve and the brainstem, cranial nerves, or higher brain centers and therefore sensory signals coming from the distal end of the nerve are not able to reach the CNS for processing and motor signals coming from the CNS are not able to reach the distal end of the nerve to provide the desired motor movement.

Figure 3:
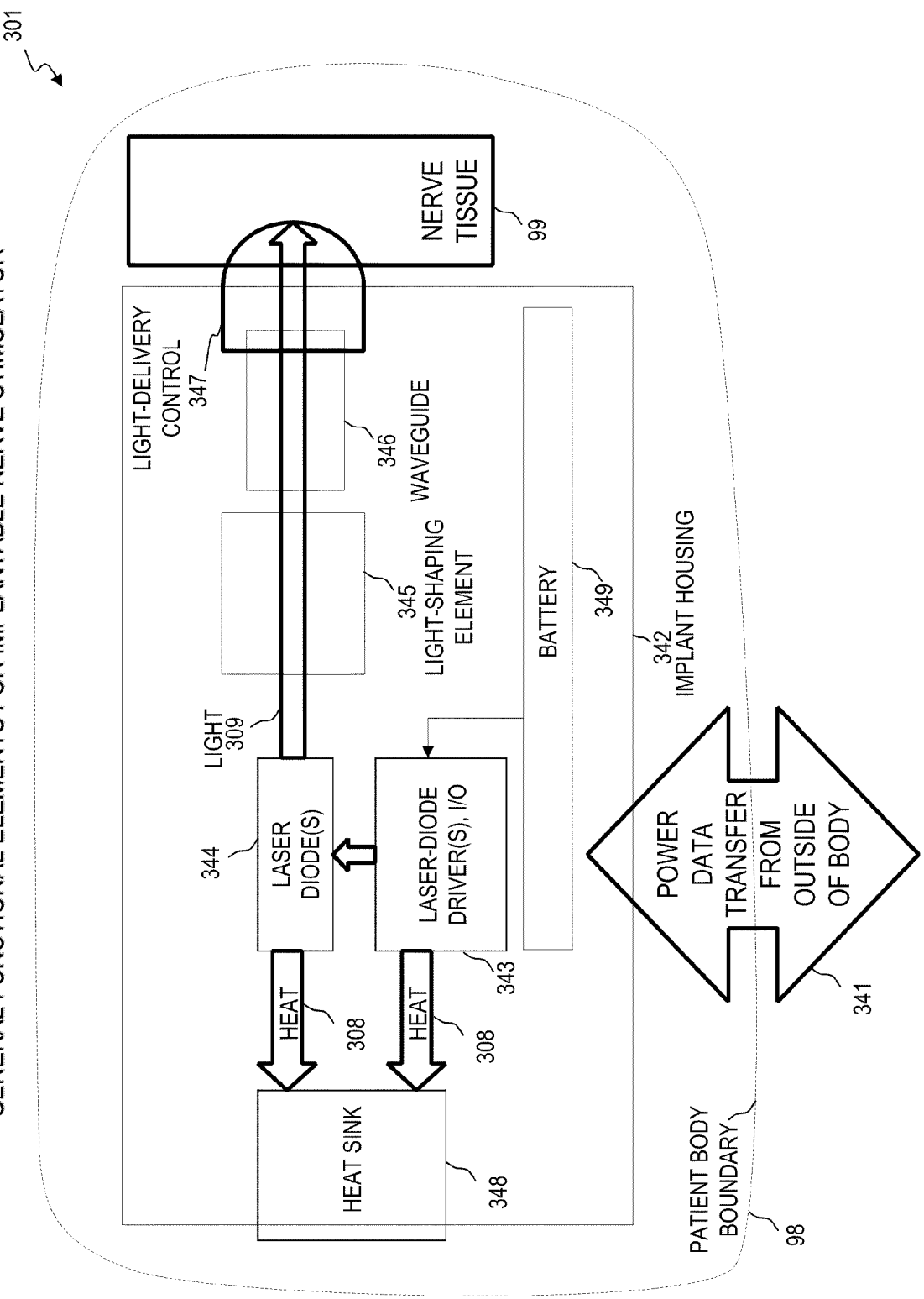
FIG. 3 is a schematic block diagram of nerve stimulator 301, according to some embodiments of the present invention.

FIG. 3 is a schematic block diagram of nerve stimulator 301, according to some embodiments of the present invention. In some embodiments, nerve stimulator 301 is completely implanted into a patient (e.g., a human animal or a non-human animal) and is completely contained within the patient with no ports or connections extending from internal to the patient across the patient body boundary 98 and then external to the patient. In some such embodiments, nerve stimulator 301 includes rechargeable batteries to provide power to the stimulator and power is provided to the implanted nerve stimulator 301 from outside of the body using wireless charging 341 (e.g., in some embodiments, inductive battery charging) such that the batteries can be recharged without the need to perform surgery to gain access to the stimulator. Also, in some such embodiments, nerve stimulator 301 includes a wireless communications transmitter/receiver to receive information from outside the body (e.g., in some embodiments information received by stimulator 301 from outside the body includes environmental data, sensory data, and/or stimulator operational instructions and programming, and/or the like) and to transmit information from stimulator 301 to outside the body (in some embodiments, information sent by stimulator 301 to outside the body includes stimulator error codes, stimulator diagnostics, and/or stimulator operational condition information, and/or the like). In other embodiments, nerve stimulator 301 is partially implanted into the patient such that the nerve stimulator 301 is not completely contained within the patient's body (i.e., at least a portion of the nerve stimulator 301, including, but not limited to, a port or a connection) crosses the patient body boundary 98 and resides external to the patient. In some such embodiments, power and data communications between nerve stimulator 301 and power and/or devices is provided via electrical cables and connectors. Some embodiments include an external-to-the-body portion that includes sensors (e.g., microphones, accelerometers, gyroscopes, magnetometers, pressure sensors, moisture sensors, light sensors (for one or more ultraviolet, visible, and/or infrared wavelengths), chemical sensors, imaging devices, radio-wave antennae, temperature sensors, and the like), electrical power, programming, input/output signals, transmitter/receiver and/or other devices.

In some embodiments, nerve stimulator 301 includes implant housing 342 configured to contain the electrical and optical components of nerve stimulator 301 and formed from a bio-compatible material, a battery pack 349 configured to be rechargeable and to receive the recharge via inductive charging while the stimulator 301 is implanted in the patient and further configured to provide power to control unit 343. In some embodiments, control unit 343 is configured to contain electrical and optical components including the communication electronics configured to receive and transmit information from and to the outside of the patient's body and laser-diode driver(s) configured to drive laser diode(s) 344. Laser diode(s) 344 include one or more semiconductor laser diodes (e.g., vertical-cavity surface-emitting lasers (VCSELs) or edge-emitting diode lasers) that are driven by the laser-diode driver(s) and configured to output laser light pulses 309 in the visible and/or infrared wavelength radiation. In some embodiments, laser light pulses 309 enter a light-shaping element 345 that is configured to shape the light pulse and then output the shaped light pulse to waveguide 346. In some embodiments, waveguide 346 is configured to direct the light pulse to a specific location where the light pulse is controlled by light-delivery control 347 to illuminate a specific location on nerve tissue 99 in order to activate a nerve action potential (NAP) in nerve 99. In some embodiments, the heat 308 generated by the control electronics, laser diode drivers, and the communication electronics contained in control unit 343, and by laser diode(s) 344 is removed from nerve stimulator 301 via a heat sink 348 that is thermal-conductively connected to control unit 343 and/or laser diode(s) 344 to transfer the heat 308 from control unit 343 and/or laser diode(s) 344 to heat sink 348. In some embodiments, at least a portion of heat sink 348 extends beyond the outside boundary of nerve stimulator 301 in order for transferred heat 308 to be removed from the heat sink 348 by allowing the heat 308 to transfer and spread away from nerve stimulator 301 and dissipate inside the patient's body. In some other embodiments, heat sink 348 is completely contained within nerve stimulator 301 and makes a thermally conductive contact with the inside surface of nerve stimulator 301 such that the entire container acts as a heat transfer surface to dissipate the heat 308 into the patient's body. In some embodiments, the implant housing 342 is made of a heat-conducting bio-compatible material that has a relatively large thermal mass that readily absorbs short heat spikes from the laser-diode drivers 343 and the laser diodes 344 and then dissipates the heat over a longer period of time to the body of patient 98. In some embodiments, the inner surface of implant housing 342 includes an inside layer (e.g., in some embodiments, 0.5 mm to 3 mm thick) of very-high thermal-conductivity material (e.g., in some embodiments, a layer of materials having sufficient thermal conductivity such as copper, silver, diamond, graphite, graphite fibers, diamond-like carbon (DLC), carbon nanotubes (CNT), silicon carbide, aluminum nitride, and the like, or a hybrid combination of one or more the above-listed materials filled or coated with a high-heat-capacity material such as paraffin wax, polyimide, and the like) that readily absorbs short heat spikes from the pulsed signals (which can be 1 microsecond to 0.01 seconds or somewhat longer in duration), wherein the inner portion is encapsulated by an outer layer of (e.g., in some embodiments, thinner) biocompatible material such as titanium, polyimide-coated CNTs or graphite fibers, or a polymer, which has a lower (but not too low) thermal conductivity to dissipate the heat over a longer period of time (e.g., 10 to 100 seconds) in order to prevent thermal damage to the tissue surrounding implant housing 342.

Figure 4:
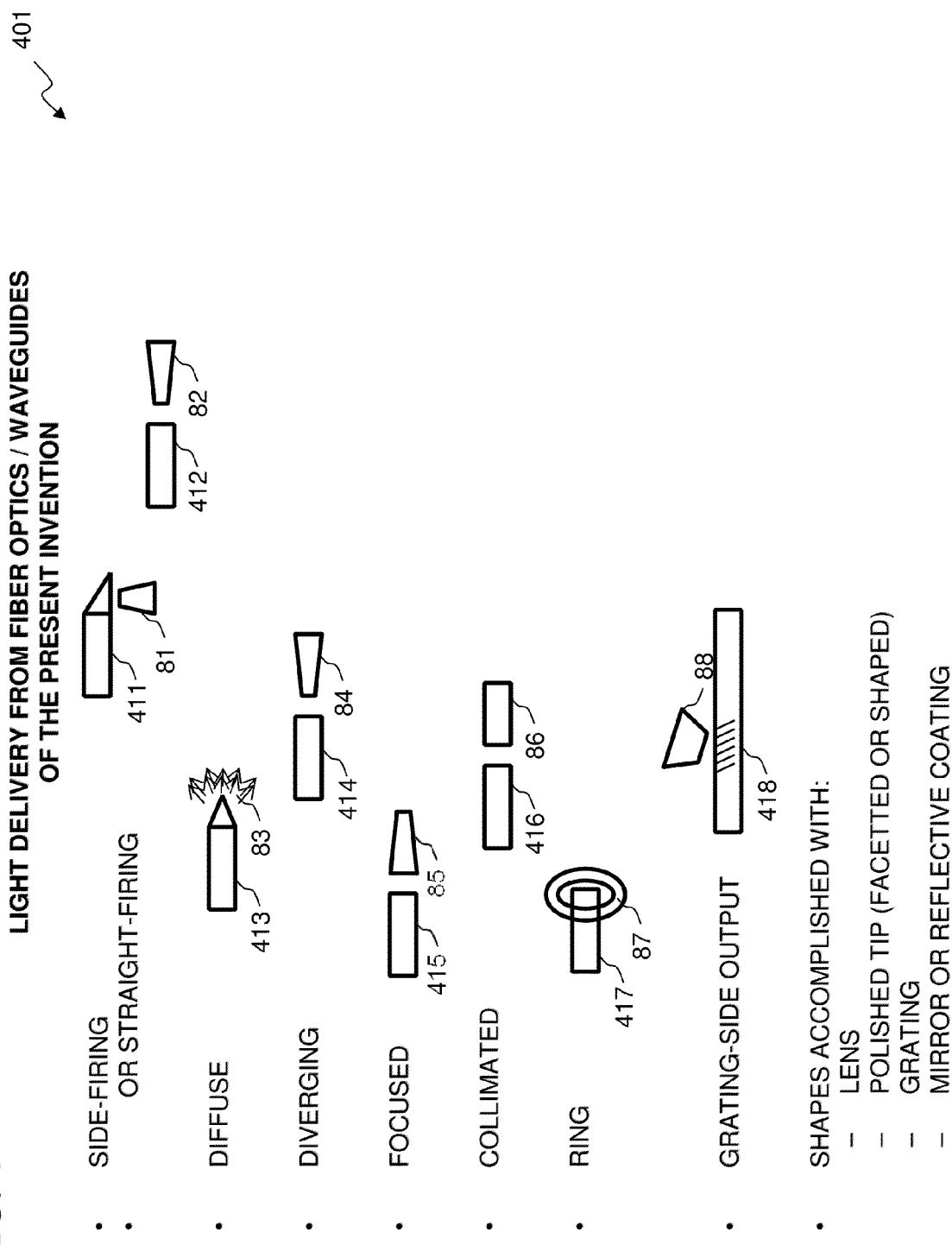
FIG. 4 is a schematic representation of a plurality of light-delivery options 401 from fiber optics/waveguides.

FIG. 4 is a schematic drawing of a plurality of light-delivery options 401 from fiber optics/waveguides. In some embodiments, the shape of the laser beam delivered by the fiber is accomplished with a lens, polished tip (faceted or shaped), grating, mirror or reflective coating, or some combination of the above. Waveguide 411 ends in an angled facet and/or fiber-Bragg grating that reflects or diffracts the light out in a radial or side ("side firing") direction of the waveguide as laser beam 81. Waveguide 412 ends in an end facet that transmits the light out in an axial direction of the waveguide as laser beam 82. Waveguide 413 ends in a conical (as shown), rough or ground "frosted" end that diffuses the light out in a generally axial direction of the waveguide as laser beam 83. Waveguide 414 ends in a lens-type end facet that transmits and diverges the light out in an axial direction of the waveguide as laser beam 84. Waveguide 415 ends in a lens-type end facet that transmits and focuses the light out in an axial direction of the waveguide as laser beam 85. Waveguide 416 ends in a lens-type end facet that transmits and collimates the light out in a parallel beam in an axial direction of the waveguide as laser beam 86. Waveguide 417 ends in an annular lens-type end facet that transmits and focuses the light out in a conical ring centered about an axial direction of the waveguide as laser beam 87. In some such embodiments, the very end facet is polished and coated with a metallic or dielectric-layered reflective structure to better facilitate the ring-shaped output beam 87. Waveguide 418 has a mid-fiber or end-fiber grating that disperses light of a selected wavelength in a radial direction from the side of the fiber of the waveguide as laser beam 88. In some embodiments, a combination of two or more of such features as shown in fiber ends 411, 412, 413, 414, 415, 416, 417 and/or 418 are applied to a single fiber tip to provide a hybrid beam shape combining some aspects of beams 81, 82, 83, 84, 85, 86, 87 and/or 88, respectively. In some embodiments, a bundle having a plurality of such fibers and ends are used in combination to get a plurality of beams and/or a plurality of beam shapes in a small area. In some embodiments, the ends of the plurality of fibers terminate at a plurality of different axial lengths to provide output beams that leave the bundle at different points along the length of the fiber bridle.

Figure 5:
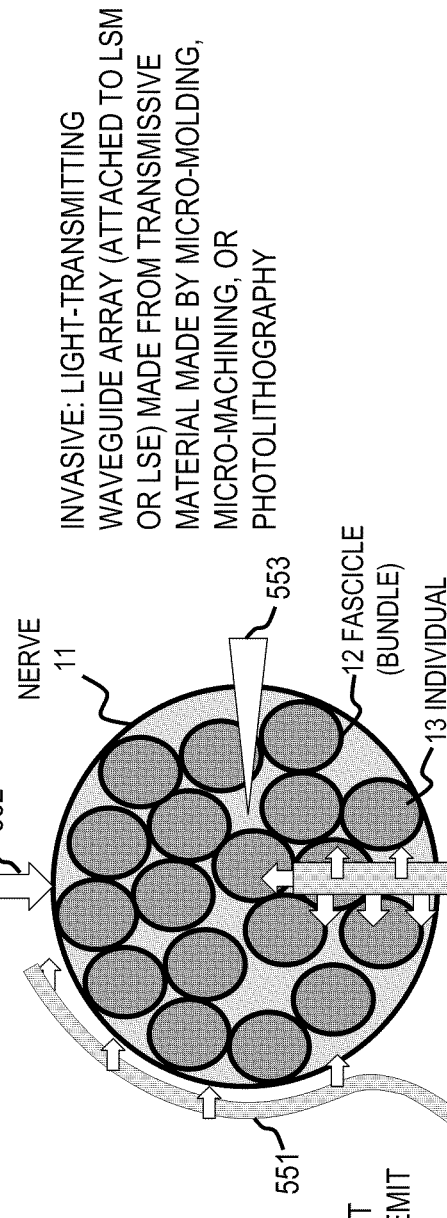
FIG. 5 is a schematic representation of a plurality of nerve stimulator light delivery options 501, according to some embodiments of the present invention.

FIG. 5 is a schematic representation of a plurality of nerve stimulator light delivery options 501, according to some embodiments of the present invention. In some embodiments, the present invention provides a plurality of light-delivery techniques for stimulating nerve 11, specific fascicle 12 (i.e., a specific bundle of nerve fibers 12) within the nerve 11, or even a specific individual nerve fiber 13 within the fascicle 12 in the peripheral nervous system (PNS) and/or the central nervous system (CNS), including cranial nerves, of an animal. In some embodiments, the light-delivery technique is non-invasive to the nerve 11, fascicle 12, and/or nerve fiber 13 because the light-delivery technique does not penetrate the surface of the nerve 11. In some other embodiments, the light-delivery technique is considered invasive to the nerve 11 because waveguides, optical-electrodes, and/or the like penetrate the outer surface of the nerve 11 in order to provide stimulation of fascicles 12 or nerve fibers 13 that are located on the interior of the nerve 11. In some embodiments, a non-invasive direct-light technique is used to stimulate a nerve 11, fascicle 12, and/or nerve fiber 13, or a combination of a nerve 11, fascicle 12, and/or nerve fiber 13 using laser-light beam 552. In some embodiments, non-invasive direct-light technique provides a laser-light beam 552 from a laser-source module (LSM) and/or light-shaping element (LSE), as described above for FIG. 4, to stimulator the nerve 11, fascicle 12, and/or nerve fiber 13. In some embodiments, remote LSM and/or LSE is used to stimulate one or more areas of nerve 11, fascicle 12, and/or nerve fiber 13, wherein light is transmitted via a fiber bundle 551 at the fiber 551/nerve 11 interface, wherein, in some embodiments, the light is emitted from the end of fiber bundle 551 and/or light is emitted from multiple locations along the fiber bundle 551 using inline fiber gratings. In some embodiments, an invasive method is used to stimulate the nerve 11 using a light-transmitting waveguide array 553 implanted into nerve 11, fascicle 12, and/or nerve fiber 13 (attached to LSM or LSE) and formed from transmissive material made by micro-molding, micro-machining, and/or photolithography. In some other embodiments, an additional invasive method is used to stimulate the nerve 11 by implanting a power distribution strip 554 that includes a plurality of light emitting devices that are each capable of stimulating nerve 11, fascicle 12 and/or individual nerve fiber 13. In some embodiments, a combination of light delivery options are used to stimulate nerve 11, fascicle 12, and/or nerve fiber 13 (i.e., in some embodiments, a combination of one or more of the described techniques, including, laser-light beam 552, fiber bundle 551, waveguide array 553, and/or power-distribution strip 554 are used for stimulating nerve 11, fascicle 12, and/or nerve fiber 13).

FIG. 6A is a cross-section end-view schematic representation of a circular-cuff nerve stimulator 601, according to some embodiments of the present invention. In some embodiments, circular-cuff nerve stimulator 601 includes one or more vertical cavity surface emitting lasers (VCSELs) 644 configured to emit light at a wavelength used to stimulate a nerve 11, fascicle 12, or individual nerve fiber 13, one or more driver integrated circuits 643 that are configured to provide the driving power required to operate the VCSELs 644, power-and-control electronics 663 configured to provide power to the driver ICs and control which VCSELs 644 are emitting optical radiation and therefore providing stimulation to the nerve 11, fascicle 12, or individual nerve fiber 13. In some embodiments, circular-cuff nerve stimulator 601 includes a biocompatible ring 661 holding VCSELs 644, circuit routing (power and control), and VCSEL driver ICs 643, and is wrapped around or surrounds one or more nerves 11 and the VCSELs are used to stimulate specific areas in nerve 11, specific fascicles 12, and/or even specific individual nerve fibers 13, or a combination of the three. In some embodiments, the control electronics that control the stimulation signals are mounted with or integrated with the VCSEL drivers 643.

In some such embodiments, each VCSEL emits a somewhat narrow cone-shaped or substantially collimated beam that stimulates only a relatively small amount of tissue or number of nerve fibers. In some embodiments, the narrow beam illuminates a plurality of nerves along its axial length, but wherein pulses from a single such narrow beam are insufficient to trigger a NAP in any one of these plurality of illuminated nerve fibers. Only when a plurality of such narrow beams intersect at one or more nerve fibers, such that optical pulses from the plurality of beams are delivered within a sufficiently short amount of time to the intersection point or volume of tissue and thus the combination of intersecting pulses (close enough in space and in time) are sufficient to trigger a NAP.

FIG. 6B is a side-view schematic representation of an encircling-cuff nerve stimulator 602, including control electronics 663, according to some embodiments of the present invention. In some embodiments, encircling-cuff nerve stimulator 602 is substantially similar to circular-cuff nerve stimulator 601, except that the control electronics 663 of encircling-cuff nerve stimulator 602 are not integrated with the VCSEL drivers as shown in FIG. 6A for circular-cuff nerve stimulator 601, but rather are located at a distal end of electrical cable 662 (which allows the heat from the electronics drivers to be dissipated over a larger area, thus reducing patient discomfort and the chance for injury). In some embodiments, the VCSEL drivers 643 are also located distal to the nerve being stimulated (e.g., in some embodiments, these drivers are located with or integrated with the control electronics 664). Electrical signals in cable 662 connect control electronics 663 to driver integrated circuits 643. In some embodiments, control electronics 663 are in a biocompatible housing implanted into the patient. In other embodiments, control electronics 663 are partially implanted into the patient such that the control electronics 663 is not completely contained within the patient's body and at least part of control electronics 663 control signals and/or power crosses the patient body boundary (e.g., by wireless signal and power transmission), and at least part of control electronics 663 resides external to the patient.

In some embodiments, the electrical signals in cable 662 are multiplexed to reduce the number of wires and/or size of the cable connecting the control electronics to the VCSEL drivers 643. In some embodiments, the electrical signals in cable 662 are time-division multiplexed or serially multiplexed. In some embodiments, the electrical signals in cable 662 are multiplexed by being encoded, such as row-column multiplexed (e.g., where the cathodes of the VCSELs are connected in a plurality of columns and the anodes are connected in a plurality of rows). In some other embodiments, other commonly known methods of multiplexing are use to reduce the number of wires and/or size of the cable connecting the control electronics to the VCSEL drivers 643. In some such embodiments, VCSEL-driver circuit 643 includes a demultiplexor and/or decoder that uses the information in signals from cable 662 to activate selected ones of the VCSELs at the appropriate times to trigger the desired response.

In some embodiments, the number of individually-controllable VCSELs selectively emitting optical radiation is greater or much greater than the number that will be end up being used in normal operation. With a large number of VCSEL elements, empirical testing can be used, in some embodiments, to determine which individual VCSEL elements or combinations of VCSEL elements stimulate the desired response from a fascicle or nerve fiber. With such empirical testing, it is not necessary to precisely locate unit 602 relative to any one or more nerves in a tissue nor is it required to detect a NAP in a particular nerve near the stimulation; rather, the device is implemented with many more VCSEL elements than the number of nerves to be stimulated, it is implanted or placed in an approximate position, and then tested to obtain stored mapping information (e.g., by emitting a light pulse from one or more light emitters, and determining which, if any, response was triggered (e.g., by observing muscle movement or inquiring of the patient what if any sensation was felt), and storing into a computer memory which response(s) was generated by light and/or electrical signals from which emitters and/or electrodes), then using that stored information as a map (between later-detected conditions for which responses are to be triggered, and which emitters and/or electrodes are to be activated to evoke the respective response for the detected condition).

In some embodiments, a plurality of circular-cuff nerve stimulators 602 are used and connected by electrical signals 662 to one or more sets of control electronics 663. In some embodiments, a plurality of circular-cuff nerve stimulators 602 are placed along one or more nerves 11.

In some embodiments, encircling-cuff nerve stimulator unit 602 is flexible and spiral shaped to allow the encircling-cuff to be inserted around the nerve 11 by twisting the spiral-shaped nerve stimulators 602 around the nerve. In some embodiments, flexible spiral-shaped nerve stimulators provide a close fit over a wide variety of nerve geometries without pinching the nerve and this close fit also provides for a more stable (e.g., less chance of movement) arrangement between the nerve stimulator device and the nerve. In some embodiments, the spiral-shaped nerve stimulators provide for several loops around the nerve in a helical arrangement providing additional VCSELs 644 to optionally or selectively stimulate a plurality of nerve(s) 11, fascicles 12, and/or nerve fibers 13.

In some embodiments, power levels for a single VCSEL are low enough not to stimulate a NAP, while the power level resulting from substantially simultaneous light pulses from a plurality of VCSELs is used to stimulate a NAP. To stimulate fascicles, and/or nerve fibers that happen to be located deeper within a nerve tissue, in some embodiments it is desirable to limit the output power level of a single VCSEL to a value that is below the level that would stimulate a NAP.

In some embodiments, a plurality of VCSELs 'dynamic focusing' laser energy deeper into the nerve tissue, i.e., 'dynamic focusing' laser energy is the intersection of the simultaneously delivered pulses of light from a plurality of VCSELs on a fascicle or nerve fiber. In some embodiments, a plurality of VCSELs each have differently-focused tips or output optics (e.g., waveguide 415 described above in FIG. 4) such that a plurality of VCSELs, each focused at one of a variety of focal lengths can be separately activated to achieve different depths at which the light simulation becomes focused enough to trigger a NAP. With a number of VCSELs each focused at a variety of focal lengths, empirical testing can be used, in some embodiments, to determine which individual VCSEL stimulates the desired response from a fascicle or nerve fiber. (Note that with such empirical testing, it is not necessary to precisely locate unit 602 relative to any one or more nerves in a tissue; rather, the device is implemented with many more VCSEL elements than the number of nerves to be stimulated, and testing (e.g., emitting a light pulse from one or more light emitters, and determining which, if any response was triggered, and storing into a computer memory which response(s) was generated by which emitters, then using that stored information as a map as to which emitters to activate to evoke which response) is used to determine the VCSEL element to use to stimulate a desired response.) In some embodiments, a combination of 'dynamic focusing' a plurality of VCSELs and lens focusing at a variety of focal lengths are used to selectively stimulate fascicles and/or nerve fibers deep within a nerve 11 without stimulating non-selected fascicles or nerve fibers closer to the epineurium of the nerve.

Figures 7A, 7B:
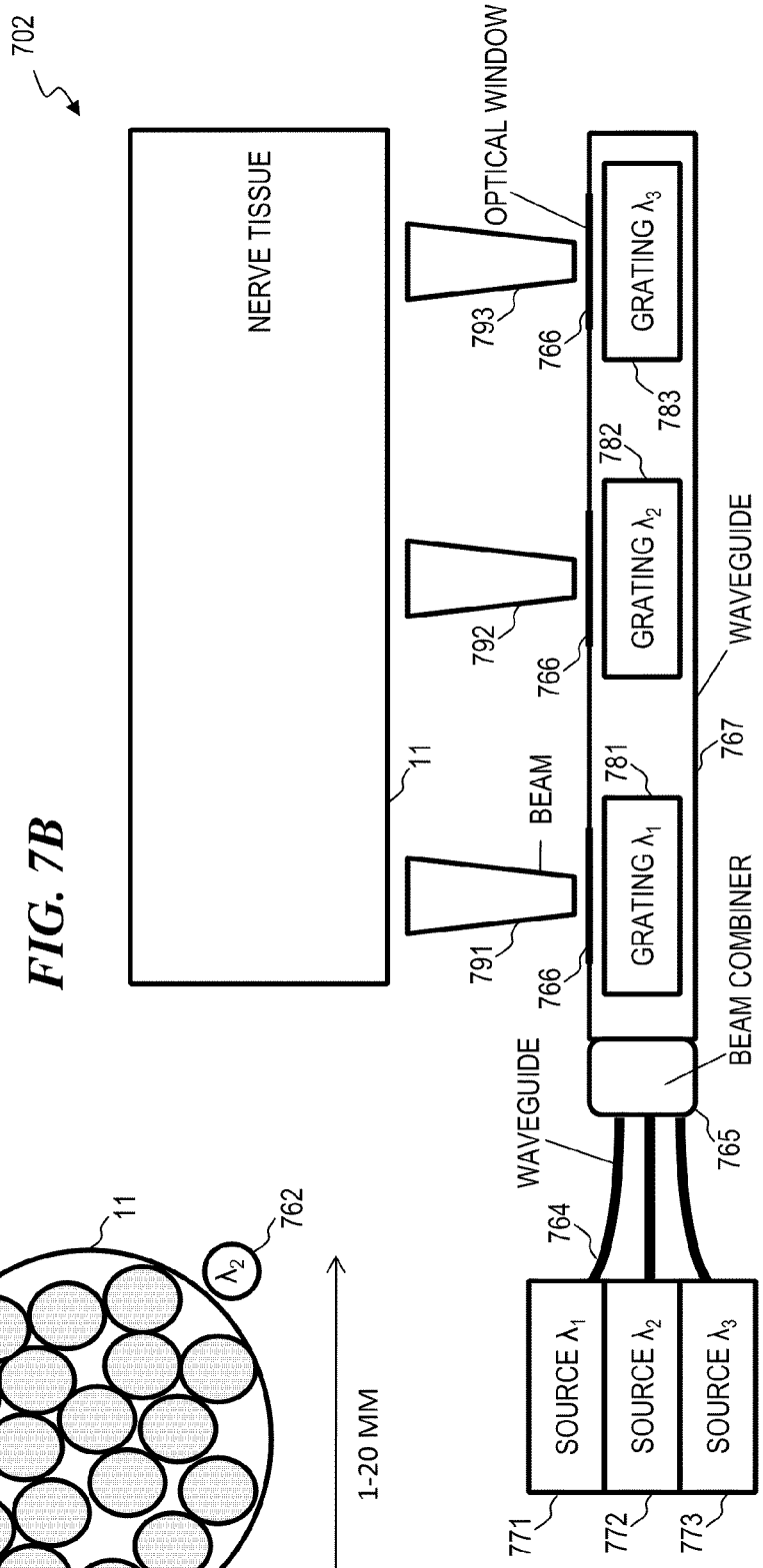
FIG. 7A is a cross-section end-view schematic representation of a multiple-wavelength nerve stimulator 701, according to some embodiments of the present invention.
FIG. 7B is a side-view schematic representation of a multiple-wavelength nerve stimulator 702, according to some embodiments of the present invention.

FIG. 7A is a cross-section end-view schematic representation of a multiple-wavelength nerve stimulator 701, according to some embodiments of the present invention. In some embodiments, multiple-wavelength nerve stimulator 701 includes one or more optical fibers (761, 762, 763) each configured to transmit a different wavelength of laser light ($\lambda_1, \lambda_2, \lambda_3$, respectively) to stimulate nerve 11 and each optical fiber (761, 762, 763) includes an output feature (such as a fiber grating as shown schematically in fiber 418), each configured or tuned to output, at each fiber's grating, termination or window (e.g., such as shown in FIG. 4), one of the specific laser-light wavelengths ($\lambda_1, \lambda_2, \lambda_3$, respectively) traveling through the optical fiber (761, 762, 763). In some embodiments, different wavelengths of laser-light are used to penetrate to different depths with the nerve 11. In some embodiments, an output lens on each fiber having one of a plurality of focal lengths is used to obtain one of a plurality of tissue-penetration depths (in that only when the light is at the focal point will the light have sufficient power-per-area to trigger a NAP), in order that beams emitted from each of a plurality of fibers trigger NAPs in different nerves. In some embodiments, a testing algorithm is used to determine which response is triggered by each of a plurality of fibers and a mapping of which fiber triggers which response is programmed or stored into the controller electronics in order to properly stimulate one of a plurality of responses when desired. In some embodiments, the fiber grating in optical fiber 761 is tuned to laser-light wavelength $\lambda_1$ and the grating reflects the laser-light traveling in optical fiber 761 causing the laser light to exit the fiber such that the emitted laser light stimulates a portion of nerve 11 (e.g., one or more fascicles 12 and/or one or more axons 13). In some embodiments, the fiber grating in optical fiber 762 is tuned to laser-light wavelength $\lambda_2$ and the grating reflects the laser-light traveling in optical fiber 762 causing the laser-light to exit the fiber such that the emitted laser light stimulates a portion of nerve 11 (e.g., one or more fascicles 12 and/or one or more axons 13). In some embodiments, the fiber grating in optical fiber 763 is tuned to laser-light wavelength $\lambda_3$ and the grating reflects the laser light traveling in optical fiber 763 causing the laser light to exit the fiber such that the emitted laser light stimulates a portion of nerve 11 (e.g., one or more fascicles 12 and/or one or more axons 13). In some embodiments, the each optical fiber includes a single fiber grating to reflect the laser light onto the nerve and in other embodiments each optical fiber includes a plurality of fiber gratings to such that each optical fiber can stimulate the nerve in multiple positions along the optical fiber. In some embodiments, the optical fibers are spirally wound along the length of the nerve or are wound in a circular manner around the nerve.

In some embodiments, the one or more optical fibers (761, 762, 763) include faceted ends (e.g., cleaved, lensed or polished ends), wherein the face or facet of each faceted end of the one or more optical fibers (761, 762, 763) reflects and/or focuses the laser-light that was traveling in an axial direction in the one or more optical fibers (761, 762, 763) causing the laser light to exit the fiber in a radial or angled direction such that the emitted laser light stimulates a portion of nerve 11 (e.g., one or more fascicles 12 and/or one or more axons 13)

FIG. 7B is a side-view schematic representation of a multiple-wavelength nerve stimulator 702, according to some embodiments of the present invention. In some embodiments, multiple-wavelength nerve stimulator 702 includes one or more laser-beam sources (771, 772, 773) each having a different wavelength ($\lambda_1, \lambda_2, \lambda_3$, respectively) and each being optically connected by a waveguide 764 to a beam combiner 765 where the laser light of each laser source (771, 772, 773) is combined and transmitted to optical waveguide 767. In some embodiments, different wavelengths of laser-light are used to stimulate different portions of nerve 11 while sharing a common optical waveguide (e.g., if different wavelengths have different penetration depths in a given tissue, in some embodiments, those wavelengths with short penetration depth stimulate tissue nearer the surface and those wavelengths with longer penetration depth stimulate tissue further from the surface). In some embodiments, optical waveguide 767 is configured to receive the laser light having multiple wavelengths ($\lambda_1, \lambda_2, \lambda_3$, respectively) and fiber gratings (grating 781, grating 782, and grating 783, respectively) are placed, as shown in FIG. 7B, such that different wavelengths of light are emitted from the waveguide through optical windows 766 generating optical beams 791, 792, and 793, respectively, located at different axial locations along a nerve 11. The fiber gratings and optical windows are placed, e.g., as shown in FIG. 7B, such that different wavelengths emitted from the waveguide are located at different transverse locations along the length of the nerve, and in some other embodiments, a combination of multiple wavelengths are emitted both axially and transversely locations are provided as a function of the wavelength. In some embodiments, the optical waveguide 767 is spirally wound along a length of the nerve or is wound in a circular manner around the nerve and the optical gratings are distributed in a circular or helical/spiral cuff configuration around the nerve.

FIG. 7C is a cross-section end-view schematic representation of a multiple-focal-length nerve stimulator 703, according to some embodiments of the present invention. In some embodiments, a plurality of VCSELs each have differently-focused tips or output optics (e.g., waveguide 415 described above in FIG. 4) such that a plurality of VCSELs (e.g., 751, 752, 753, 754, 755, 756 and 757), each focused at one of a variety of focal lengths can be separately activated to achieve different depths at which the light simulation becomes focused enough to trigger a NAP. In some embodiments, the emitters of the plurality of VCSELs are located around and in close proximity with the nerve 11 (e.g., arranged around nerve 11 as described above in FIGS. 6A and 6B). In some embodiments, many more VCSELs/lenses are used than demonstrated in FIG. 7C. With a number of VCSELs each focused at a variety of focal lengths, empirical testing can be used, in some embodiments, to determine which individual VCSEL stimulates the desired response from a fascicle or nerve fiber. Note that with such empirical testing, it is not necessary to precisely locate unit 703 relative to any one or more nerves in a tissue; rather, the device is implemented with many more VCSEL elements than the number of nerves to be stimulated, and testing is used to determine the VCSEL element to use to stimulate a desired response.

Thus, in some embodiments, the present invention provides a method that includes selectively controlling light signals having a wavelength and having a pulse duration from each of a plurality of vertical cavity surface-emitting lasers (VCSELs) including a first VCSEL 751 and a second VCSEL 752; focusing the light from the first VCSEL 751 relatively more deeply into first tissue 11 of the patient (e.g., 98 of FIG. 3), in order to stimulate the NAP in a first nerve fiber 711 that is deeper in the first tissue 11 than a second nerve fiber 712 that is at or nearer to a surface-layer depth in the first tissue 11 adjacent the first VCSEL 751 and second VCSEL 752 without stimulating a NAP in the second nerve fiber 712 due to the light from the first VCSEL 751; and focusing the light from the second VCSEL 752 to focus less deeply into the first tissue 11 of the patient, in order to stimulate the NAP in the second nerve 712 (which is at a shallower depth in the first tissue) adjacent the first VCSEL 751 and second VCSEL 752 without stimulating a NAP in the deeper first nerve 711 due to the light from the second VCSEL 752.

In other embodiments, the focused light from each VCSEL 751, 752, 753 is insufficient alone to trigger a NAP in nerves 711, 712, or 713, but when a pulse is emitted from VCSEL 751 substantially simultaneously with a pulse emitted from VCSEL 752, the light from VCSEL 751 focused on nerve fiber 711 and the extra light from VCSEL 752 (perhaps not focused on nerve fiber 711) are sufficient to trigger a NAP in nerve fiber 711 but, due to their various directions and focal-point distances and locations would perhaps not trigger a NAP in nerve fiber 712.

In still other embodiments, the focused light from each VCSEL 754, 755, 756, 757 are each insufficient alone to trigger a NAP in nerve fibers 714 and 715, but a plurality of VCSELs (e.g., the pair 754 and 755 each focused and pointed to converge into a single nerve fiber 714, or the pair 756 and 757 each focused and pointed to converge into another single nerve fiber 715. When stimulation light is emitted and focused by both VCSELs 754 and 755, that combined light will trigger a NAP in nerve fiber 714, and similarly when stimulation light is emitted and focused by both VCSELs 756 and 757, that combined light will trigger a NAP in nerve fiber 715.

In some embodiments, an electrical-signal controller (such as shown in FIGS. 2A, 2B, 2C and 2D) is added to the embodiments of any of the other Figures herein, such that a combination of electrical stimulation and optical stimulation (wherein either alone is insufficient to trigger a NAP) is used wherein when applied in combination the combination of electrical stimulation and optical stimulation is sufficient to trigger a NAP. In some such embodiments, the optical stimulation includes stimulation light from a plurality of VCSELs that is emitted simultaneously or non-simultaneously but close enough in time so as to synergistically combine with each other and with the electrical stimulation to reliably trigger a NAP.

Figure 1A:
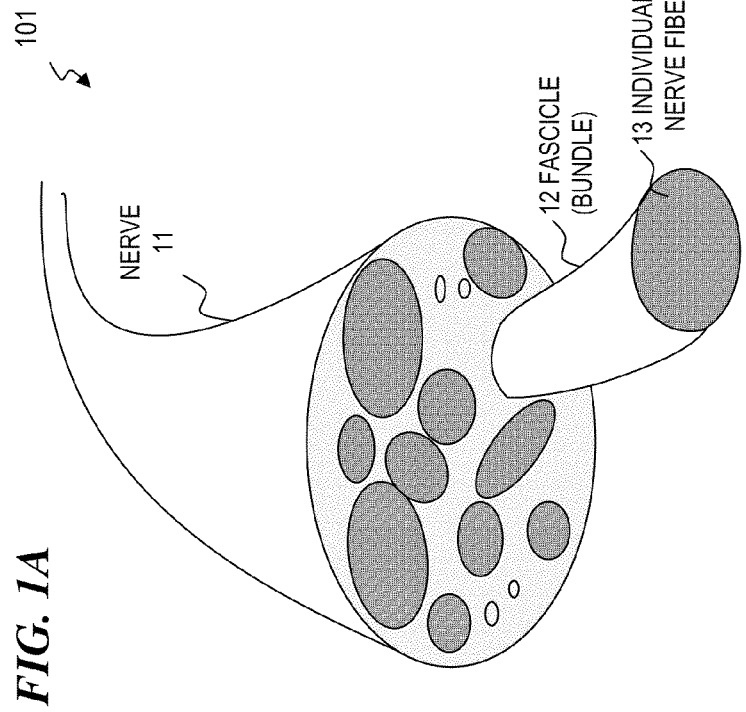
FIG. 1A is a schematic diagram 101 of a nerve 11.

FIGS. 7D1, 7D2, and D3 are cross-section end-view schematic representations of a multiple-intersection nerve stimulator 704, according to some embodiments of the present invention. In some embodiments, power levels for a single VCSEL are low enough not to stimulate a NAP, while the power level resulting from substantially simultaneous collimated light pulses from a plurality of VCSELs is used to stimulate a NAP. To stimulate fascicles, and/or nerve fibers that happen to be located deeper within a nerve tissue, in some embodiments it is desirable to limit the output power level of a single VCSEL to a value that is below the level that would stimulate a NAP. In a first example, FIG. 7D1 is a schematic representation where the combination of individual VCSELs 741, individual VCSELs 742, and individual VCSEL 743, simultaneously deliver sufficient collimated pulse light power to fascicles and/or nerve fibers 714 to stimulate and NAP. Pulse light power from each individual VCSEL 741, 742, and 743 is insufficient to stimulate a NAP, thus not stimulating other fascicles and/or nerve fibers with the nerve 11.

In a second example, FIG. 7D2 is a schematic representation where the combination of individual VCSELs 741, individual VCSELs 742, individual VCSELs 743, and individual VCSEL 744, simultaneously deliver sufficient collimated pulse light power to fascicles and/or nerve fibers 714 to stimulate and NAP. Pulse light power from each individual VCSEL 741, 742, 743, and 744 is insufficient to stimulate a NAP, thus not stimulating other fascicles and/or nerve fibers with the nerve tissue 11.

In a third example, FIG. 7D3 is a schematic representation where the combination of individual VCSELs 741, individual VCSELs 742, individual VCSELs 743, and individual VCSEL 744, simultaneously deliver sufficient collimated pulse light power to fascicles and/or nerve fibers 715 to stimulate and NAP. Pulse light power from each individual VCSEL 741, 742, 743, and 744 is insufficient to stimulate a NAP, thus not stimulating other fascicles and/or nerve fibers with the nerve tissue 11. In some embodiments, the number of VCSELs used is much greater than shown in these examples, but it demonstrated by these examples how individual fascicles and/or nerve fibers can be stimulated using a plurality of VCSELs located around and in close proximity with the nerve 11 (e.g., arranged around nerve 11 as described above in FIGS. 6A and 6B). With a combination of VCSELs intersecting at a variety of points within a nerve 11, empirical testing can be used, in some embodiments, to determine which combination of VCSELs stimulate the desired response from a fascicle or nerve fiber. Note that with such empirical testing, it is not necessary to precisely locate unit 704 relative to any one or more nerves in a bundle; rather, the device is implemented with many more VCSEL elements than the number of nerves to be stimulated, and testing is used to determine the VCSEL element to use to stimulate a desired response.

Figure 8:
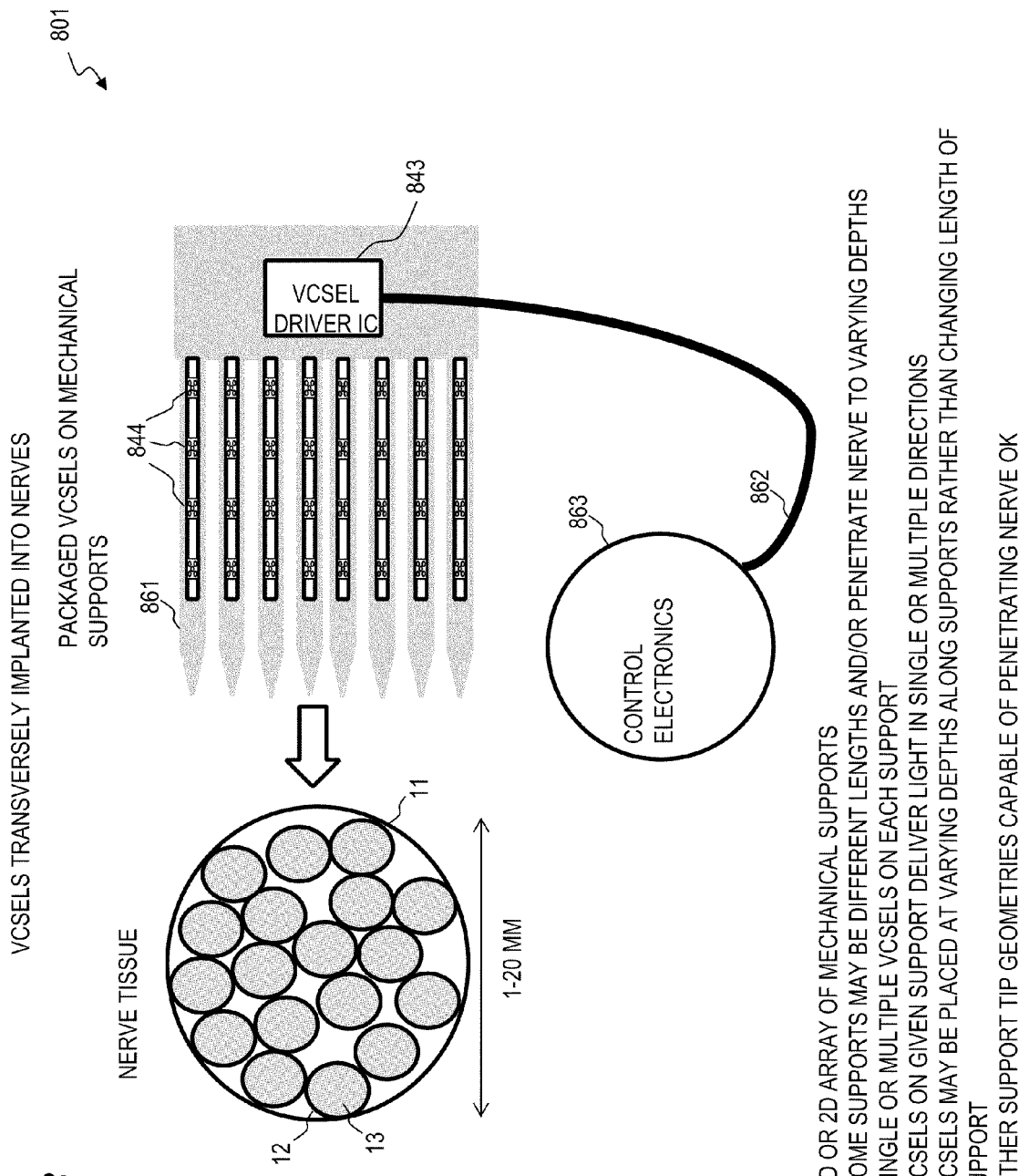
FIG. 8 is a cross-section end-view schematic representation of a transversely-implanted nerve stimulator 801, according to some embodiments of the present invention.

FIG. 8 is a cross-section end-view schematic representation of a transversely-implanted nerve stimulator 801, according to some embodiments of the present invention. In some embodiments, a one-dimensional (1D-e.g., a single needle-like projection) array or a two-dimensional ("2D"-e.g., a row of parallel needle-like projections as shown in FIG. 8) array of mechanical supports 861 are used to support a plurality of VCSELs 844, wherein each support locates each of its emitters at a different one of a plurality of depths within the group of nerves within nerve tissue 11 such that the light from each VCSEL 844 is emitted at a different nerve within the group. In some embodiments, the 1D or 2D array of supports is gently "teased" through the nerve bundle so as to not damage the nerves during the insertion. In some embodiments, some of the supports 861 may be different lengths than the others and/or penetrate group of nerves in the nerve tissue to varying depths. In some embodiments, single or multiple VCSELs 844 are packaged on each support. In some embodiments, VCSELs on given support deliver light in a single radial direction (e.g., VCSELs in a line along one side of the support emitting substantially parallel beams in a single radial direction) or in multiple directions (e.g., VCSELs located on multiple sides of the support emitting non-parallel beams in a plurality of radial directions). In some embodiments, VCSELs may be placed at fixed depths along supports and the supports are inserted to different depths (like changing the lengths of the support extending from the VCSEL-driver integrated circuit (IC) 843). In some embodiments, other support-tip geometries capable of penetrating nerve are used. In other embodiments, the VCSELs are located distal from the supports 861, and optical fibers or other light-guiding structures carry the light from the VCSELs to the emitters on the needle-like supports 861, which are inserted within the group of nerves in nerve tissue 11. In some embodiments, electrical signals in cable 862 connect control electronics 863 to driver integrated circuit(s) 843. In some embodiments, control electronics 863 are in a biocompatible housing implanted into the patient. In other embodiments, control electronics 863 are partially implanted into the patient such that the control electronics 863 is not completely contained within the patient's body and at least part of control electronics 863 control signals and/or power crosses the patient body boundary (e.g., by wireless signal and power transmission), and at least part of control electronics 863 resides external to the patient.

In some embodiments, the electrical signals in cable 862 are multiplexed to reduce the number of wires and/or size of the cable connecting the control electronics 863 to the VCSEL-driver circuit(s) 843. In some embodiments, the electrical signals in cable 862 are time-division multiplexed or serially multiplexed. In some embodiments, the electrical signals in cable 862 are multiplexed by being encoded, such as row-column multiplexed (e.g., where the cathodes of the VCSELs are connected in a plurality of columns and the anodes are connected in a plurality of rows). In some other embodiments, other commonly known methods of multiplexing are use to reduce the number of wires and/or size of the cable connecting the control electronics to the VCSEL drivers 843. In some such embodiments, VCSEL-driver circuit 843 includes a demultiplexor and/or decoder that uses the information in signals from cable 862 to activate selected ones of the VCSELs at the appropriate times to trigger the desired response.

In some embodiments, the number of individually-controllable VCSELs selectively emitting optical radiation is greater or much greater than the number of VCSELs that will be end up being used in normal operation. In some embodiments, the number of supports 861 is greater than the number that will be end up being used in normal operation. With a large number of VCSEL elements and/or supports 861, empirical testing can be used, in some embodiments, to determine which individual VCSEL elements or combinations of VCSEL elements stimulate the desired response from a fascicle or nerve fiber. With such empirical testing, it is not necessary to precisely locate unit 801 relative to any one or more nerves in a tissue; rather, the device is implemented with more or many more VCSEL elements and supports 861 than the number of nerves to be stimulated, and testing (e.g., emitting a light pulse from one or more light emitters, and determining which, if any response was triggered (e.g., by observing muscle movement or inquiring of the patient what if any sensation was felt), and storing into a computer memory which response(s) was generated by which emitters and/or electrodes), then using that stored information as a map (between later-detected conditions for which responses are to be triggered, and which emitters and/or electrodes are to be activated to evoke the respective response for the detected condition).

FIG. 9A is a block diagram of a computerized system 901 for determining a reaction of the nerve tissue through empirical testing of the light-emitting structure and power levels. In some embodiments, computer system 904 is connected by a wired and/or wireless interface 920 to the control electronics 863. In some embodiments, the present invention provides a method for a computerized method of determining which combinations of VCSELs, power levels, and wavelengths cause a reaction in the patient and storing that information for future reference and stimulation. This computerized method includes iteratively applying a plurality of different combinations of stimulation signals to the patient and acquiring data as to one or more responses that were caused by each combination of stimulation signals, providing specifications of a plurality of desired responses to each of a plurality of conditions, correlating and mapping the specifications of a plurality of desired responses with the data as to the responses that were caused by each combination of stimulation signals, and storing a resulting mapping in a computer-readable memory, determining that one of the plurality of conditions has occurred, and based on the stored mapping and the determination that one of the plurality of conditions has occurred, driving the corresponding combination of stimulations signals to evoke the desired response to the condition in the patient. In some embodiments, the method also provides input device(s) 905 connected through an interface 906 as part of computer system 904 to provide external user or operator input as to the responses that were caused by each combination of stimulation signals.

FIG. 9B is a block diagram of a computerized method 902 for determining a reaction of the nerve tissue through empirical testing of the light-emitting structure, power levels and/or electrical preconditioning, and then using the mapping obtained from the testing to control a nerve stimulator. In some embodiments, method 902 includes starting at block 921, then implanting or placing the nerve-stimulation device such that the optical- and/or electrical-signal deliver is at an efficacious location near or against the nerve tissue to be stimulated (e.g., as described above). At block 923, the method causes the device to deliver a combination of a plurality of optical signals within a time period that is short enough that the combination will trigger a NAP. The term "a time period that is short enough" means that the optical signals are either applied simultaneously, at least partially overlapped in time, or successively (but not simultaneously) but within a period of time that is short enough that the pulses effect on tissue combines sufficiently to trigger a NAP. In some embodiments, either signal alone is insufficient to trigger a NAP, while in other embodiments, one or both signals may at least sometimes trigger a NAP. In some embodiments, in addition to the plurality of optical signals, an electrical-sensitization signal must be applied before or during the time period within which the combination of optical signals is applied. At block 924, the evoked NAP or other response is sensed to generate a sense signal or sense data, which is then analyzed to determine which physiological response it was, and a mapping indication (of which stimulation caused which response) is stored in a computer-accessible memory or the equivalent. If a sufficient number and type of the possible responses have been successfully evoked, the YES exit from block 925 is taken and the method continues at block 931, otherwise the combination of specified outputs is changed and the method goes back to block 923 and the method iterates until a sufficient set of responses have been mapped. Of course, if all possible combinations of stimulation signals have been tried, the method could go to block 931, or the implantation could be repositioned by going to block 922.

At block 931, the method includes receiving one or more environmental and/or patient-physiology signals or data (e.g., from an environmental sensor, and/or from a patient-physiology sensor). At block 932, the signals and/or data are analyzed to determine which response is desired or needed, and at block 933, the method includes mapping the needed response indication to a set of stimulation-signal outputs that are needed to evoke that response (e.g., the set of one or more NAPs that should be triggered). Typically the method then always goes back to block 931 to wait for another sensed event, however, in some embodiments, the method determines that the required sensing and simulations needed have been completed, and the method goes to the end block 935.

In some embodiments (such as described in U.S. Pat. No. 7,736,382 issued Jun. 15, 2010, which is incorporated herein by reference), in those instances where an array- or matrix-type configuration is used software is used to isolate an isomorphism between a particular light-emitting structure and certain nerve tissues. Put another way, once a reaction of a particular nerve tissue is determined, software can be used to determine which light-emitting structure and power levels actually caused the reaction on the part of the nerve tissue. The algorithm to determine which light-emitting structure and power levels caused a reaction could be a simple sequential-search algorithm whereby each light-emitting structure individually emits light by itself at various power levels and a nerve-tissue reaction is determined to be present or absent, or it could be a more sophisticated binary-search algorithm whereby, for example, an array of light-emitting optical-fiber structures is divided in half, each sub-array tested individually to determine whether a nerve-tissue reaction is present or absent, and if one sub-array is indeed associated with a nerve-tissue reaction then that sub-array is again divided in half and the process repeated. Some embodiments use algorithms to search array-like structures and matrices, such as are well known in the art. (See *Algorithms in C++: Parts 1-4 3$^{rd}$ Edition*, by Robert Sedgewick, Addison Wesley 1998.) In some embodiments, stimulated nerve tissue reactions In some embodiments, the present invention provides a method for activating or stimulating neurons (peripheral or central projections) of a nerve or nerve bundle of a patient to provide touch, feeling, temperature, pain, or motor sensations for the patient. In some embodiments, the method provides stimulation or inhibition of nerve signals for treatment of pain, obesity, epilepsy, depression, and the like. In some embodiments, the method provides therapy that restores motor-nerve (muscle-control) signals from the brain towards muscles or prostheses (through NAP stimulation, inhibition, or both), for motor control as well as treatment of incontinence, irregular heart rhythms, tremors or twitches, and the like. In some embodiments, the method includes delivering light signals, or both light and electrical signals, to a plurality of neurons of the nerves of the PNS and/or CNS of the patient.

In some embodiments, the delivering of light signals includes delivering the light signals to peripheral projections of the neurons. In some embodiments, the delivering of light signals includes delivering the light signals to central portions of the neurons.

In some embodiments, the delivering of light signals includes delivering light (having one or more ultraviolet, visible, and/or infrared wavelengths) from a laser or other light source. In some embodiments, the delivering of light signals includes delivering light from a VCSEL. In some embodiments, the delivering of light signals includes delivering light from a quantum-dot laser. In some embodiments, the delivering of light signals includes delivering light from an edge-emitting laser. In some embodiments, the delivering of light signals includes delivering light from a non-laser light-emitting device (LED). In some embodiments, the delivering of light signals includes delivering light from a super-luminescent LED or other such light source.

Some embodiments further include delivering an electrical signal to a plurality of neurons of the nerves or nerve bundles of the PNS and CNS.

In some embodiments, the delivering of the light signals includes obtaining a plurality of light signals from one or more laser light sources and delivering the obtained light signals to discrete portions of excitable tissues, wherein the responses triggered by the light signals are interpretable by the patient's brain as sensory responses.

In some embodiments, the delivering of the light signals further includes selectively controlling the light signals to optically stimulate the neurons in order to control nerve action potentials (NAPs) produced by the one or more nerves. In some embodiments, the selectively controlling the light signals includes controlling a pulse width of the plurality of light signals. In some embodiments, the selectively controlling the light signals includes controlling a pulse repetition rate of the plurality of light signals. In some embodiments, the selectively controlling the light signals includes controlling a pulse shape of the plurality of light signals. In some embodiments, the selectively controlling the light signals includes controlling a DC background amount of light intensity of the plurality of light signals. In some embodiments, the selectively controlling the light signals includes controlling a pre-charge amount of light intensity followed by a trigger amount of light intensity of the plurality of light signals. In some embodiments, the selectively controlling the light signals includes controlling the light signals to increase a frequency of the NAPs produced by the one or more nerves that would otherwise occur without the plurality of light signals.

In some embodiments, the method further includes applying a precharge current of electrical energy that is followed by a trigger amount of pulsed light intensity of the plurality of light signals.

In some embodiments, the obtaining the plurality of light signals includes implanting a self-contained battery-powered laser-light-generation device and obtaining the plurality of light signals from the battery-powered laser-light-generation device.

In some embodiments, the delivering the plurality of light signals to the plurality of neurons of nerves of the PNS and/or CNS includes positioning a delivery end of one or more fibers against one or more neurons of the PNS and/or CNS and using one or more optical fibers to guide the light signals from a laser source to the one or more neurons.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

In some embodiments, the present invention provides a method that includes obtaining a plurality of light signals from one or more laser light sources; delivering the plurality of light signals to a plurality of nerve pathways in the PNS and/or CNS of a living animal; and selectively controlling the plurality of light signals to optically stimulate the plurality of nerve pathways in order to control nerve action potentials (NAPs) produced by the plurality of nerve pathways. In some embodiments, the plurality of nerve pathways in the PNS and/or CNS includes spinal nerves pathways, cranial nerves pathways, brainstem pathways, spinal cord pathways, and the like.

In some embodiments, the living animal is a human person. In some embodiments, the living animal is a large non-human animal, e.g., a race horse, a Scottish Highland cow, a Black Guinea hog, an elephant, or the like. In some embodiments, the living animal is a small non-human animal, e.g., a dog, a cat, a Nigerian pygmy goat, a rodent or the like.

In some embodiments, the selectively controlling the light signals includes controlling a pulse width of the plurality of light signals.

In some embodiments, the selectively controlling the light signals includes controlling a duty cycle of the plurality of light signals.

In some embodiments, the selectively controlling the light signals includes controlling an on-time and an off-time of the plurality of light signals.

In some embodiments, the selectively controlling the light signals includes controlling a wavelength of the plurality of light signals.

In some embodiments, the selectively controlling the light signals includes controlling a pulse repetition rate of the plurality of light signals.

In some embodiments, the selectively controlling the light signals includes controlling a pulse shape of the plurality of light signals.

In some embodiments, the selectively controlling the light signals includes controlling a minimum light intensity and a maximum light intensity of the plurality of light signals.

In some embodiments, the present invention provides a combination of electrical stimulation signals and optical stimulation signals, optionally delivered using electro-optical combination fibers and probes such as described in U.S. patent application Ser. No. 12/018,185 filed Jan. 22, 2008, titled "Hybrid Optical-Electrical Probes" (now U.S. Pat. No. 7,883,536 issued Feb. 8, 2011), and optionally including combination electro-optical stimulation signals such as described in U.S. patent application Ser. No. 12/573,848 filed Oct. 5, 2009, titled "Nerve Stimulator and Method using Simultaneous Electrical and Optical Signals". In some embodiments, the optical-stimulation light signals are selectively controlled to initiate or increase the rate of NAP triggering, while in other embodiments, the optical-stimulation light signals are selectively controlled to stop or decrease the rate of NAP triggering. In some embodiments, the selectively controlling the light signals includes controlling a DC background amount of light intensity of the plurality of light signals. In some embodiments, the stimulation signals include a plurality of signals substantially simultaneously emitted from a plurality of emitters that are all sub-threshold by themselves but which add to a threshold amount of light at the intersection of the light beams. In some embodiments, even at the intersection of the plurality of light beams, the amount of light is sub-threshold with regard to triggering a NAP when applied without a co-occurring electrical stimulation pulse (e.g., wherein the electrical pulse, if applied alone, is also sub-threshold with regard to triggering a NAP), but when the plurality of beams intersects at a nerve that is in the vicinity of the electrical signal, the combination of the plurality of sub-threshold light beams and the sub-threshold electrical signal is sufficient to trigger a NAP.

In some embodiments, the present invention provides a combination of electrical and optical stimulation. In some embodiments, the method further includes selectively controlling and applying to one or more tissues of the animal one or more electrical signals (i.e., hybrid electrical and optical stimulation of one or more tissues). In some embodiments, the selectively controlling and applying the electrical signal(s) includes controlling and applying a DC background amount of electrical signal. In some embodiments, the selectively controlling and applying the electrical signal(s) includes applying electrical pulses.

In some embodiments, the selectively controlling the light signals includes controlling a precharge amount of light intensity followed by a trigger amount of light intensity of the plurality of light signals.

In some embodiments, the selectively controlling the light signals includes controlling the light signals to delay at least some of the NAPs produced by the one or more nerves that would otherwise occur without the plurality of light signals.

In some embodiments, the selectively controlling the light signals includes controlling the light signals to increase a frequency of the NAPs produced by the one or more nerves that would otherwise occur without the plurality of light signals.

In some embodiments, the selectively controlling the light signals includes controlling the light signals to decrease a frequency of the NAPs produced by the one or more nerves that would otherwise occur without the plurality of light signals.

In some embodiments, the obtaining the plurality of light signals includes implanting a self-contained battery-powered laser-light-generation device.

In some embodiments, the plurality of light signals includes implanting self-contained infrared (IR) laser device.

In some embodiments, the delivering the plurality of light signals to one or more nerves of the PNS and/or the CNS includes using one or more optical fibers to guide the light signals.

In some embodiments, the delivering the plurality of light signals to one or more nerves of the PNS and/or the CNS includes positioning a delivery end of one or more fibers against a vestibular organ and using the one or more optical fibers to guide the light signals from a laser source to the vestibular organ.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

In some embodiments, electrical stimulation delivered via nerves connected to muscles is sensed. In some embodiments, the result of the muscular movement is sensed.

In some embodiments of the invention, monitoring muscular stimulation includes monitoring eye movements.

In some embodiments, electrical stimulation delivered via nerves connected to eye muscles is sensed. In some embodiments, the eye movement is sensed to indirectly sense eye muscle stimulation.

In some embodiments, the present invention provides an apparatus that includes one or more laser light sources configured to generate a plurality of light signals; and a transmission medium configured to transmit the plurality of light signals from the one or more laser light sources to one or more nerves of the PNS and/or the CNS of a living animal; a controller to selectively control the plurality of light signals from each of the one or more infrared-laser light sources such that the light signals provide controlled optical stimulation to the one or more nerves in order to control nerve action potentials (NAPs) produced by the one or more nerves.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the control of the light signals provided by the controller includes selective control of a pulse width of the plurality of light signals.

In some embodiments, the control of the light signals provided by the controller includes selective control of a duty cycle of the plurality of light signals.

In some embodiments, the control of the light signals provided by the controller includes selective control of an on-time and an off-time of the plurality of light signals.

In some embodiments, the control of the light signals provided by the controller includes selective control of a wavelength of the plurality of light signals.

In some embodiments, the control of the light signals provided by the controller includes selective control of a pulse repetition rate of the plurality of light signals.

In some embodiments, the control of the light signals provided by the controller includes selective control of a pulse shape of the plurality of light signals.

In some embodiments, the control of the light signals provided by the controller includes selective control of a minimum light intensity and a maximum light intensity of the plurality of light signals.

In some embodiments, the control of the light signals provided by the controller includes selective control of a DC background amount of light intensity of the plurality of light signals.

In some embodiments, the control of the light signals provided by the controller includes selective control of a pre-charge amount of light intensity followed by a trigger amount of light intensity amount of light intensity of the plurality of light signals.

In some embodiments, the control of the light signals provided by the controller includes selective control of the plurality of light signals to delay at least some of the NAPs produced by the one or more nerves that would otherwise occur.

In some embodiments, the control of the light signals provided by the controller includes selective control of the plurality of light signals to increase a frequency of the NAPs produced by the one or more nerves that would otherwise occur.

In some embodiments, the control of the light signals provided by the controller includes selective control of the plurality of light signals to decrease a frequency of the NAPs produced by the one or more nerves that would otherwise occur.

In some embodiments, the apparatus includes an implanted a self-contained battery-powered laser light-generation device.

In some embodiments, the obtaining the plurality of light signals includes implanting self-contained infrared (IR) laser device.

In some embodiments, the a transmission medium configured to transmit light signals from the one or more laser light sources to one or more nerves of the PNS and/or the CNS of a living animal includes one or more optical fibers configured to guide the light signals.

In some embodiments, the one or more laser light sources include a first light source and a second light source, wherein the control of the light signals provided by the controller includes selective control of the first light source to send a first series of pulses during a first period of time and selective control of the second light source to send a second series of pulses during the first period of time, and wherein the first series of pulses differs from the second series of pulses in repetition rate.

In some embodiments, the present invention provides an apparatus further including at least one sensor configured to sense one or more conditions that affect balance, and wherein the control of the light signals provided by the controller includes selective control of the light signals to provide a sense-of-balance nerve stimulation at least partly based on a signal from the at least one sensor.

In some embodiments, the at least one sensor includes a motion sensor.

In some embodiments, the at least one sensor includes an orientation sensor.

In some embodiments, the at least one sensor includes a muscular stimulation monitor.

In some embodiments, electrical stimulation carried via efferent nerves to muscles is sensed. In some embodiments, the result of the muscular movement is sensed.

In some embodiments, the muscular stimulation monitor includes a sensor that monitors eye movements.

In some embodiments, the present invention provides an apparatus that includes means for obtaining a plurality of light signals from one or more laser light sources; means for delivering the plurality of light signals to one or more nerve pathways of the PNS and/or the CNS of a living animal; and means for selectively controlling the plurality of light signals to optically stimulate the one or more nerves in order to control nerve action potentials (NAPs) or compound nerve-action potentials (CNAPs) produced in the one or more nerve pathways.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the means for selectively controlling the light signals includes means for controlling a pulse width of the plurality of light signals.

In some embodiments, the means for selectively controlling the light signals includes means for controlling a duty cycle of the plurality of light signals.

In some embodiments, the means for selectively controlling the light signals includes means for controlling an on-time and an off-time of the plurality of light signals.

In some embodiments, the means for selectively controlling the light signals includes means for controlling a wavelength of the plurality of light signals.

In some embodiments, the means for selectively controlling the light signals includes means for controlling a pulse repetition rate of the plurality of light signals.

In some embodiments, the means for selectively controlling the light signals includes means for controlling a pulse shape of the plurality of light signals.

In some embodiments, the means for selectively controlling the light signals includes means for controlling a minimum light intensity and a maximum light intensity of the plurality of light signals.

In some embodiments, the means for selectively controlling the light signals includes means for controlling a DC background amount of light intensity of the plurality of light signals.

In some embodiments, the means for selectively controlling the light signals includes means for controlling a precharge amount of light intensity followed by a trigger amount of light intensity of the plurality of light signals.

In some embodiments, the means for selectively controlling the light signals includes means for controlling the light signals to delay at least some of the NAPs produced by the one or more nerves that would otherwise occur without the plurality of light signals.

In some embodiments, the means for selectively controlling the light signals includes means for controlling the light signals to increase a frequency of the NAPs produced by the one or more nerves that would otherwise occur without the plurality of light signals.

In some embodiments, the means for selectively controlling the light signals includes means for controlling the light signals to decrease a frequency of the NAPs produced by the one or more nerves that would otherwise occur without the plurality of light signals.

In some embodiments, the means for obtaining the plurality of light signals includes implanting a self-contained battery-powered laser-light-generation device.

In some embodiments, the obtaining the plurality of light signals includes implanting self-contained infrared (IR) laser device.

In some embodiments, the means for delivering the plurality of light signals to one or more nerves of the PNS and/or the CNS includes using one or more optical fibers to guide the light signals.

In some embodiments, the one or more laser light sources include a first light source and a second light source, wherein the means for selectively controlling the plurality of light signals includes means for controlling the first light source to send a first series of pulses during a first period of time and means for controlling the second light source to send a second series of pulses during the first period of time, and wherein the first series of pulses differs from the second series of pulses in repetition rate.

In some embodiments, the means for sensing the one or more conditions that affect balance includes means for monitoring muscular stimulation.

In some embodiments, electrical stimulation delivered via nerves connected to muscles is sensed. In some embodiments, the result of the muscular movement is sensed.

In some embodiments, the means for monitoring muscular stimulation includes means for monitoring eye movements.

In some embodiments, electrical stimulation delivered via nerves connected to eye muscles is sensed. In some embodiments, the eye movement is sensed to indirectly sense eye muscle stimulation.

In some embodiments, electrical stimulation to eye muscles is sensed. In some embodiments, the eye movement is sensed to indirectly sense eye muscle stimulation.

In some embodiments, the present invention provides a method that includes obtaining light from an optical source; and transmitting the light to respective nerves the PNS and/or the CNS of an animal. The animal can either be a human or be some other animal.

In some embodiments, the transmitting includes transmitting different wavelengths of the light to stimulate respective nerves the PNS and/or the CNS.

In some embodiments, various parameters are adjusted and/or controlled, such as the pulse repetition rate or pattern, the pulse width, the pulse intensity, the wavelength(s), the amount of background constant (DC) optical level, and/or selected multiple simultaneous wavelengths. Multiple wavelengths are provided, in some embodiments, by using a plurality of lasers having different wavelengths. In some embodiments, a plurality of fibers is used to deliver the stimulation light to a plurality of stimulation sites.

In some embodiments, the present invention includes triggers and sensors that generate signals that are input to software of the present invention, wherein the software analyzes the signals and based on the analysis, generates control signals that control the parameters, such as frequency and intensity of light output (e.g., laser pulses) for each of one or more channels that communicate with the vestibular nucleus. For example, some embodiments use sensors such as described in U.S. Pat. No. 6,546,291 issued to Merfeld et al. on Apr. 8, 2003, which was described above and which is incorporated herein by reference. For example, some embodiments include sensors for detecting characteristics of the patient's head, eyes, posture and the like.

Some embodiments use one or more implanted VCSEL arrays to directly stimulate the desired nerves, while in other embodiments, one or more implanted VCSELs are optically coupled using one or more optical fibers leading to the stimulation sites.

In other embodiments, one or more VCSEL arrays are located external to the patient's body and use transcutaneous coupling to one or more implanted fiber arrays. In some embodiments, the implanted fiber arrays provide one or more feedback loops (e.g., a fiber having both of its ends facing outwards from the body) in order to assist coupling alignment. In some embodiments, permanent magnets are used on the implanted fiber arrays and external VCSEL stimulator to maintain coupling and assist in coupling alignment. In some embodiments, the implanted fiber arrays have a bulbous head on each fiber to collect and direct laser light into the fiber core.

Some embodiments provide programmable and/or reprogrammable control. In some embodiments, the controller is implanted in the body, and in some other embodiments, the controller is located external to the body and coupled to an implanted fiber array using transcutaneous coupling (e.g., some embodiments use a VCSEL array to provide light from the stimulator.

In some embodiments, electrical signals of the nerves are sensed and used to provide feedback to the controller, in order to better control the laser stimulation signal.

In some embodiments, the obtaining light includes implanting a self-contained infrared laser device.

In some embodiments, the obtaining light includes implanting a self-contained battery-powered device.

In other embodiments, the present invention provides an apparatus that includes an optical source; and a transmission medium configured to transmit light from the optical source to respective nerves of the PNS and/or the CNS of an animal.

In some embodiments, the transmission medium includes a plurality of optical fibers, and the optical source couples different amounts of the light through the plurality of optical fibers to stimulate different respective nerves of each of the PNS and/or the CNS.

In some embodiments, the optical source couples different wavelengths of the light to stimulate different respective nerves of each of the PNS and/or the CNS.

In some embodiments, the optical source includes a self-contained implantable infrared laser device.

In some embodiments, the optical source includes a self-contained battery-powered device.

In other embodiments, the present invention provides an apparatus that includes means for obtaining light from an optical source; and means for transmitting the light to respective nerves of the PNS and/or the CNS.

In some embodiments of the apparatus, the means for transmitting includes means for transmitting different amounts of the light through optical fibers to stimulate respective nerves of the PNS and/or the CNS. In some embodiments, the means for transmitting includes means for transmitting different wavelengths of the light to stimulate respective nerves of the PNS and/or the CNS. In some embodiments, the means for obtaining light includes a self-contained infrared laser implantable device. In some embodiments, the means for obtaining light includes a self-contained battery-powered implantable device.

Some Relevant Publications are the Following:

Shannon R V, Otto S R.; Psychophysical measures from electrical stimulation of the human cochlear nucleus, Hear. Res., 1990 Aug. 1; 47(1-2):159-68.

Otto S R, House W E, Brickman D E, Heidelberger W E, Nelson R A.; *Auditory brain stem implant: effect of tumor size and preoperative hearing level on function*, Ann. Otol. Rhinol. Laryngeal., 1990 October; 99(10 Pt 1):789-90.

Liu X, McPhee G, Seldon H L, Clark G M.; Histological and physiological effects of the central auditory prosthesis: surface versus penetrating electrodes, Hear, Res. 1997 December; 114(1-2):264-74.

Lenarz T, Lim HH, Reuter G, Patrick J F, Lenarz M.; The auditory midbrain implant: a new auditory prosthesis for neural deafness-concept and device description, Otol. Neurotol. 2006 September; 27(6):838-43. Review.

Samii A, Lenarz M, Majdani O, Lim HH, Samii M, Lenarz T.; Auditory midbrain implant: a combined approach for vestibular schwannoma surgery and device implantation. Otol. Neurotol. 2007 January; 28(1):31-8.

Some Advantages of the Invention Over Former Methods

In some embodiments, an advantage of optical stimulation of the nerves of the PNS and/or the CNS is the greater selectivity of neuronal activation using radiant energy compared with electrical stimulation wherein only neurons in the path of the laser light are activated. In some embodiments, the present invention provides optical-electrode hybrid designs that are able to use many more channels than electrically based systems, where channel crosstalk becomes a problem when using more electrodes spaced closely together. This has implications for all nerves of the PNS and the CNS. In some embodiments, the greater precision provided by using optical stimulation of the nerve and/or nerve bundle allows for more precise selective activation of particular neurons and minimizes the nonspecific stimulation of surrounding neurons.

A group from Vanderbilt University has described infrared laser stimulation in rat-brain slices (not in vivo) in a conference-proceedings publication, but this was not a peer-reviewed publication: Cayce, J M; Kao, CC; Mahadevan, G; Malphurus, J D; Konrad, P E; Jansen, E D; and Mahadevan-Jansen, A. *Optical stimulation of rat thalamocortical brain slices*. SPIE Proceedings January 2008, San Jose, Calif.

In some embodiments, the present invention provides a method for stimulating neurons of the PNS and/or the CNS of a patient to provide sensations for the patient. This method includes generating a plurality of light signals that, when applied to a neuron of a person, can stimulate a nerve action potential in the neuron; delivering the light signals to one or a plurality of neurons of the brainstem or midbrain of the patient; and selectively controlling the plurality of light signals to optically stimulate the one or more neurons in order to control nerve action potentials (NAPs) produced by the plurality of neurons.

Some embodiments of the method further include receiving image data; and processing the received image data to obtain vision information, wherein the delivering of light signals comprises delivering the light pulses to a vision portion of the brainstem or midbrain of the patient.

In some embodiments of the method, the delivering of light signals further includes delivering infrared light from a laser.

In some embodiments of the method, the delivering of light signals further includes delivering infrared light from a vertical-cavity surface-emitting laser (VCSEL).

In some embodiments of the method, the delivering of light signals further includes delivering the light signals to peripheral projections of the neurons.

In some embodiments of the method, the delivering of light signals further includes delivering the light signals to central portions of the neurons.

In some embodiments of the method, the delivering of the light signals further includes obtaining a plurality of light signals from one or more laser light sources and delivering the obtained light signals to discrete portions of excitable tissues, said signals being interpretable by the patient's brain as sensory responses.

In some embodiments of the method, the delivering of the light signals further includes selectively controlling the light signals to optically stimulate the one or more neurons in order to control nerve action potentials (NAPs) produced by the one or more neurons. In some embodiments of the method, the selectively controlling the light signals further includes controlling a pulse width of the plurality of light signals. In some embodiments of the method, the selectively controlling the light signals further includes controlling a pulse repetition rate of the plurality of light signals. In some embodiments of the method, the selectively controlling the light signals further includes controlling a pulse shape of the plurality of light signals. In some embodiments of the method, the selectively controlling the light signals further includes controlling a DC background amount of light intensity of the plurality of light signals. In some embodiments of the method, the selectively controlling the light signals further includes controlling a precharge amount of light intensity followed by a trigger amount of light intensity of the plurality of light signals. In some embodiments of the method, the selectively controlling the light signals further includes controlling the light signals to increase a frequency of the NAPs produced by the one or more neurons that would otherwise occur without the plurality of light signals.

In some embodiments of the method, the obtaining of the plurality of light signals further includes implanting a self-contained battery-powered laser-light-generation device.

In some embodiments of the method, the delivering of the light signals to the plurality of neurons of the brainstem or midbrain of the patient includes positioning a delivery end of a plurality of optical fibers in a probe end placed against the brainstem or midbrain of the patient and using the plurality of optical fibers to guide the light signals from a laser source to the brainstem or midbrain of the patient.

In some embodiments of the method, the generating of the light signals includes providing a first laser source and a second laser source, wherein the selectively controlling the plurality of light signals includes controlling the first laser source to send a first series of pulses during a first period of time and controlling the second laser source to send a second series of pulses during the first period of time, and wherein the first series of pulses differs from the second series of pulses in repetition rate. In some embodiments of the method, the sensing of the one or more conditions that affect balance includes monitoring eye movements.

In some embodiments, the present invention provides an apparatus that includes one or more light sources that are configured to generate a plurality of light signals; a transmission medium configured to transmit the plurality of light signals from the one or more light sources to a plurality of neurons of a nerve in the PNS and/or the CNS of a living animal to provide sensations for the living animal; and a controller operatively coupled to the one or more light sources to selectively control the plurality of light signals from each of the one or more light sources such that the light signals provide controlled optical stimulation to the plurality of neurons in order to control nerve action potentials (NAPs) produced by the plurality of neurons.

In some embodiments of the apparatus, control of the light signals provided by the controller includes selective control of a duty cycle of the plurality of light signals.

In some embodiments of the apparatus, the control of the light signals provided by the controller includes selective control of a wavelength of the plurality of light signals.

In some embodiments of the apparatus, the transmission medium includes a plurality of data channels (i.e., input and/or output channels (called "I/Os")). In some embodiments, the transmission medium includes a plurality of optical fibers, each having a conductive material (e.g., a metal film) applied to a surface of the optical fiber, wherein the conductive material is in turn covered with an insulator (e.g., a polymer coating, and/or a silicon oxide and/or silicon nitride insulator layer), and optionally one or more additional conductive layers further coated by additional insulator layers to provide a coaxially shielded electrical conductor that is formed directly on the optical fiber, and wherein the optical fiber is used to deliver the optical stimulation pulses and the one or more electrical conductors are used to transmit electrical stimulation or pre-conditioning electrical energy to the tissue being stimulated. In some embodiments, the electrical conductors are also used to carry electrical signals sensed from the neurons of the patient (e.g., NAP signals in the nerve pathways are detected electrically using the conductors formed on the optical fibers). In some embodiments, each of a plurality of the optical fibers have a metallic coating that has an insulator formed over the metallic coating, and a bundle of such fibers deliver a plurality of different optical signals (e.g., the optical-stimulation pulses are individually controlled) in parallel and a plurality of different stimulation electrical signals (e.g., the electrical-stimulation or -preconditioning pulses are individually controlled) in parallel such that different areas of nerve of the PNS and/or the CNS of the patient are stimulated in different manners In some embodiments of the apparatus, the transmission medium includes a plurality of optical fibers each of which carries a different signal. In some such embodiments, the plurality of optical fibers each have one or more electrical conductors formed thereon, wherein each of a plurality of the electrical conductors carry a different signal.

In some embodiments of the apparatus, the transmission medium includes an optical fiber. In some embodiments of the apparatus, the transmission medium includes a lens. In some embodiments of the apparatus, the transmission medium delivers the light signals from the one or more light sources without using an optical fiber or a lens. In some embodiments of the apparatus, the transmission medium includes other light-transmitting materials such as quartz, fused silica, silicon, InP, GaP, and the like, made in light-guiding shapes such as an array of, or other configuration having one or more, individual rods, cones, pyramids, and the like, the end(s) of which shapes are, in various embodiments, shaped with domes, lenses, gratings, chamfers, curved waveguides, and the like, for light-shaping and pointing purposes.

Some embodiments of the apparatus further includes a sensor (e.g., light, pressure, temperature, sound, or the like) having a signal output operatively coupled to a wireless transmitter that is configured to transmit information based on the sensor signal to the controller.

In some embodiments of the apparatus, the sensor further includes a processor that is configured to receive a stimulus response signal and based on the signal to generate information used by the controller to generate stimulation pulses configured to be interpretable by the living animal's brain in order to encode understanding of the stimulus response signal.

In some embodiments of the apparatus, the one or more light sources further include one or more lasers. In some embodiments of the apparatus, the one or more light sources further include at least one tunable laser. In some embodiments of the apparatus, the one or more lasers output an infrared signal having a wavelength between about one micron and about five microns, inclusive. In some embodiments of the apparatus, the one or more lasers output an infrared signal having a wavelength in a range of between about one micron and about two microns (the range inclusive). In some embodiments of the apparatus, the one or more lasers output an infrared signal having a wavelength between about 1.8 microns and about 1.9 microns.

In some other embodiments of the apparatus, the one or more lasers output an infrared signal having a wavelength between about 0.7 microns and about 0.8 microns, inclusive. In some embodiments of the apparatus, the one or more lasers output an ultraviolet signal having a wavelength between about 0.1 microns and about 0.4 microns, inclusive. In some embodiments of the apparatus, the one or more lasers output a visible signal having a wavelength between about 0.4 microns and about 0.7 microns, inclusive. In some embodiments of the apparatus, the one or more lasers output an infrared signal having a wavelength between about 0.8 microns and about 0.9 microns, inclusive. In some embodiments of the apparatus, the one or more lasers output an infrared signal having a wavelength between about 0.9 microns and about 1.0 microns, inclusive. In some embodiments of the apparatus, the one or more lasers output an infrared signal having a wavelength between about 1.0 microns and about 1.1 microns, inclusive. In some embodiments of the apparatus, the one or more lasers output an infrared signal having a wavelength between about 1.1 microns and about 1.2 microns, inclusive. In some embodiments of the apparatus, the one or more lasers output an infrared signal having a wavelength between about 1.2 microns and about 1.3 microns, inclusive. In some embodiments of the apparatus, the one or more lasers output an infrared signal having a wavelength between about 1.3 microns and about 1.4 microns, inclusive. In some embodiments of the apparatus, the one or more lasers output an infrared signal having a wavelength between about 1.4 microns and about 1.5 microns, inclusive. In some embodiments of the apparatus, the one or more lasers output an infrared signal having a wavelength between about 1.5 microns and about 1.6 microns, inclusive. In some embodiments of the apparatus, the one or more lasers output an infrared signal having a wavelength between about 1.6 microns and about 1.7 microns, inclusive. In some embodiments of the apparatus, the one or more lasers output an infrared signal having a wavelength between about 1.7 microns and about 1.8 microns, inclusive. In some embodiments of the apparatus, the one or more lasers output an infrared signal having a wavelength between about 1.9 microns and about 2.0 microns, inclusive. In some embodiments of the apparatus, the one or more lasers output an infrared signal having a wavelength between about 2.0 microns and about 2.1 microns, inclusive. In some embodiments of the apparatus, the one or more lasers output an infrared signal having a wavelength between about 2.1 microns and about 2.3 microns, inclusive. In some embodiments of the apparatus, the one or more lasers output an infrared signal having a wavelength between about 2.3 microns and about 2.5 microns, inclusive. In some embodiments of the apparatus, the one or more lasers output an infrared signal having a wavelength between about 2.5 microns and about 3 microns, inclusive. In some embodiments of the apparatus, the one or more lasers output an infrared signal having a wavelength between about 3 microns and about 5 microns, inclusive. In some embodiments of the apparatus, the one or more lasers output an infrared signal having a wavelength between about 5 microns and about 10 microns, inclusive. In some embodiments, the lasers output an optical signal having two or more wavelengths in one or more of the above-listed ranges. In some embodiments, a first subset (e.g., blue light) of two or more wavelengths is selectively transmitted to activate neurons, while a second subset of wavelengths (e.g., yellow light) is selectively transmitted to deactivate neurons (such as described in the above-cited paper by Bernstein, Jacob G., et al. titled *"Prosthetic systems for therapeutic optical activation and silencing of genetically-targeted neurons"* that describes that two naturally-occurring light-activated proteins channelrhodopsin-2 (ChR2) and halorhodopsin (Halo/NpHR) can, when genetically expressed in neurons, enable them to be safely, precisely, and reversibly activated and silenced by pulses of blue and yellow light, respectively, wherein in some embodiments, the two (or more) light-activated proteins are virally or transgenically delivered into the desired neurons to transform such neurons into what we call optogenetically active neurons).

In some embodiments of the apparatus, the one or more lasers output an infrared signal having a wavelength of about 1540 nanometers (1.54 microns). In some embodiments of the apparatus, the one or more lasers output an infrared signal having a wavelength of about 1800 nanometers. In some embodiments of the apparatus, the one or more lasers output an infrared signal having a wavelength of about 1849 nanometers. In some embodiments of the apparatus, the one or more lasers output an infrared signal having a wavelength of 1849 nanometers.

In some embodiments, the present invention further includes applying a precharge amount of stimulation electrical current to the neuronal tissue of the patient that is to be stimulated (e.g., to a plurality of nerve pathways the brainstem or midbrain of the patient), which is then followed by a trigger amount of pulsed light intensity of the plurality of light signals.

In some embodiments, the nerve stimulation includes an electrical current of about 0.1 mA to about 10 mA, plus an optical energy of about 0.01 J/cm$^2$ to about 1 J/cm$^2$. In some embodiments, the stimulation includes an electrical current of about 0.01 mA to about 0.02 mA between closely spaced electrodes (in some embodiments, the closely spaced electrodes include a metallization layer on each of two optical fibers that are both in one fiber-optic bundle; while in other embodiments, the closely spaced electrodes include separated portions of a metallization layer on a single optical fiber (e.g., wherein the metallization has been etched into a plurality of separate longitudinal conductors, and, in some embodiments, wherein the etching is helical around the optical fiber such that a twisted pair of conductors (or a plurality of such pairs) is formed, while in other embodiments, coaxial metallization layers are formed using an insulating layer to separate each pair of conduction layers). A current is sent through the separate conductors on the optical fiber and thus through the tissue that is adjacent to the light-emitting end of the optical-fiber waveguide such that the electrical field and the optical radiation are self aligned with one another. In some embodiments, the stimulation includes an electrical current of about 0.02 mA to about 0.05 mA between closely spaced electrodes. In some embodiments, the stimulation includes an electrical current of about 0.025 mA to about 0.035 mA between closely spaced electrodes. In some embodiments, the stimulation includes an electrical current of about 0.035 mA to about 0.05 mA between closely spaced electrodes. In some embodiments, the stimulation includes an electrical current of about 0.025 mA between closely spaced electrodes. In some embodiments, the stimulation includes an electrical current of about 0.035 mA between closely spaced electrodes. In some embodiments, the stimulation includes an electrical current of about 0.05 mA between closely spaced electrodes. In some embodiments, the stimulation includes an electrical current of about 0.1 mA between closely spaced electrodes. In some embodiments, the stimulation includes an electrical current of about 0.05 mA to about 0.1 mA between closely spaced electrodes. In some embodiments, the stimulation includes an electrical current of about 0.1 mA to about 0.2 mA between closely spaced electrodes. In some embodiments, the stimulation includes an electrical current of about 0.2 mA to about 0.5 mA between closely spaced electrodes. In some embodiments, the stimulation includes an electrical current of about 0.5 mA to about 1 mA between closely spaced electrodes. In some embodiments, the stimulation includes an electrical current of about 1 mA to about 2 mA between closely spaced electrodes. In some embodiments, the stimulation includes an electrical current of about 2 mA to about 5 mA between closely spaced electrodes. In some embodiments, the stimulation includes an electrical current of about 5 mA to about 10 mA between closely spaced electrodes.

In some embodiments, the pulse repetition rate of the optical signal is about 1 to 2 pulses per second. In some embodiments, the pulse repetition rate of the optical signal is about 2 to 5 pulses per second. In some embodiments, the pulse repetition rate of the optical signal is about 5 to 10 pulses per second. In some embodiments, the pulse repetition rate of the optical signal is about 10 to 20 pulses per second. In some embodiments, the pulse repetition rate of the optical signal is about 20 to 50 pulses per second. In some embodiments, the pulse repetition rate of the optical signal is about 50 to 100 pulses per second. In some embodiments, the pulse repetition rate of the optical signal is about 100 to 200 pulses per second. In some embodiments, the pulse repetition rate of the optical signal is about 200 to 500 pulses per second. In some embodiments, the pulse repetition rate of the optical signal is about 500 to 1000 pulses per second. In some embodiments, the pulse repetition rate of the optical signal is about 1000 to 2000 pulses per second. In some embodiments, the pulse repetition rate of the optical signal is more than about 2000 pulses per second.

In some embodiments of the apparatus, the one or more lasers output an infrared signal having a radiant exposure of no more than 4 J/cm$^2$ per nerve-action-potential response generated. In some embodiments of the apparatus, the one or more lasers output an infrared signal having a radiant exposure of no more than 3 J/cm$^2$ per nerve-action-potential response generated. In some embodiments of the apparatus, the one or more lasers output an infrared signal having a radiant exposure of no more than 2 J/cm$^2$ per nerve-action-potential response generated.

In some embodiments of the apparatus, the one or more lasers output an infrared signal having a radiant exposure of between about 5 J/cm$^2$ and about 6 J/cm$^2$ per nerve-action-potential response generated. In some embodiments of the apparatus, the one or more lasers output an infrared signal having a radiant exposure of between about 4 J/cm$^2$ and about 4 J/cm$^2$ per nerve-action-potential response generated. In some embodiments of the apparatus, the one or more lasers output an infrared signal having a radiant exposure of between about 3 J/cm$^2$ and about 4 J/cm$^2$ per nerve-action-potential response generated. In some embodiments of the apparatus, the one or more lasers output an infrared signal having a radiant exposure of between about 3 J/cm$^2$ and about 3.5 J/cm$^2$ per nerve-action-potential response generated. In some embodiments of the apparatus, the one or more lasers output an infrared signal having a radiant exposure of between about 2.5 J/cm$^2$ and about 3 J/cm$^2$ per nerve-action-potential response generated. In some embodiments of the apparatus, the one or more lasers output an infrared signal having a radiant exposure of between about 2 J/cm$^2$ and about 2.5 J/cm$^2$ per nerve-action-potential response generated. In some embodiments of the apparatus, the one or more lasers output an infrared signal having a radiant exposure of between about 1.5 J/cm$^2$ and about 2 J/cm$^2$ per nerve-action-potential response generated. In some embodiments of the apparatus, the one or more lasers output an infrared signal having a radiant exposure of between about 1 J/cm$^2$ and about 1.5 J/cm$^2$ per nerve-action-potential response generated. In some embodiments of the apparatus, the one or more lasers output an infrared signal having a radiant exposure of between about 0.5 J/cm$^2$ and about 1 J/cm$^2$ per nerve-action-potential response generated. In some embodiments of the apparatus, the one or more lasers output an infrared signal having a radiant exposure of between about 0.2 J/cm$^2$ and about 0.5 J/cm$^2$ per nerve-action-potential response generated. In some embodiments of the apparatus, the one or more lasers output an infrared signal having a radiant exposure of between about 0.1 J/cm$^2$ and about 0.2 J/cm$^2$ per nerve-action-potential response generated.

In some embodiments, the one or more lasers output an infrared signal having and energy of less than about 2 mJ per pulse.

In some embodiments, the one or more lasers output an infrared signal having a pulse width of between about ten microseconds (10 µs) and about five milliseconds (5 ms).

In some embodiments, the one or more lasers output an infrared signal having a pulse width of between about 1 µs and about 10 µs. In some embodiments, the one or more lasers output an infrared signal having a pulse width of between about 10 µs and about 20 µs. In some embodiments, the one or more lasers output an infrared signal having a pulse width of between about 20 µs and about 50 µs. In some embodiments, the one or more lasers output an infrared signal having a pulse width of between about 20 µs and about 40 µs. In some embodiments, the one or more lasers output an infrared signal having a pulse width of between about 40 µs and about 80 µs. In some embodiments, the one or more lasers output an infrared signal having a pulse width of between about 80 µs and about 160 µs. In some embodiments, the one or more lasers output an infrared signal having a pulse width of between about 50 µs and about 100 µs. In some embodiments, the one or more lasers output an infrared signal having a pulse width of between about 100 µs and about 200 µs. In some embodiments, the one or more lasers output an infrared signal having a pulse width of between about 200 µs and about 500 µs. In some embodiments, the one or more lasers output an infrared signal having a pulse width of between about 200 µs and about 400 µs. In some embodiments, the one or more lasers output an infrared signal having a pulse width of between about 400 µs and about 800 µs. In some embodiments, the one or more lasers output an infrared signal having a pulse width of between about 800 µs and about 1600 µs. In some embodiments, the one or more lasers output an infrared signal having a pulse width of between about 500 µs and about 1000 µs. In some embodiments, the one or more lasers output an infrared signal having a pulse width of between about 1 millisecond (ms) and about 2 ms. In some embodiments, the one or more lasers output an infrared signal having a pulse width of between about 2 ms and about 5 ms. In some embodiments, the one or more lasers output an infrared signal having a pulse width of between about 2 ms and about 4 ms. In some embodiments, the one or more lasers output an infrared signal having a pulse width of between about 4 ms and about 8 ms. In some embodiments, the one or more lasers output an infrared signal having a pulse width of between about 8 ms and about 16 ms. In some embodiments, the one or more lasers output an infrared signal having a pulse width of between about 5 ms and about 10 ms.

In some embodiments, the present invention delivers a pulse of electrical current to the same site as light pulses. In some embodiments, the electrical pulses are below the threshold for neural excitation and the electric field spreads to a larger area than required for the region of interest (the area of specific nerve pathways to be stimulated). The light pulse from the apparatus of the present invention is delivered to match the exact volume of tissue that is to be stimulated: In some embodiments, the stimulation includes an electrical current of about 0.1 mA to about 10 mA, plus an optical energy of about 0.01 J/cm$^2$ to about 1 J/cm$^2$. Other parameters are determined by empirical experimentation, wherein the pulse repetition rate is generally about 10 to 1000 pulses per second.

In some such embodiments, the present invention provides a method that includes applying a combination of both an electrical stimulation signal and an optical stimulation signal to trigger a nerve action potential (NAP) in vivo in the brainstem or midbrain of an animal. In some embodiments of this method, the optical stimulation signal is of a nature such that if applied alone the optical signal has a low probability to trigger a NAP, the probability being no more than 25%. In some embodiments of this method, the electrical stimulation signal is of a nature such that if applied alone the electrical signal has a low probability to trigger a NAP, the probability being no more than 25%. In some embodiments of this method, the electrical stimulation signal is of a nature such that if applied alone the electrical signal has a low probability to trigger a NAP, the probability being no more than 25%. Some embodiments of this method further include also selectively applying a visible-indication light signal that indicates a location that the optical stimulation signal is to be applied.

Some embodiments of this method further include using a hybrid probe having an optical fiber inserted an electrically conductive cannula; applying the optical-stimulation signal through the optical fiber; and applying the electrical-stimulation signal through the cannula. Some embodiments further include delivering a fluid through the cannula to enhance the electrical interface for the electrical-stimulation signal and/or to enhance the optical interface for the optical-stimulation signal and/or to deliver one or more drugs to the stimulation site. Some embodiments further include withdrawing a fluid through the cannula to diagnose a condition. Some embodiments of this method further include using a second probe to obtain an electrical signal representative of the triggered NAP. Some embodiments of this method further include the hybrid probe further includes an electrode that is electrically separate from the cannula, and the method further includes using the electrode to obtain an electrical response signal representative of the triggered NAP. Some embodiments of this method further include using the cannula to obtain an electrical response signal representative of the triggered NAP.

In some embodiments of this method, a signal representative of the electrical stimulation signal is subtracted from a signal obtained using the cannula to obtain the electrical response signal representative of the triggered NAP.

Some embodiments of this method further include using a hybrid probe having an optical fiber that has a metallization layer applied to the optical fiber; applying the optical-stimulation signal through the optical fiber; and applying the electrical-stimulation signal through the metallization layer. Some embodiments of this method further include using a second probe to obtain an electrical response signal representative of the triggered NAP. In some embodiments of this method, the hybrid probe further includes an electrode that is electrically separate from the metallization layer, and the method further includes using the electrode to obtain an electrical response signal representative of the triggered NAP. Some embodiments of this method further include using the metallization layer to obtain an electrical response signal representative of the triggered NAP.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the brainstem or midbrain of an animal.

In some embodiments of this apparatus, the optical stimulation signal is of a nature such that if applied alone the optical stimulation signal has a low probability to trigger a NAP, the probability being no more than 25%. In some embodiments of this apparatus, the electrical stimulation signal is of a nature such that if applied alone the electrical stimulation signal has a low probability to trigger a NAP, the probability being no more than 25%. In some embodiments of this apparatus, the electrical stimulation signal is of a nature such that if applied alone the electrical stimulation signal has a low probability to trigger a NAP, the probability being no more than 25%. In some embodiments of this apparatus, the optical stimulation signal is infrared, and the apparatus further includes a visible-indication-light-signal source configured to project visible light to indicate a location that the optical stimulation signal is to be applied. Some embodiments of this apparatus further include a hybrid probe having an optical fiber inserted an electrically conductive cannula, wherein the optical-stimulation signal is applied through the optical fiber and the electrical-stimulation signal is applied through the cannula. Some embodiments further include a second probe configured to obtain an electrical signal representative of the triggered NAP. In some embodiments, the hybrid probe further includes an electrode that is electrically separate from the cannula, wherein the electrode is configured to obtain an electrical signal representative of the triggered NAP. In some embodiments, the cannula is used to obtain an electrical signal representative of the triggered NAP. In some such embodiments, the apparatus is configured to subtract a signal representative of the electrical stimulation signal from a signal obtained using the cannula to obtain the electrical signal representative of the triggered NAP.

Some embodiments further include a hybrid probe having an optical fiber that has a metallization layer applied to the optical fiber, wherein the optical-stimulation signal is applied through the optical fiber and the electrical-stimulation signal is applied through the metallization layer. Some embodiments further include a second probe configured to obtain an electrical signal representative of the triggered NAP. In some embodiments, the hybrid probe further includes an electrode that is electrically separate from the metallization layer, and is configured to obtain an electrical signal representative of the triggered NAP. In some embodiments, the apparatus is configured to use the metallization layer to obtain an electrical signal representative of the triggered NAP.

In some embodiments, the present invention provides a method that includes obtaining a signal (such as an audio signal, a video signal, a gravitational orientation, an acceleration signal, a rotation signal, a temperature signal, a pressure signal or the like), and based on the sensed signal applying a combination of both an electrical stimulation signal and an optical stimulation signal to trigger a nerve action potential (NAP) in vivo in the cerebral cortex of an animal.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the cerebral cortex of an animal.

In some embodiments, the present invention provides a method that includes receiving a signal, and based on the received signal applying a combination of both an electrical stimulation signal and an optical stimulation signal to trigger a nerve action potential (NAP) in vivo in the spinal cord of an animal.

In some embodiments, the present invention provides a method that includes emitting pulsed signal light having a wavelength and having a pulse duration from each of a plurality of lasers (for example, lasers such as vertical cavity surface-emitting lasers (VCSELs) or edge-emitting lasers) including a first laser and a second laser, wherein the lasers are in a device implanted in a patient; directing the signal light from the first laser onto a first tissue of the patient to stimulate a given physiological response in the first tissue but substantially not onto a second tissue; and directing the light from the second laser onto the second tissue of the patient to stimulate the second tissue but substantially not onto the first tissue. In some embodiments, the signal light has an wavelength between about 0.1 microns and about 0.2 microns, inclusive. In some embodiments, the signal light has an wavelength between about 0.2 microns and about 0.3 microns, inclusive. In some embodiments, the signal light has an wavelength between about 0.3 microns and about 0.4 microns, inclusive. In some embodiments, the signal light has a visible wavelength between about 0.4 microns and about 0.45 microns, inclusive. In some embodiments, the signal light has a visible wavelength between about 0.45 microns and about 0.5 microns, inclusive. In some embodiments, the signal light has a visible wavelength between about 0.5 microns and about 0.55 microns, inclusive. In some embodiments, the signal light has a visible wavelength between about 0.55 microns and about 0.6 microns, inclusive. In some embodiments, the signal light has a visible wavelength between about 0.6 microns and about 0.65 microns, inclusive. In some embodiments, the signal light has a visible wavelength between about 0.65 microns and about 0.7 microns, inclusive. In some embodiments, the signal light has a wavelength between about 0.7 microns and about 0.75 microns, inclusive. In some embodiments, the signal light has a wavelength between about 0.75 microns and about 0.8 microns, inclusive. In some embodiments, the signal light has a wavelength between about 0.8 microns and about 0.9 microns, inclusive. In some embodiments, the signal light has a wavelength between about 0.9 microns and about 1.0 microns, inclusive. In some embodiments, the signal light has a wavelength between about 1.0 microns and about 1.1 microns, inclusive. In some embodiments, the signal light has a wavelength between about 1.1 microns and about 1.2 microns, inclusive. In some embodiments, the signal light has a wavelength between about 1.2 microns and about 1.3 microns, inclusive. In some embodiments, the signal light has a wavelength between about 1.3 microns and about 1.4 microns, inclusive. In some embodiments, the signal light has a wavelength between about 1.4 microns and about 1.5 microns, inclusive. In some embodiments, the signal light has a wavelength between about 1.5 microns and about 1.6 microns, inclusive. In some embodiments, the signal light has a wavelength between about 1.6 microns and about 1.7 microns, inclusive. In some embodiments, the signal light has an infrared wavelength between about 1.7 microns and about 1.8 microns, inclusive. In some embodiments, the signal light has an infrared wavelength between about 1.8 microns and about 1.9 microns, inclusive. In some embodiments, the signal light has an infrared wavelength between about 1.9 microns and about 2 microns, inclusive. In some embodiments, the signal light has an infrared wavelength between about 2 microns and about 2.1 microns, inclusive. In some embodiments, the signal light has an infrared wavelength between about 2.1 microns and about 2.3 microns, inclusive. In some embodiments, the signal light has an infrared wavelength between about 2.3 microns and about 2.5 microns, inclusive. In some embodiments, the signal light has an infrared wavelength between about 2.5 microns and about 2.75 microns, inclusive. In some embodiments, the signal light has an infrared wavelength between about 2.75 microns and about 3 microns, inclusive. In some embodiments, the signal light has an infrared wavelength of at least about 3 microns. In some embodiments, the signal light has two or more wavelengths that are in one or more of the above ranges.

In some embodiments, the present invention provides an apparatus that includes an electrical-stimulation-signal source configured to selectively output an electrical-stimulation signal; an optical-stimulation-signal source configured to selectively output an optical-stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the spinal cord of an animal. In some embodiments, the electrical-stimulation signal and the optical-stimulation signal are each at a level that is substantially sub-threshold (i.e., almost all of the time (i.e., at least 90%) they will not trigger a NAP if either is applied alone, but when applied together (either simultaneously or sufficiently close to one another in time), the combination of electrical- and optical-stimulation signals is sufficient to trigger a NAP (i.e., almost all of the time (i.e., at least 90%) the combination will trigger a NAP). In some embodiments, the electrical-stimulation signal and the optical-stimulation signal are each at a level that is usually sub-threshold (i.e., most of the time (i.e., at least 50%) they will not trigger a NAP) if either is applied alone, but when applied together (either simultaneously or sufficiently close to one another in time), the combination of electrical- and optical-stimulation signals is usually sufficient to trigger a NAP (i.e., most of the time (i.e., at least 50%) the combination will trigger a NAP).

In some embodiments, the present invention delivers light pulses from vertical surface-emitting lasers (VCSELs). In some embodiments, electrical pulses are also delivered at below threshold for neural excitation and spread to larger area than required for the region of interest (the area to be stimulated). The light pulse is delivered to match the exact volume that is to be stimulated: In some embodiments, the electrical energy is about 0.1 mA to about 10 mA plus optical energy=0.01–1 $J/cm^2$; Other parameters are determined by empirical experimentation, wherein frequency is generally about 10 to 1000 pulses per second.

In some such embodiments, the present invention provides, in combination with others of the other embodiments described herein, one or more of the following: a method that includes emitting pulsed light having a wavelength in a range of 1.8 microns to 2 microns and having a pulse duration from each of a plurality of vertical cavity surface-emitting lasers (VCSELs) including a first VCSEL and a second VCSEL, directing the light from the first VCSEL onto a first tissue to stimulate the first tissue but substantially not onto a second tissue, and directing the light from the second VCSEL onto the second tissue to stimulate the second tissue but substantially not onto the first tissue; such a method but further including emitting pulsed light having a wavelength in a range of 650 nm to 850 nm and having a pulse duration from each of a plurality of vertical cavity surface-emitting lasers (VCSELs) including a third VCSEL and a fourth VCSEL, directing the light from the third VCSEL onto the first tissue and illuminating the first tissue but substantially not illuminating the second tissue, detecting a reflected light from the first tissue and determining a first physiological activity of the first tissue, directing the light from the fourth VCSEL onto the second tissue and illuminating the second tissue but substantially not illuminating the first tissue, and detecting a reflected light from the second tissue and determining a second physiological activity of the second tissue. In some such embodiments, the first VCSEL and the second VCSEL are located on a single semiconductor substrate. In some such embodiments, the third VCSEL and the fourth VCSEL are located on a single semiconductor substrate. In some such embodiments, the first VCSEL, the second VCSEL, the third VCSEL and the fourth VCSEL are located on a single semiconductor substrate. Some embodiments further include integrating a first microlens with the first VCSEL and focusing the pulsed light from the first VCSEL onto the first tissue, integrating a second microlens with the second VCSEL and focusing the pulsed light from the second VCSEL onto the second tissue, integrating a third microlens with the third VCSEL and focusing the pulsed light from the third VCSEL onto the first tissue, and integrating a fourth microlens with the fourth VCSEL and focusing the pulsed light from the fourth VCSEL onto the second tissue. Some embodiments further include providing a fiber optic bundle including a plurality of optical fibers, integrating a first optical fiber with the first VCSEL and directing the pulsed light from the first VCSEL onto the first tissue, integrating a second optical fiber with the second VCSEL and directing the pulsed light from the second VCSEL onto the second tissue, integrating a third optical fiber with the third VCSEL and directing the pulsed light from the third VCSEL onto the first tissue, and integrating a fourth optical fiber with the fourth VCSEL and directing the pulsed light from the fourth VCSEL onto the second tissue. In some embodiments, each optical fiber in the plurality of optical fibers includes a lens. In some embodiments, the first VCSEL and the third VCSEL are integrated into a first flex-cuff ring and the second VCSEL and the third VCSEL are integrated into a second flex-cuff ring. In some embodiments, the first VCSEL, the second VCSEL, the third VCSEL and the fourth VCSEL are mounted in a biocompatible housing having an optical feed through.

In some such embodiments, the present invention provides an apparatus that includes a plurality of vertical cavity surface-emitting lasers (VCSELs) including a first VCSEL and a second VCSEL; a control circuit configured to control generation of pulsed light from the first and second VCSELs; and a light-delivery system configured to direct the light from the first VCSEL onto a first tissue but substantially not onto a second tissue in order to stimulate the first tissue; wherein the light-delivery system is further configured to direct the light from the second VCSEL onto the second tissue but substantially not onto the first tissue in order to stimulate the second tissue. In some embodiments, the apparatus further includes a plurality of vertical cavity surface-emitting lasers (VCSELs) including a third VCSEL and a fourth VCSEL. The control circuit is further configured to control generation of pulsed light from the third and fourth VCSELs; the light delivery system is further configured to direct the light from the third VCSEL onto a first tissue but substantially not onto a second tissue in order to illuminate the first tissue; the light delivery system is further configured to direct the light from the fourth VCSEL onto the second tissue but substantially not onto the first tissue in order to illuminate the second tissue; a plurality of detectors including a first detector and a second detector; the first detector is configured to detect reflected light from the first tissue to determine a first physiological activity in the first tissue; and the second detector is configured to detect reflected light from the second tissue to determine a second physiological activity in the second tissue. In some embodiments, the first VCSEL and the second VCSEL are provided on a single semiconductor substrate. In some embodiments, the third VCSEL and the fourth VCSEL are provided on a single semiconductor substrate. In some embodiments, the first VCSEL, the second VCSEL, the third VCSEL and the fourth VCSEL are provided on a single semiconductor substrate. In some embodiments, an array of microlenses, integrated on surface of chip is a light-directing structure that directs light from individual VCSELs in a plurality of parallel or different-angled directions. In some embodiments, a plurality of other light-guiding and/or focusing elements (e.g., diffractive surfaces, graded-index fiber sections (called GRIN lenses), or other suitable light shaping and/or direction guiding devices) are fabricated against the VCSEL array. Some embodiments include a first microlens integrated with the first VCSEL to focus the pulsed light from the first VCSEL onto the first tissue; a second microlens integrated with the second VCSEL to focus the pulsed light from the second VCSEL onto the second tissue; a third microlens integrated with the third VCSEL to focus the pulsed light from the third VCSEL onto the first tissue; and a fourth microlens integrated with the fourth VCSEL to focus the pulsed light from the fourth VCSEL onto the second tissue. Some embodiments further include a fiber optic bundle including a plurality of optical fibers, each optical fiber having a first end and a second end; a first optical fiber operatively coupled at the first end of the first optical fiber to the first VCSEL to direct the pulsed light from the first VCSEL through the first optical fiber and the second end of the first optical fiber onto the first tissue; a second optical fiber operatively coupled at the first end of the second optical fiber to the second VCSEL to direct the pulsed light from the second VCSEL through the second optical fiber and the second end of the second optical fiber onto the second tissue; a third optical fiber operatively coupled at the first end of the third optical fiber to the third VCSEL to direct the pulsed light from the third VCSEL through the third optical fiber and the second end of the third optical fiber onto the first tissue; and a fourth optical fiber operatively coupled at the first end of the fourth optical fiber to the fourth VCSEL to direct the pulsed light from the fourth VCSEL through the fourth optical fiber and the second end of the fourth optical fiber onto the second tissue. In some embodiments, each optical fiber in the plurality of optical fibers includes a lens. In some embodiments, the first VCSEL and the third VCSEL are integrated into a first flex-cuff ring and the second VCSEL and the third VCSEL are integrated into a second flex-cuff ring. In some embodiments, the first VCSEL, the second VCSEL, the third VCSEL and the fourth VCSEL are mounted in a biocompatible housing having an optical feed through.

In some of the embodiments described herein as using VCSEL arrays (e.g., VCSEL arrays using electrically pumped semiconductor diode structures) instead uses one or more arrays of other light-emitting devices (such as light-emitting diodes (LEDs), superluminescent devices, optical-fiber lasers, optically-pumped semiconductor lasers (whether or not the laser cavities of such lasers are vertical cavity and surface emitting devices)).

In some embodiments, the present invention provides a method that includes selectively emitting a plurality of light signals, each having a wavelength and each having a pulse duration, from each of a plurality of vertical cavity surface-emitting lasers (VCSELs) including a first VCSEL and a second VCSEL; directing the light from the first VCSEL onto a first tissue of the patient, wherein the light from the first VCSEL onto a first tissue of the patient is insufficient alone to stimulate a nerve action potential (NAP) in the first tissue; and directing the light from the second VCSEL onto the first tissue of the patient, wherein the light from the second VCSEL onto a first tissue of the patient is insufficient alone to stimulate a nerve action potential (NAP) in the first tissue, but wherein the light from the first VCSEL and the light from the second VCSEL intersecting onto the first tissue of the patient is sufficient to stimulate a NAP in the first tissue. In some embodiments, the wavelength directed from the first laser is different than the wavelength directed from the second laser. In some embodiments, the first and second laser signals are emitted from a pointy structure that is within the tissue, i.e., the optical-emitting end of the device penetrates the nerve bundle. In some such embodiments, the optical-emitting pointy structure penetrates the peripheral nerve bundle radially from the side and at an angle that is substantially perpendicular to the longitudinal axis of the peripheral nerve bundle, or that is at an acute angle to the longitudinal axis, or that penetrates (for example, in the case of a severed nerve bundle end) from an end of the nerve bundle.

In some embodiments of the method, the plurality of VCSELs are arranged around a periphery of the first tissue, and the emitting pulsed light includes emitting collimated light inward toward the tissue from the first VCSEL and inward toward the tissue from the second VCSEL such that the collimated light from the first and second VCSELs intersect at non-parallel angles.

In some embodiments of the method, the first and second lasers are on different cuffs surrounding a peripheral nerve bundle such that the first and second lasers stimulate a single nerve within the peripheral nerve bundle at two longitudinal locations along the nerve.

In some embodiments of the method, the directing the light from the first VCSEL and second VCSEL onto the first tissue includes focusing the pulsed light from the first VCSEL to stimulate the NAP in a first nerve fiber that is deeper in the first tissue than a second nerve fiber that is closer to a surface layer in the first tissue adjacent the first VCSEL without stimulating a NAP in the second nerve fiber.

In some embodiments of the method, the directing of the light from at least one of the first VCSEL and second VCSEL onto the first tissue includes using a waveguide with a reflective end that emits light from a sidewall of the waveguide.

In some embodiments of the method, the emitting pulsed light from the first VCSEL and the second VCSEL includes emitting light of different wavelengths, a first wavelength of the first laser is different than a second wavelength of the second laser, and the directing of the light from the first VCSEL and second VCSEL onto the first tissue includes using waveguides and diffraction gratings.

In some embodiments of the method, the selectively emitting the light signals includes varying the pulse duration of at least one of the plurality of light signals, and wherein the selectively emitting the light signals includes emitting pulsed light substantially simultaneously from the first VCSEL and the second VCSEL.

In some embodiments of the method, the selectively emitting the light signals includes varying a pulse-repetition rate of the plurality of light signals.

In some embodiments of the method, the selectively emitting the light signals includes selectively varying a pulse temporal intensity shape of the plurality of light signals.

In some embodiments of the method, the selectively emitting the light signals includes controlling a DC background amount of light intensity of the plurality of light signals.

In some embodiments of the method, the selectively emitting the light signals includes controlling a precharge amount of light intensity followed by a trigger amount of light intensity of the plurality of light signals.

In some embodiments of the method, further includes applying a precharge current of electrical energy that is followed by a trigger amount of pulsed light intensity of the plurality of light signals.

In some embodiments of the method, the wavelength(s) of light from the first VCSEL and the wavelength of light from second VCSEL are in a range of about 1.8 microns to 2 microns. In some embodiments, the wavelength is visible to a human eye (e.g., having one or more wavelengths between 400 nm and 700 nm). In other embodiments, other wavelengths such as ultraviolet (shorter than about 400 nm) or near infrared (e.g., between about 700 nm and about 1800 nm) are used. In other embodiments, far infrared (e.g., longer than about 2000 nm (out to about 10,000 nm)) are used.

Some embodiments of the method further include a computerized method of determining which of a first plurality of combinations of nerve-stimulation signals cause a reaction in the patient and storing that information for future reference and stimulation, wherein each of the plurality of combinations of nerve-stimulation signals include a plurality of VCSEL-light signals, wherein the computerized method of determining includes: iteratively applying a plurality of different combinations of nerve-stimulation signals to the patient and acquiring data as to one or more responses that were caused by each combination of stimulation signals; providing specifications of a plurality of desired responses to each of a plurality of conditions; correlating and mapping the specifications of a plurality of desired responses with the data as to the responses that were caused by each combination of stimulation signals, and storing a resulting mapping in a computer-readable memory; determining that one of the plurality of conditions has occurred; and based on the stored mapping and the determination that one of the plurality of conditions has occurred, driving the corresponding combination of stimulation signals to evoke the desired response to the condition in the patient.

In some embodiments of the method, the nerve-stimulation signals include an electrical-sensitization signal.

In some embodiments of the method, the plurality of VCSEL-light signals include a plurality of different optical power levels and/or a plurality of different optical wavelengths In some embodiments of the method, the determining that one of the plurality of conditions has occurred includes: sensing a first patient-physiology parameter, generating a first patient-physiology signal based on the first patient-physiology parameter, and controlling the driving of the stimulation signals based on the first patient-physiology signal.

In some embodiments of the method, the method further includes detecting an amount of light output onto the first tissue, and using feedback based on the detected amount of light to control the intensity or duration of the selectively emitting of the plurality of light signals. In some such embodiments, the detecting of the output optical signal is performed by obtaining some of the light directly from the emitting device, while in other embodiments, the detecting is of light reflected or diffused from the tissue being stimulated. In some embodiments, one or more temperature-measuring devices are used to control the feedback that controls the light output.

In some embodiments of the method, the determining that one of the plurality of conditions has occurred includes: sensing a first environmental parameter, generating a first environmental signal based on the first environmental parameter, and controlling the driving of the stimulation signals based on the first environmental signal. In some embodiments, the environmental parameters include one or more of the group consisting of heat, pressure, sound, proprioception, patient feedback, or any other suitable parameter.

Some embodiments of the method further include selectively emitting light signals having a wavelength in a range of 1.8 microns to 2 microns and having a pulse duration from a third VCSEL; directing the light from the third VCSEL onto the first tissue; and detecting a reflected light from the first tissue and determining a first physiological activity of the first tissue.

In some embodiments, the present invention provides an apparatus that includes a plurality of vertical cavity surface-emitting lasers (VCSELs) including a first VCSEL and a second VCSEL; a control circuit configured to control generation of pulsed nerve-stimulation light from the first and second VCSELs; and a light-delivery system configured to direct the light from the first VCSEL onto a first tissue of the patient, wherein the light from the first VCSEL onto a first tissue of the patient is insufficient alone to stimulate a nerve action potential (NAP) in the first tissue, and to direct the light from the second VCSEL onto the first tissue of the patient, wherein the light from the second VCSEL onto a first tissue of the patient is insufficient alone to stimulate a nerve action potential (NAP) in the first tissue, but wherein the light from the first VCSEL and the light from the second VCSEL intersecting onto the first tissue of the patient deliver a trigger amount of pulsed light sufficient to stimulate a NAP in the first tissue.

Some embodiments of the apparatus further include a control circuit configured to control generation of a pre-charge (or sensitization amount) current of electrical energy that is delivered during a period of time correlated to (before and/or during) the delivery of the trigger amount of pulsed light intensity of the plurality of light signals.

Some embodiments of the apparatus further include a computer-readable storage medium, wherein the storage medium includes instructions stored thereon for causing a suitably programmed information processor to execute a method comprising: determining which of a first plurality of combinations of nerve-stimulation signals cause a reaction in the patient and storing that information for future reference and stimulation, wherein each of the plurality of combinations of nerve-stimulation signals include a plurality of VCSEL-light signals, wherein the computerized method of determining includes: iteratively applying a plurality of different combinations of nerve-stimulation signals to the patient and acquiring data as to one or more responses that were caused by each combination of stimulation signals; providing specifications of a plurality of desired responses to each of a plurality of conditions; correlating and mapping the specifications of a plurality of desired responses with the data as to the responses that were caused by each combination of stimulation signals, and storing a resulting mapping in a computer-readable memory; determining that one of the plurality of conditions has occurred; and based on the stored mapping and the determination that one of the plurality of conditions has occurred, driving the corresponding combination of stimulation signals to evoke the desired response to the condition in the patient.

In some embodiments, the present invention provides a method that includes selectively emitting light signals having a wavelength and having a pulse duration from each of a plurality of solid-state light sources (such as semiconductor lasers (including VCSELs, edge-emitting lasers and quantum-dot lasers, multiple-quantum-well (MQW) lasers and the like), fiber lasers having semiconductor pump lasers and/or monolithic-glass-substrate waveguide lasers having semiconductor pump lasers, LEDs, superluminescent emitters and the like) including a first solid-state light source and a second solid-state light source; directing the light from the first solid-state light source onto a first tissue of the patient, wherein the light from the first solid-state light source onto a first tissue of the patient is insufficient alone to stimulate a nerve action potential (NAP) in the first tissue; and directing the light from the second solid-state light source onto the first tissue of the patient, wherein the light from the second solid-state light source onto a first tissue of the patient is insufficient alone to stimulate a nerve action potential (NAP) in the first tissue, but wherein the light from the first solid-state light source and the light from the second solid-state light source intersecting onto the first tissue of the patient is sufficient to stimulate a NAP in the first tissue.

In some embodiments, the present invention provides a method that includes selectively emitting light signals having a wavelength and having a pulse duration from each of a plurality of lasers including a first laser and a second laser; directing the light from the first laser onto a first tissue of the patient, wherein the light from the first laser onto a first tissue of the patient is insufficient alone to stimulate a nerve action potential (NAP) in the first tissue; and directing the light from the second laser onto the first tissue of the patient, wherein the light from the second laser onto a first tissue of the patient is insufficient alone to stimulate a nerve action potential (NAP) in the first tissue, but wherein the light from the first laser and the light from the second laser intersecting onto the first tissue of the patient is sufficient to stimulate a NAP in the first tissue.

In some embodiments of the method, the plurality of lasers are arranged around a periphery of the first tissue, and the emitting pulsed light includes emitting collimated light inward toward the tissue from the first laser and inward toward the tissue from the second laser such that the collimated light from the first and second lasers intersect at non-parallel angles.

In some embodiments of the method, the directing the light from the first laser and second laser onto the first tissue includes focusing the pulsed light from the first laser to stimulate the NAP in a first nerve fiber that is deeper in the first tissue than a second nerve fiber that is closer to a surface layer in the first tissue adjacent the first laser without stimulating a NAP in the second nerve fiber.

In some embodiments of the method, the directing of the light from at least one of the first laser and second laser onto the first tissue includes using a waveguide with a reflective end that emits light from a sidewall of the waveguide.

In some embodiments of the method, the emitting pulsed light from the first laser and the second laser includes emitting light of different wavelengths, and the directing the light from the first laser and second laser onto the first tissue includes using waveguides and diffraction gratings.

In some embodiments of the method, the selectively emitting the light signals includes varying the pulse duration of at least one of the plurality of light signals, and wherein the selectively emitting the light signals includes emitting pulsed light substantially simultaneously from the first laser and the second laser.

In some embodiments of the method, the selectively emitting the light signals includes varying a pulse-repetition rate of the plurality of light signals.

In some embodiments of the method, the selectively emitting the light signals includes selectively varying a pulse shape of the plurality of light signals.

In some embodiments of the method, the selectively emitting the light signals includes controlling a non-pulsed background amount of light intensity of the plurality of light signals.

In some embodiments of the method, the selectively emitting the light signals includes controlling a precharge amount of light intensity followed by a trigger amount of light intensity of the plurality of light signals.

In some embodiments of the method, further includes applying a precharge current of electrical energy that is followed by a trigger amount of pulsed light intensity of the plurality of light signals.

In some embodiments of the method, the wavelength of light from the first laser and the wavelength of light from second laser are in a range of about 1.8 microns to 2 microns.

Some embodiments of the method further include a computerized method of determining which of a first plurality of combinations of nerve-stimulation signals cause a reaction in the patient and storing that information for future reference and stimulation, wherein each of the plurality of combinations of nerve-stimulation signals include a plurality of laser-light signals, wherein the computerized method of determining includes: iteratively applying a plurality of different combinations of nerve-stimulation signals to the patient and acquiring data as to one or more responses that were caused by each combination of stimulation signals; providing specifications of a plurality of desired responses to each of a plurality of conditions; correlating and mapping the specifications of a plurality of desired responses with the data as to the responses that were caused by each combination of stimulation signals, and storing a resulting mapping in a computer-readable memory; determining that one of the plurality of conditions has occurred; and based on the stored mapping and the determination that one of the plurality of conditions has occurred, driving the corresponding combination of stimulation signals to evoke the desired response to the condition in the patient.

In some embodiments of the method, the nerve-stimulation signals include an electrical-sensitization signal.

In some embodiments of the method, the plurality of VCSEL-light signals include a plurality of different optical power levels and/or a plurality of different optical wavelengths In some embodiments of the method, the determining that one of the plurality of conditions has occurred includes: sensing a first patient-physiology parameter, generating a first patient-physiology signal based on the first patient-physiology parameter, and controlling the driving of the stimulation signals based on the first patient-physiology signal.

In some embodiments of the method, the determining that one of the plurality of conditions has occurred includes: sensing a first environmental parameter, generating a first environmental signal based on the first environmental parameter, and controlling the driving of the stimulation signals based on the first environmental signal.

Some embodiments of the method further includes selectively emitting light signals having a wavelength in a range of 1.8 microns to 2 microns and having a pulse duration from a third laser; directing the light from the third laser onto the first tissue; and detecting a reflected light from the first tissue and determining a first physiological activity of the first tissue.

Some embodiments of the method the first laser is a first vertical cavity surface-emitting laser (VCSEL) and the second laser is a second VCSEL.

Some embodiments of the method the plurality of lasers includes a plurality of vertical cavity surface-emitting lasers (VCSELs) formed on a single substrate, and the first laser is a first VCSEL formed on the substrate and the second laser is a second VCSEL formed on the substrate.

In some embodiments, the present invention provides an apparatus that includes a plurality of lasers including a first laser and a second laser; a control circuit configured to control generation of pulsed nerve-stimulation light from the first and second lasers; and a light-delivery system configured to direct the light from the first laser onto a first tissue of the patient, wherein the light from the first laser onto a first tissue of the patient is insufficient alone to stimulate a nerve action potential (NAP) in the first tissue, and to direct the light from the second laser onto the first tissue of the patient, wherein the light from the second laser onto a first tissue of the patient is insufficient alone to stimulate a nerve action potential (NAP) in the first tissue, but wherein the light from the first laser and the light from the second laser intersecting onto the first tissue of the patient deliver a trigger amount of pulsed light is sufficient to stimulate a NAP in the first tissue.

Some embodiments of the apparatus further include a control circuit configured to control generation of a pre-charge (or sensitization amount) current of electrical energy that is delivered during a period of time correlated to (before and/or during) the delivery of the trigger amount of pulsed light intensity of the plurality of light signals.

Some embodiments of the apparatus further include a computer-readable storage medium, wherein the storage medium includes instructions stored thereon for causing a suitably programmed information processor to execute a method comprising: determining which of a first plurality of combinations of nerve-stimulation signals cause a reaction in the patient and storing that information for future reference and stimulation, wherein each of the plurality of combinations of nerve-stimulation signals include a plurality of laser-light signals, wherein the computerized method of determining includes: iteratively applying a plurality of different combinations of nerve-stimulation signals to the patient and acquiring data as to one or more responses that were caused by each combination of stimulation signals; providing specifications of a plurality of desired responses to each of a plurality of conditions; correlating and mapping the specifications of a plurality of desired responses with the data as to the responses that were caused by each combination of stimulation signals, and storing a resulting mapping in a computer-readable memory; determining that one of the plurality of conditions has occurred; and based on the stored mapping and the determination that one of the plurality of conditions has occurred, driving the corresponding combination of stimulation signals to evoke the desired response to the condition in the patient.

Some embodiments of the apparatus, the first laser is a first vertical cavity surface-emitting laser (VCSEL) and the second laser is a second VCSEL.

Some embodiments of the apparatus, the plurality of lasers includes a plurality of vertical cavity surface-emitting lasers (VCSELs) formed on a single substrate, and the first laser is a first VCSEL formed on the substrate and the second laser is a second VCSEL formed on the substrate.

In some embodiments, the present invention provides an apparatus that includes a plurality of vertical cavity surface-emitting lasers (VCSELs) including a first VCSEL and a second VCSEL; means for directing the light from the first VCSEL onto a first tissue of the patient, wherein the light from the first VCSEL onto a first tissue of the patient is insufficient alone to stimulate a nerve action potential (NAP) in the first tissue; and means for directing the light from the second VCSEL onto the first tissue of the patient, wherein the light from the second VCSEL onto a first tissue of the patient is insufficient alone to stimulate a nerve action potential (NAP) in the first tissue, but wherein the light from the first VCSEL and the light from the second VCSEL intersecting onto the first tissue of the patient is sufficient to stimulate a NAP in the first tissue.

Some embodiments further include a means for determining which of a first plurality of combinations of nerve-stimulation signals cause a reaction in the patient and storing that information for future reference and stimulation, wherein each of the plurality of combinations of nerve-stimulation signals include a plurality of VCSEL-light signals, wherein the means for determining includes: means for iteratively applying a plurality of different combinations of nerve-stimulation signals to the patient and acquiring data as to one or more responses that were caused by each combination of stimulation signals; means for providing specifications of a plurality of desired responses to each of a plurality of conditions; means for correlating and mapping the specifications of a plurality of desired responses with the data as to the responses that were caused by each combination of stimulation signals, and means for storing a resulting mapping in a computer-readable memory; means for determining that one of the plurality of conditions has occurred; and means for, based on the stored mapping and the determination that one of the plurality of conditions has occurred, driving the corresponding combination of stimulation signals to evoke the desired response to the condition in the patient.

In some embodiments, the present invention provides an apparatus that includes a plurality of vertical cavity surface-emitting lasers (VCSELs) including a first VCSEL and a second VCSEL; means for directing the light from the first VCSEL onto a first tissue of the patient, wherein the light from the first VCSEL onto a first tissue of the patient is insufficient alone to stimulate a nerve action potential (NAP) in the first tissue; and means for directing the light from the second VCSEL onto the first tissue of the patient, wherein the light from the second VCSEL onto a first tissue of the patient is insufficient alone to stimulate a nerve action potential (NAP) in the first tissue, but wherein the light from the first VCSEL and the light from the second VCSEL intersecting onto the first tissue of the patient is sufficient to stimulate a NAP in the first tissue.

In some embodiments of the apparatus, the apparatus further includes a means for determining which of a first plurality of combinations of nerve-stimulation signals cause a reaction in the patient and storing that information for future reference and stimulation, wherein each of the plurality of combinations of nerve-stimulation signals include a plurality of VCSEL-light signals, wherein the means for determining includes means for iteratively applying a plurality of different combinations of nerve-stimulation signals to the patient and acquiring data as to one or more responses that were caused by each combination of stimulation signals; means for providing specifications of a plurality of desired responses to each of a plurality of conditions; means for correlating and mapping the specifications of a plurality of desired responses with the data as to the responses that were caused by each combination of stimulation signals, and means for storing a resulting mapping in a computer-readable memory; means for determining that one of the plurality of conditions has occurred; and means for, based on the stored mapping and the determination that one of the plurality of conditions has occurred, driving the corresponding combination of stimulation signals to evoke the desired response to the condition in the patient.

In some embodiments, the present invention provides a method and/or apparatus for selectively recruiting a first volume of neural tissue with a first set of one or more stimulating channels and in close proximity but without overlap providing additional sources for stimulating distinct volumes of tissue, such that multi-channel laser stimulation arrays can provide coverage of large volumes of neural tissue without overlap. In some embodiments, one or more of the four geometries in FIG. 5 are used (realizing that this figure depicts only single stimulating elements and that many of these could be multiplexed into a larger system). In some embodiments of each, the invention further includes materials, geometries, laser parameters, hybrid optical-electrical as well as optical-only stimulation, overlapping optical stimulation from sources that if applied alone are insufficient to stimulate but when simultaneously applied are sufficient to trigger the desired nerve response, and/or any other suitable embodiments described throughout the present application.

The present invention also contemplates various combinations and subcombinations of the embodiments set forth in the above description.

As used herein, "substantially simultaneously" emitting pulsed light from a plurality of sources means emitting light pulses simultaneously, at least partially overlapped in time, or emitting light pulses close enough in time so as to cause a physiological response that is the same as if the light pulses were emitted simultaneously.

In some embodiments, the present invention provides an apparatus that includes a plurality of laser-light sources configured to generate a plurality of laser-light signals, wherein the plurality of laser-light sources includes a first laser-light source that emits light having a first wavelength and a second laser-light source that emits light having the first wavelength; one or more driver circuits that provide drive power required to operate the plurality of laser-light sources; a control circuit operatively coupled to the driver circuits and configured to control emission of pulsed light from the first and second laser-light sources; and a laser-light-delivery system having at least one pointed end and configured to deliver the plurality of laser-light signals independently to each of a plurality of nerves within a peripheral nerve bundle of an animal in order to independently optically stimulate each of the plurality of nerves in the peripheral nerve bundle to trigger action potentials in the plurality of nerves, wherein at least the pointed end of the laser-light-delivery system is configured to be transversely implanted into the peripheral nerve bundle.

In some embodiments of the apparatus, "transversely implanted" includes insertion at either ninety degrees relative to the longitudinal axis of the peripheral nerve bundle or one or more acute angles relative to the longitudinal axis of the peripheral nerve bundle that does not parallel the longitudinal axis of the peripheral nerve bundle. In some embodiments, the laser-light-delivery system includes two or more delivery systems inserted into the peripheral nerve bundle at a plurality of radial (compass) directions. In some embodiments, the plurality of laser-light sources includes a plurality of vertical-cavity-surface-emitting lasers (VCSELs) located near the pointed end including a first VCSEL and a second VCSEL, and the apparatus further includes a mechanical support system that supports the plurality of VCSELs, wherein the plurality of VCSELs are arranged on the mechanical support such that when the laser-light-delivery system is transversely implanted into the peripheral nerve bundle the first VCSEL is located at a first transverse depth within the peripheral nerve bundle and the second VCSEL is located at a second transverse depth within the peripheral nerve bundle. In some such embodiments, the mechanical support system is a single mechanical support and the VCSELs are arranged as a one-dimensional array along the single mechanical support. In some embodiments, the mechanical support system is a single mechanical support and the VCSELs are arranged as a two-dimensional array along the single mechanical support. In some embodiments, the mechanical support system includes a plurality of parallel mechanical supports and the VCSELs are arranged as a two-dimensional array such that some of the plurality of VCSELs are located on each of the plurality of parallel mechanical supports. In some embodiments, the mechanical support system includes a first mechanical support and a second mechanical support, wherein a first set of the plurality of VCSELs are supported by the first mechanical support and are configured to deliver the plurality of laser-light signals in a first direction into the plurality of nerves from within the peripheral nerve bundle, wherein a second set of the plurality of VCSELs are supported by the second mechanical support and are configured to deliver the plurality of laser-light signals in a second radial direction into the plurality of nerves from within the peripheral nerve bundle, and wherein the second direction is different than the first radial direction. In some embodiments, the mechanical support system includes a first mechanical support, and wherein VCSELs supported by the first mechanical support are configured to deliver the plurality of laser-light signals in each of a plurality of radial directions into the peripheral nerve bundle.

In some embodiments of the apparatus, the plurality of laser-light sources includes a plurality of vertical-cavity-surface-emitting lasers (VCSELs), and the apparatus further includes a first mechanical support system configured to support the plurality of VCSELs, wherein the first mechanical support system further includes a plurality of short optical fibers arranged in a plurality of needle-like bundles, each optical fiber extending from one of the plurality of VCSELs, wherein the plurality of needle-like bundles are each configured to be transversely inserted into the peripheral nerve bundle. In some embodiments, the plurality of laser-light sources includes a plurality of vertical-cavity-surface-emitting lasers (VCSELs), the apparatus further comprising a first mechanical support system configured to support the plurality of VCSELs, wherein the first mechanical support system further includes a plurality of short waveguides arranged in a plurality of needle-like bundles, each waveguide extending from one of the plurality of VCSELs, wherein the plurality of needle-like bundles are each configured to be transversely inserted into the peripheral nerve bundle. In some such embodiments, the plurality of short waveguides includes a plurality of short optical fibers. In some such embodiments, the plurality of short waveguides is made from a material that includes silicon, a polymer, or any other suitable material. In some such embodiments, the plurality of short waveguides is coated with an optical coating, or any other suitable coating. In some such embodiments, the plurality of short waveguides has a triangular-shaped pointed end or any other suitable geometry.

Some embodiments further include an electrical cable configured to provide an electrical connection between the one or more driver circuits and the control circuit, wherein the control circuit is located at a distal end of the electrical cable.

In some embodiments, the present invention provides an apparatus that includes a plurality of laser-light sources configured to generate a plurality of laser-light signals, wherein the plurality of laser-light sources includes a first laser-light source that emits light having a first wavelength and a second laser-light source that emits light having the first wavelength; one or more driver circuits that provide drive power required to operate the plurality of laser-light sources; a control circuit operatively coupled to the driver circuits and configured to control emission of pulsed light from the first and second laser-light sources; and a laser-light-delivery system having at least one pointed end and configured to deliver the plurality of laser-light signals independently to each of a plurality of nerves within a peripheral nerve bundle of an animal in order to independently optically stimulate each of the plurality of nerves in the peripheral nerve bundle to trigger action potentials in the plurality of nerves, wherein at least the pointed end of the laser-light-delivery system is configured to be longitudinally implanted into a severed peripheral nerve bundle.

In some embodiments, the present invention provides a method that includes transversely implanting a laser-light-delivery system into a peripheral nerve bundle of an animal, the laser-light-delivery system having a first pointed end inserted into the peripheral nerve bundle; generating a plurality of pulsed laser-light signals including a first pulsed laser-light signal having a first wavelength and a second pulsed laser-light signal having the first wavelength; and independently delivering the plurality of pulsed laser-light signals through the laser-light-delivery system to each of a plurality of nerves within the peripheral nerve bundle, and, based on the plurality of pulsed laser-light signals, independently optically triggering an action potential in each of the plurality of nerves in the peripheral nerve bundle.

In some embodiments of the method, the plurality of laser-light sources includes a plurality of vertical-cavity-surface-emitting lasers (VCSELs) located near the first pointed end of the laser-light-delivery system including a first VCSEL and a second VCSEL, and the method further includes mechanically supporting the plurality of VCSELs on the laser-light-delivery system such that the first VCSEL is located at a first transverse depth within the peripheral nerve bundle and the second VCSEL is located at a second transverse depth within the peripheral nerve bundle. In some such embodiments, the mechanically supporting of the plurality of VCSELs includes arranging the plurality of VCSELs as a one-dimensional array along a single mechanical support. In some embodiments, the mechanically supporting of the plurality of VCSELs includes arranging the plurality of VCSELs as a two-dimensional array along a single mechanical support. In some embodiments, the mechanically supporting of the plurality of VCSELs includes arranging the plurality of VCSELs as a two-dimensional array such that some of the plurality of VCSELs are located on each of a plurality of parallel mechanical supports.

Some embodiments of the method further include providing a plurality of mechanical supports including a first mechanical support and a second mechanical support, wherein the first pointed end is on the first mechanical support and a second pointed end is on the second mechanical support, wherein the independently delivering of the plurality of laser-light signals includes delivering laser-light signals from a first subset of the plurality of VCSELs located on the first mechanical support in a first direction and delivering the plurality of laser-light signals from a second subset of the plurality of VCSELs located on the second mechanical support in a second direction.

In some embodiments of the method, the plurality of laser-light sources includes a plurality of vertical-cavity-surface-emitting lasers (VCSELs) including a first VCSEL and a second VCSEL, and the method further includes providing a plurality of short optical fibers configured to be inserted into the peripheral nerve bundle, wherein the plurality of short optical fibers are arranged in a plurality of needle-like bundles, wherein the first pointed end is an end of one of the plurality of needle-like bundles; and extending an optical fiber of the plurality of optical fibers from each one of the plurality of VCSELs.

In some embodiments of the method, the laser-light-delivery system includes a plurality of vertical-cavity-surface-emitting lasers (VCSELs), and the independently delivering of the plurality of laser-light signals includes emitting laser-light signals from the laser-light-delivery system in a plurality of non-parallel directions.

Some embodiments of the method further include delivering an electrical current from a plurality of driver circuits at one end of an electrical cable to a plurality of lasers at another distal end of the electrical cable; and using the electrical current to generate the plurality of laser-light signals from the plurality of lasers.

In some embodiments, the present invention provides an apparatus that includes a plurality of laser-light sources configured to generate a plurality of laser-light signals, wherein the plurality of laser-light sources includes a first laser-light source that emits light having a first wavelength and a second laser-light source that emits light having the first wavelength; and, as described herein, means for independently delivering the plurality of laser-light signals to each of a plurality of nerves within a peripheral nerve bundle of an animal in order to independently optically stimulate each of the plurality of nerves in the peripheral nerve bundle to trigger action potentials in the plurality of nerves, wherein the means for delivering includes a first pointed end, and wherein the means for delivering is configured to be transversely implanted into the peripheral nerve bundle. In some embodiments of this apparatus, the plurality of laser-light sources includes a plurality of vertical-cavity-surface-emitting lasers (VCSELs), wherein the plurality of VCSELs includes a first VCSEL and a second VCSEL both located near the first pointed end of the means for delivering, and the apparatus further includes means for mechanically supporting the plurality of VCSELs such that the first VCSEL is located at a first transverse depth within the peripheral nerve bundle and the second VCSEL is located at a second transverse depth within the peripheral nerve bundle. In some embodiments of this apparatus, the means for mechanically supporting the plurality of VCSELs includes means for arranging the plurality of VCSELs as a one-dimensional array. In some embodiments of this apparatus, the means for mechanically supporting the plurality of VCSELs includes means for arranging the plurality of VCSELs as a two-dimensional array. In some embodiments of this apparatus, the plurality of laser-light sources includes a plurality of vertical-cavity-surface-emitting lasers (VCSELs) located near the first pointed end of the means for delivering, wherein the plurality VCSELs includes a first VCSEL and a second VCSEL, wherein the means for delivering includes means for delivering the plurality of laser-light signals of a first subset of the plurality of VCSELs in a first radial direction and means for delivering the plurality of laser-light signals from a second subset of the plurality of VCSELs in a second radial direction.

In some embodiments, the present invention provides an apparatus that includes a plurality of laser-light sources configured to generate a plurality of laser-light signals; and an optical-fiber bundle, wherein the optical-fiber bundle includes a plurality of optical fibers operatively coupled to the plurality of laser-light sources and configured to transmit the plurality of laser-light signals into a peripheral nerve bundle of an animal, non-invasively relative to the peripheral nerve bundle, in order to independently optically stimulate each of a plurality of nerves in the peripheral nerve bundle such that action potentials are independently triggered in the plurality of nerves. In some embodiments of this apparatus, the optical-fiber bundle is configured to emit the plurality of laser-light signals from a first end of the optical-fiber bundle located at an interface between the optical-fiber bundle and the peripheral nerve bundle. In some embodiments of this apparatus, each one of the plurality of optical fibers includes an emitting end configured to emit one of the plurality of laser-light signals, wherein the plurality of emitting ends are located at a plurality of different locations along a longitudinal length of the optical-fiber bundle. In some embodiments of this apparatus, each one of the plurality of optical fibers includes an inline fiber grating configured to emit its one of the plurality of laser-light signals, wherein each one of the plurality of inline fiber gratings is located at one of a plurality of different locations along a longitudinal length of the optical-fiber bundle.

In some embodiments, the present invention provides an apparatus that includes a plurality of vertical cavity surface-emitting lasers (VCSELs) including a first VCSEL that emits pulsed light having a first wavelength and a second VCSEL that emits pulsed light having the first wavelength; one or more driver circuits operatively coupled to the plurality of VCSELs and configured to provide drive power required to operate the plurality of VCSELs; a control circuit operatively coupled to the one or more driver circuits and configured to control emission of the pulsed light from the first and second VCSELs; and a cuff light-delivery system configured to wrap around neural tissue of an animal and to direct the pulsed light emitted from the first VCSEL to trigger action potentials in a first set of one or more nerves in the neural tissue but substantially not trigger action potentials in a second set of one or more other nerves in the neural tissue, wherein the cuff light-delivery system is further configured to direct the pulsed light emitted from the second VCSEL to trigger action potentials in the second set of one or more nerves in the neural tissue but substantially not trigger action potentials in the first set of one or more nerves.

In some embodiments, the cuff light-delivery system includes a first waveguide coupled to the first VCSEL and configured to transmit the pulsed light emitted from the first VCSEL to the first set of one or more nerves, and a second waveguide operatively coupled to the second VCSEL and configured to transmit the pulsed light emitted from the second VCSEL to the second set of one or more nerves. In some embodiments, the first waveguide is a graded-index (GRIN) fiber.

In some embodiments, the first wavelength is a wavelength visible to human eyes. In some embodiments, the first wavelength is an infrared wavelength.

In some embodiments of the apparatus, the control circuit is integrated in a single chip with the one or more driver circuits. In some embodiments, the apparatus further includes an electrical cable configured to provide an electrical connection between the one or more driver circuits and the control circuit, wherein the control circuit is located at a distal end of the electrical cable. In some such embodiments, the control circuit is configured to be partially implanted into the animal such that at least part of the control circuit resides external to the animal.

In some embodiments of the apparatus, the VCSELs are located on an inner surface of the cuff facing the neural tissue. In some embodiments, the cuff does not completely encircle a circumference of the neural tissue. In some embodiments, the cuff completely encircles a circumference of the neural tissue. In some embodiments, the plurality of VCSELs is implemented on a single semiconductor substrate. In some embodiments, the apparatus further includes a microlens integrated with each of the plurality of VCSELs to focus the light emitted from each VCSEL onto different portions of the neural tissue.

In some embodiments of the apparatus, the plurality of VCSELs further includes a third VCSEL that emits pulsed light having a second wavelength, and a fourth VCSEL that emits pulsed light having the second wavelength, wherein the control circuit is further configured to control emission of the pulsed light from the third and fourth VCSELs, wherein the cuff light-delivery system is further configured to direct the pulsed light from the third VCSEL to pass through the first set of one or more nerves to trigger action potentials in a third set of nerves but substantially not trigger action potentials in the first set of one or more nerves or the second set of one or more nerves, and wherein the cuff light-delivery system is further configured to direct the pulsed light from the fourth VCSEL to pass through the second set of one or more nerves to trigger action potentials in a fourth set of nerves but substantially not trigger action potentials in the second set of one or more nerves or the first set of one or more nerves. In some embodiments, the first wavelength is in a range of 1.8 microns to 2 microns, and wherein the second wavelength is in a range of 650 nanometers to 850 nanometers.

In some embodiments of the apparatus, the apparatus further includes a plurality of optical detectors including a first detector and a second detector, wherein the first detector is configured to detect reflected light from the first set of one or more nerves to determine a first physiological activity in the first set of one or more nerves, and wherein the second detector is configured to detect reflected light from the second set of one or more nerves to determine a second physiological activity in the second set of one or more nerves (e.g., using light to detect the triggered action potentials). In other embodiments, the apparatus further includes a plurality of electrical detectors including a first detector and a second detector, wherein the first detector is configured to detect electrical activity from the first set of one or more nerves to determine a first physiological activity in the first tissue, and wherein the second detector is configured to detect electrical activity from the second set of one or more nerves to determine a second physiological activity in the second set of one or more nerves (e.g., using electricity to detect the triggered action potentials). In some embodiments, the apparatus further includes a light dosage detector configured to detect an amount of light directed to the first and second set of one or more nerves in the neural tissue by the plurality of VCSELs.

In some embodiments, the present invention provides an apparatus that includes an array of light emitters located on a semiconductor substrate including a first light emitter that emits light having a first wavelength and a second light emitter that emits light having the first wavelength; one or more driver circuits operatively coupled to the array of light emitters and configured to provide drive power required to operate the array of light emitters; a control circuit operatively coupled to the one or more driver circuits and configured to control emission of the light from the first and second light emitters; and a cuff light-delivery system configured to wrap around neural tissue of an animal and to direct the light emitted from the first light emitter to trigger action potentials in a first set of one or more nerves in the neural tissue but substantially not trigger action potentials in a second set of one or more other nerves in the neural tissue, wherein the cuff light-delivery system is further configured to direct the light emitted from the second light emitter to trigger action potentials in the second set of one or more nerves in the neural tissue but substantially not trigger action potentials in the first set of one or more nerves. In some embodiments, the array of light emitters is a VCSEL array.

In some embodiments, the present invention provides a method that includes providing a cuff light-delivery system configured to wrap around neural tissue of an animal, wherein the cuff light-delivery system includes a plurality of vertical cavity surface-emitting lasers (VCSELs) including a first VCSEL and a second VCSEL; emitting pulsed light having a first wavelength from the first VCSEL and the second VCSEL; directing the pulsed light emitted from the first VCSEL to trigger action potentials in a first set of one or more nerves in the neural tissue but substantially not trigger action potentials in a second set of one or more other nerves in the neural tissue; and directing the pulsed light emitted from the second VCSEL to trigger action potentials in the second set of one or more nerves in the neural tissue but substantially not trigger action potentials in the first set of one or more nerves.

In some embodiments of the method, the method further includes identifying which VCSELs in the plurality of VCSELs evoke desired responses based on the directing of the pulsed light; storing the identification in a controller; and selectively controlling the emitting of the pulsed light from the first VCSEL and the second VCSEL based on the stored identification in the controller. In some embodiments, the method further includes delivering an electrical current from a plurality of driver circuits at one end of an electrical cable to a control circuit at another distal end of the electrical cable; and using the electrical current for the selectively controlling of the emitting of the pulsed light from the first VCSEL and the second VCSEL. In some such embodiments, the method further includes partially implanting the control circuit into the animal such that at least part of the control circuit resides external to the animal.

In some embodiments of the method, the providing of the cuff light-delivery system includes completely encircling a circumference of the neural tissue with the cuff light-delivery system. In some embodiments, the providing of the cuff light-delivery system includes implementing the plurality of VCSELs on a single semiconductor substrate.

In some embodiments of the method, the plurality of VCSELs includes a third VCSEL and a fourth VCSEL, and the method further includes emitting pulsed light having a second wavelength from the third VCSEL and the fourth VCSEL; directing the pulsed light from the third VCSEL to pass through the first set of one or more nerves to trigger action potentials in a third set of nerves but substantially not trigger action potentials in the first set of one or more nerves or the second set of one or more nerves; and directing the pulsed light from the fourth VCSEL to pass through the second set of one or more nerves to trigger action potentials in a fourth set of nerves but substantially not trigger action potentials in the second set of one or more nerves or the first set of one or more nerves. In some such embodiments, the first wavelength is in a range of 1.8 microns to 2 microns, and wherein the second wavelength is in a range of 650 nanometers to 850 nanometers.

In some embodiments of the method, the method further includes detecting reflected light from the first set of one or more nerves to determine a first physiological activity in the first set of one or more nerves; and detecting reflected light from the second set of one or more nerves to determine a second physiological activity in the second set of one or more nerves. In other embodiments, the method further includes detecting electrical activity from the first set of one or more nerves to determine a first physiological activity in the first tissue; and detecting electrical activity from the second set of one or more nerves to determine a second physiological activity in the second set of one or more nerves. In some embodiments, the method further includes detecting an amount of light directed to the first and second set of one or more nerves in the neural tissue.

In some embodiments, the present invention provides an apparatus that includes a plurality of vertical cavity surface-emitting lasers (VCSELs) including a first VCSEL and a second VCSEL; means for emitting pulsed light having a first wavelength from the first VCSEL and the second VCSEL; and cuff means for directing the pulsed light emitted from the first VCSEL to trigger action potentials in a first set of one or more nerves in neural tissue of an animal but substantially not trigger action potentials in a second set of one or more other nerves in the neural tissue, and for directing the pulsed light emitted from the second VCSEL to trigger action potentials in the second set of one or more nerves in the neural tissue but substantially not trigger action potentials in the first set of one or more nerves. In some embodiments, the apparatus further includes means for selectively controlling the means for emitting the pulsed light from the first VCSEL and the second VCSEL. In some embodiments, the first VCSEL and the second VCSEL are implemented on a single semiconductor substrate.

In some embodiments of the apparatus, the plurality of VCSELs includes a third VCSEL and a fourth VCSEL, and the apparatus further includes means for emitting pulsed light having a second wavelength from the third VCSEL and the fourth VCSEL, wherein the cuff means further includes: means for directing the pulsed light from the third VCSEL to pass through the first set of one or more nerves to trigger action potentials in a third set of nerves but substantially not trigger action potentials in the first set of one or more nerves or the second set of one or more nerves, and means for directing the pulsed light from the fourth VCSEL to pass through the second set of one or more nerves to trigger action potentials in a fourth set of nerves but substantially not trigger action potentials in the second set of one or more nerves or the first set of one or more nerves.

In some embodiments of the apparatus, the apparatus further includes means for detecting reflected light from the first set of one or more nerves to determine a first physiological activity in the first set of one or more nerves; and means for detecting reflected light from the second set of one or more nerves to determine a second physiological activity in the second set of one or more nerves. In other embodiments, the apparatus further includes means for detecting electrical activity from the first set of one or more nerves to determine a first physiological activity in the first tissue; and means for detecting electrical activity from the second set of one or more nerves to determine a second physiological activity in the second set of one or more nerves.

In some embodiments, the present invention provides an apparatus that includes a plurality of laser light sources configured to generate a plurality of independently controlled laser light signals; a plurality of concentric waveguide bundles including a first waveguide bundle, and a second waveguide bundle arranged around the first waveguide bundle, wherein the plurality of waveguide bundles is operatively coupled to the plurality of laser light sources, wherein the plurality of waveguide bundles is configured to emit the plurality of independently controlled laser light signals toward a first plurality of peripheral nerves in a nerve bundle of an animal in order to independently and separately optically stimulate the first plurality of peripheral nerves of the animal, wherein the first waveguide bundle includes a first plurality of waveguides that have a first length and are arranged around a longitudinal axis at a first radial distance from the longitudinal axis, wherein the second waveguide bundle includes a second plurality of waveguides that have a second length and are arranged around the longitudinal axis at a second radial distance from the longitudinal axis, wherein the second radial distance is larger than the first radial distance, and wherein the first length is longer than the second length; a controller operatively coupled to the plurality of laser light sources and configured to selectively control the plurality of laser light signals emitted from each of the plurality of waveguide bundles such that the plurality of laser light signals provide controlled optical stimulation to the first plurality of peripheral nerves of the animal that triggers action potentials in the first plurality of peripheral nerves.

In some embodiments of the apparatus, the plurality of laser light sources includes a plurality of vertical-cavity-surface-emitting lasers (VCSELs). In some embodiments, each of the first plurality of waveguides includes a faceted end configured to transmit its corresponding laser light signal in a direction that is not parallel to the longitudinal axis but is at least partially radially outward from the longitudinal axis. In some embodiments, the first waveguide bundle is configured such that a face of the faceted end of each of the first plurality of waveguides points in a different direction that is radially-outward and longitudinally angled with respect to the longitudinal axis. In some embodiments, the first plurality of waveguides and the first waveguide bundle are configured to reflect light out of each of the first plurality of waveguides in a radial direction of the first plurality of waveguides. In some embodiments, the faceted ends of the first plurality of waveguides are cleaved. In some embodiments, the faceted ends of the first plurality of waveguides are polished. In some embodiments, the apparatus is configured to be fully implanted in the animal. In some embodiments, the apparatus is a first optical stimulation device of a plurality of optical stimulation devices including the first optical stimulation device and a second optical stimulation device, wherein laser light signals emitted from the first optical stimulation device onto the first plurality of peripheral nerves is insufficient alone to stimulate a nerve action potential (NAP) in the first plurality of peripheral nerves, and wherein laser light signals from the second optical stimulation device onto the first plurality of peripheral nerves of the patient is insufficient alone to stimulate a NAP in the first plurality of peripheral nerves, but wherein laser light signals from the first optical stimulation device and laser light signals from the second optical stimulation device intersecting onto the first plurality of peripheral nerves deliver a trigger amount of pulsed light sufficient to stimulate a NAP in the first plurality of peripheral nerves.

In some embodiments of the apparatus, the apparatus further includes a first plurality of insulated electrical conductors extending along the first waveguide bundle and operatively coupled to the controller, the plurality of electrical conductors including a first electrical conductor connected to a first exposed electrode and a second electrical conductor connected to a second exposed electrode, and wherein the controller is configured to selectively apply an electrical signal to the first electrical conductor and the second electrical conductor to create an electric field across a volume of tissue of the animal between the first electrode and the second electrode. In some such embodiments, the first plurality of insulated electrical conductors further includes a third electrical conductor connected to the controller and to a third exposed electrode, and wherein the controller is configured to selectively and independently control an electrical field through tissue of the animal between the first electrode and the third electrode, and an electrical field through tissue of the animal between the second electrode and the third electrode. In some embodiments, the plurality of electrical conductors includes a third electrical conductor, and wherein the controller is configured to control an electrical voltage between the second electrical conductor and the third electrical conductor. In some embodiments, the apparatus is configured to be implanted in the animal, and configured such that when the longitudinal axis of the first waveguide bundle is substantially parallel to a longitudinal axis of the first plurality of peripheral nerves of the animal, the electric fields and the optical signals trigger nerve action potentials independently in each of a plurality of the nerves in the nerve bundle. In some embodiments, the first plurality of waveguides includes a first plurality of optical fibers and the second plurality of waveguides includes a second plurality of optical fibers. In some embodiments, the first electrode is located near ends of the first plurality of optical fibers, and wherein the second electrode and the third electrode are both located near ends of the second plurality of optical fibers.

In some embodiments, the present invention provides a method for optically stimulating peripheral nerves of an animal, the method including generating a plurality of independently controlled laser light signals; providing a plurality of waveguide bundles including a first waveguide bundle and a second waveguide bundle, wherein the plurality of waveguide bundles is operatively coupled to the plurality of independently controlled laser light sources, wherein the first waveguide bundle includes a first plurality of waveguides having a first length and arranged around a longitudinal axis at a first radial distance from the longitudinal axis, wherein the second waveguide bundle includes a second plurality of waveguides having a second length and arranged around the longitudinal axis at a second radial distance from the longitudinal axis, wherein the second radial distance is larger than the first radial distance, and wherein the first length of the first plurality of waveguides is longer than the second length of the second plurality of waveguides; implanting the plurality of waveguide bundles in the animal; delivering the plurality of independently controlled laser light signals through the plurality of waveguide bundles to the first plurality of peripheral nerves of the animal in order to independently and separately optically stimulate the first plurality of peripheral nerves of the animal; and selectively controlling the plurality of independently controlled laser light signals from the plurality of laser light sources such that the plurality of laser light signals provide controlled optical stimulation to the first plurality of peripheral nerves of the animal that triggers action potentials in the first plurality of peripheral nerves.

In some embodiments of the method, the delivering of the plurality of laser light signals through the plurality of waveguide bundles includes delivering a first laser light signal through a first waveguide at a first time and delivering a second laser light signal through a second waveguide at a second time, the method further comprising: identifying which waveguides in the plurality of waveguide bundles evoke desired responses based on the delivering of the plurality of laser light signals; storing the identification in a controller; and basing the selectively controlling of the plurality of independently controlled laser light signals on the stored identification in the controller. In some embodiments, the method further includes cleaving an end of each of the first plurality of waveguides to form a faceted end, wherein the faceted end is configured to transmit its corresponding laser light signal in a direction that is not parallel to the longitudinal axis but is at least partially radially outward from the longitudinal axis. In some embodiments, the method further includes polishing an end of each of the first plurality of waveguides to form a faceted end, wherein the faceted end is configured to transmit its corresponding laser light signal in a direction that is not parallel to the longitudinal axis but is at least partially radially outward from the longitudinal axis.

In some embodiments of the method, the method further includes selectively controlling an electrical field through tissue of the animal between a first location and a second location separated from one another and both located along the longitudinal axis. In some embodiments, the generating of the plurality of laser light signals includes independently activating each of a plurality of vertical-cavity-surface-emitting lasers (VCSELs). In some embodiments, the selectively controlling of the plurality of laser light signals includes controlling a pulse width of the plurality of laser light signals. In some embodiments, the selectively controlling of the plurality of laser light signals includes controlling a pulse repetition rate of the plurality of laser light signals. In some embodiments, the selectively controlling of the plurality of laser light signals includes controlling a pulse shape of the plurality of laser light signals.

In some embodiments of the method, the method further includes applying a first precharge current of electrical energy across a first volume of tissue, and wherein the selectively controlling includes applying a trigger amount of pulsed light to each of a plurality of separate nerves within the first volume of tissue at one or more times following the application of the precharge current across the first volume of tissue. In other embodiments, the method further includes applying a first precharge current of electrical energy across a first volume of tissue, and wherein the selectively controlling includes applying a trigger amount of pulsed light to each of a plurality of separate nerves within the first volume of tissue at one or more times following the application of the first precharge current across the first volume of tissue; and applying a second precharge current of electrical energy across a second volume of tissue separate from the first volume of tissue, and wherein the selectively controlling includes applying a trigger amount of pulsed light to each of a plurality of separate nerves within the second volume of tissue at one or more times following the application of the second precharge current across the second volume of tissue.

In some embodiments, the present invention provides an apparatus that includes a plurality of laser light sources configured to generate a plurality of independently controlled laser light signals; a plurality of concentric waveguide bundles including a first waveguide bundle, and a second waveguide bundle arranged around the first waveguide bundle, wherein the plurality of waveguide bundles is operatively coupled to the plurality of laser light sources, wherein the plurality of waveguide bundles is configured to emit the plurality of laser light signals toward a first plurality of peripheral nerves of an animal in order to independently optically stimulate the first plurality of peripheral nerves of the animal, and wherein the plurality of concentric waveguide bundles is configured to be fully implanted in the animal; means for delivering the plurality of independently controlled laser light signals through the plurality of waveguide bundles to the first plurality of peripheral nerves of the animal in order to independently and separately optically stimulate the first plurality of peripheral nerves of the animal; and means for selectively controlling the plurality of independently controlled laser light signals from the plurality of laser light sources such that the plurality of laser light signals provide controlled optical stimulation to the first plurality of peripheral nerves of the animal that triggers action potentials in the first plurality of peripheral nerves.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:
1. An apparatus comprising:
   a plurality of vertical cavity surface-emitting lasers (VCSELs) including a first VCSEL that emits pulsed light having a first wavelength, a second VCSEL that emits pulsed light having the first wavelength, a third VCSEL that emits pulsed light having a second wavelength, and a fourth VCSEL that emits pulsed light having the second wavelength;
   a plurality of output optics operatively coupled to the plurality of VCSELs including first output optics coupled to the first VCSEL, second output optics coupled to the second VCSEL, third output optics coupled to the third VCSEL, and fourth output optics coupled to the fourth VCSEL;
   one or more driver circuits operatively coupled to the plurality of VCSELs and configured to provide drive power required to operate the plurality of VCSELs;

a control circuit operatively coupled to the one or more driver circuits and configured to control emission of the pulsed light from the first, second, third, and fourth VCSELs; and a cuff light-delivery system configured to wrap around neural tissue of an animal and to direct the pulsed light emitted from the first VCSEL to trigger action potentials in a first set of one or more nerves in the neural tissue but substantially not trigger action potentials in a second set of one or more other nerves in the neural tissue, wherein the cuff light-delivery system is further configured to direct the pulsed light emitted from the second VCSEL to trigger action potentials in the second set of one or more nerves in the neural tissue but substantially not trigger action potentials in the first set of one or more nerves, wherein the cuff light-delivery system is further configured to direct the pulsed light from the third VCSEL to pass through the first set of one or more nerves to trigger action potentials in a third set of nerves but substantially not trigger action potentials in the first set of one or more nerves or the second set of one or more nerves, and wherein the cuff light-delivery system is further configured to direct the pulsed light from the fourth VCSEL to pass through the second set of one or more nerves to trigger action potentials in a fourth set of nerves but substantially not trigger action potentials in the second set of one or more nerves or the first set of one or more nerves.

2. The apparatus of claim 1, wherein the control circuit is integrated in a single chip with the one or more driver circuits.

3. The apparatus of claim 1, wherein the VCSELs are located on an inner surface of the cuff facing the neural tissue.

4. The apparatus of claim 1, wherein the cuff completely encircles a circumference of the neural tissue.

5. The apparatus of claim 1, wherein the plurality of VCSELs is implemented on a single semiconductor substrate.

6. The apparatus of claim 1, further comprising wherein the plurality of output optics includes a microlens integrated with each of the plurality of VCSELs configured to focus the light emitted from each VCSEL onto different portions of the neural tissue.

7. A method comprising:
providing a cuff light-delivery system configured to wrap around neural tissue of an animal, wherein the cuff light-delivery system includes a plurality of vertical cavity surface-emitting lasers (VCSELs) including a first VCSEL, a second VCSEL, a third VCSEL, and a fourth VCSEL, and wherein the cuff light-delivery system includes a plurality of output optics operatively coupled to the plurality of VCSELs including first output optics coupled to the first VCSEL, second output optics coupled to the second VCSEL, third output optics coupled to the third VCSEL, and fourth output optics coupled to the fourth VCSEL;
emitting pulsed light having a first wavelength from the first VCSEL and the second VCSEL;
directing the pulsed light emitted from the first VCSEL to trigger action potentials in a first set of one or more nerves in the neural tissue but substantially not trigger action potentials in a second set of one or more other nerves in the neural tissue;
directing the pulsed light emitted from the second VCSEL to trigger action potentials in the second set of one or more nerves in the neural tissue but substantially not trigger action potentials in the first set of one or more nerves;
emitting pulsed light having a second wavelength from the third VCSEL and the fourth VCSEL;
directing the pulsed light from the third VCSEL to pass through the first set of one or more nerves to trigger action potentials in a third set of nerves but substantially not trigger action potentials in the first set of one or more nerves or the second set of one or more nerves; and
directing the pulsed light from the fourth VCSEL to pass through the second set of one or more nerves to trigger action potentials in a fourth set of nerves but substantially not trigger action potentials in the second set of one or more nerves or the first set of one or more nerves.

8. The method of claim 7, further comprising:
identifying which VCSELs in the plurality of VCSELs evoke desired responses based on the directing of the pulsed light;
storing the identification in a controller; and
selectively controlling the emitting of the pulsed light from the first VCSEL and the second VCSEL based on the stored identification in the controller.

9. The method of claim 8, further comprising:
delivering an electrical current from a plurality of driver circuits at one end of an electrical cable to a control circuit at another distal end of the electrical cable; and
using the electrical current for the selectively controlling of the emitting of the pulsed light from the first VCSEL and the second VCSEL.

10. The method of claim 7, wherein the providing of the cuff light-delivery system includes completely encircling a circumference of the neural tissue with the cuff light-delivery system.

11. The method of claim 7, further comprising:
illuminating a first tissue that includes the first set of one or more nerves but substantially not illuminating a second tissue that includes the second set of one or more nerves and detecting reflected light from the first set of one or more nerves to determine a first physiological activity in the first set of one or more nerves in response to the triggered action potentials in the first set of one or more nerves; and
illuminating the second tissue but substantially not illuminating the first tissue and detecting reflected light from the second set of one or more nerves to determine a second physiological activity in the second set of one or more nerves in response to the triggered action potentials in the second set of one or more nerves.

12. The method of claim 7, further comprising:
detecting electrical activity from the first set of one or more nerves to determine a first physiological activity in the first tissue; and
detecting electrical activity from the second set of one or more nerves to determine a second physiological activity in the second set of one or more nerves.

13. An apparatus comprising:
a plurality of vertical cavity surface-emitting lasers (VCSELs) including a first VCSEL, a second VCSEL, a third VCSEL, and a fourth VCSEL;
a plurality of output optics operatively coupled to the plurality of VCSELs including first output optics coupled to the first VCSEL, second output optics coupled to the second VCSEL, third output optics coupled to the third VCSEL, and fourth output optics coupled to the fourth VCSEL;
means for emitting pulsed light having a first wavelength from the first VCSEL and the second VCSEL;
means for emitting pulsed light having a second wavelength from the third VCSEL and the fourth VCSEL;

means for encircling the plurality of VCSELs around a plurality of sets of nerves, each set of nerves having one or more nerves in neural tissue of an animal, the plurality of sets of nerves including a first set of one or more nerves and a second set of one or more nerves, wherein the means for encircling includes:

means for directing the pulsed light emitted from the first VCSEL to trigger action potentials in the first set of one or more nerves but substantially not trigger action potentials in the second set of one or more nerves, means for directing the pulsed light emitted from the second VCSEL to trigger action potentials in the second set of one or more nerves but substantially not trigger action potentials in the first set of one or more nerves, means for directing the pulsed light from the third VCSEL to pass through the first set of one or more nerves to trigger action potentials in a third set of nerves but substantially not trigger action potentials in the first set of one or more nerves or the second set of one or more nerves, and means for directing the pulsed light from the fourth VCSEL to pass through the second set of one or more nerves to trigger action potentials in a fourth set of nerves but substantially not trigger action potentials in the second set of one or more nerves or the first set of one or more nerves.

14. The apparatus of claim 13, further comprising means for selectively controlling the means for emitting the pulsed light from the first VCSEL and the second VCSEL.

15. The apparatus of claim 13, wherein the first VCSEL and the second VCSEL are implemented on a single semiconductor substrate.

16. The apparatus of claim 13, further comprising:

means for illuminating a first tissue that includes the first set of one or more nerves but substantially not illuminating a second tissue that includes the second set of one or more nerves and means for detecting reflected light from the first set of one or more nerves to determine a first physiological activity in the first set of one or more nerves in response to the triggered action potentials in the first set of one or more nerves; and means for illuminating the second tissue but substantially not illuminating the first tissue and means for detecting reflected light from the second set of one or more nerves to determine a second physiological activity in the second set of one or more nerves in response to the triggered action potentials in the first set of one or more nerves.

17. The apparatus of claim 13, further comprising:

means for detecting electrical activity from the first set of one or more nerves to determine a first physiological activity in the first tissue; and means for detecting electrical activity from the second set of one or more nerves to determine a second physiological activity in the second set of one or more nerves.

18. The apparatus of claim 1, wherein the neural tissue is optogenetically active neural tissue, and wherein the first and second wavelengths are wavelengths selected to trigger action potentials in the optogenetically active neural tissue.

19. The method of claim 7, wherein the neural tissue is optogenetically active neural tissue, and wherein the first and second wavelengths are wavelengths selected to trigger action potentials in the optogenetically active neural tissue.

20. The apparatus of claim 13, wherein the neural tissue is optogenetically active neural tissue, and wherein the first and second wavelengths are wavelengths selected to trigger action potentials in the optogenetically active neural tissue.

\* \* \* \* \*